(12) United States Patent
Saqi et al.

(10) Patent No.: US 11,918,192 B2
(45) Date of Patent: Mar. 5, 2024

(54) MEDICAL APPARATUS AND METHOD FOR COLLECTING BIOLOGICAL SAMPLES

(71) Applicant: The Trustees of Columbia University in the City of New York, New York, NY (US)

(72) Inventors: Anjali Saqi, New York, NY (US); Keith Yeager, Jersey City, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/850,890

(22) Filed: Jun. 27, 2022

(65) Prior Publication Data
US 2022/0323050 A1    Oct. 13, 2022

Related U.S. Application Data

(63) Continuation of application No. 16/192,153, filed on Nov. 15, 2018, now Pat. No. 11,369,350, which is a
(Continued)

(51) Int. Cl.
*A61B 1/00* (2006.01)
*A61B 10/00* (2006.01)
(Continued)

(52) U.S. Cl.
CPC .......... *A61B 10/0096* (2013.01); *A61B 10/02* (2013.01); *A61M 1/34* (2013.01);
(Continued)

(58) Field of Classification Search
None
See application file for complete search history.

(56) References Cited

U.S. PATENT DOCUMENTS

| 4,518,288 A | 5/1985 | Cilindro |
| 4,534,863 A | 8/1985 | Bacon et al. |

(Continued)

FOREIGN PATENT DOCUMENTS

| CN | 1321106 A | 11/2001 |
| CN | 102507265 A | 6/2012 |

(Continued)

OTHER PUBLICATIONS

International Search Report for PCT/US2013/071083 dated Mar. 21, 2014, 2 pages.
(Continued)

*Primary Examiner* — Jyoti Nagpaul
(74) *Attorney, Agent, or Firm* — BakerHostetler

(57) ABSTRACT

A medical apparatus having an elongate tubular body with a proximal end, an opening at the proximal end, and a distal end defining an interior space therebetween and the distalmost end of the elongate tubular body is configured to matingly engage a filter assembly; a filter assembly configured to matingly engage the distal portion of the elongate tubular body and to provide a seal with the interior space thereof, the filter assembly comprising a filter membrane and a border that is sectionable for mounting on a slide for analysis on a microscope; and a base member configured to releasably engage the distalmost end of the elongate tubular body and to receive the filter assembly therein.

26 Claims, 56 Drawing Sheets

Related U.S. Application Data continuation of application No. 14/646,147, filed as application No. PCT/US2013/071083 on Nov. 20, 2013, now Pat. No. 10,166,009.

(60) Provisional application No. 61/806,667, filed on Mar. 29, 2013, provisional application No. 61/728,682, filed on Nov. 20, 2012.

(51) Int. Cl.
  *A61B 10/02* (2006.01)
  *A61M 1/34* (2006.01)
  *B01L 3/00* (2006.01)
  *G01N 1/40* (2006.01)

(52) U.S. Cl.
  CPC .......... *A61M 1/3403* (2014.02); *B01L 3/502* (2013.01); *B01L 3/5021* (2013.01); *G01N 1/4077* (2013.01); *B01L 2300/0618* (2013.01); *B01L 2300/0681* (2013.01); *B01L 2300/0851* (2013.01); *G01N 2001/4088* (2013.01)

(56) References Cited

U.S. PATENT DOCUMENTS

| | | | |
|---|---|---|---|
| 4,822,495 A | 4/1989 | Michels | |
| 4,957,637 A | 9/1990 | Cornell | |
| 5,026,638 A | 6/1991 | Saperstein | |
| 5,042,502 A | 8/1991 | Guirguis | |
| 5,137,710 A | 8/1992 | Smalley et al. | |
| 5,456,125 A | 10/1995 | Gagne | |
| 5,471,994 A * | 12/1995 | Guirguis ............. | G01N 1/4077 600/584 |
| 5,552,325 A | 9/1996 | Nochumson et al. | |
| 5,556,544 A | 9/1996 | Didier | |
| 5,578,459 A | 11/1996 | Gordon et al. | |
| 5,833,860 A | 11/1998 | Kopaciewicz et al. | |
| 5,860,937 A | 1/1999 | Cohen | |
| 5,882,943 A | 3/1999 | Aldeen | |
| 5,948,687 A | 9/1999 | Cleator | |
| 6,145,688 A | 11/2000 | Smith | |
| 6,296,764 B1 | 10/2001 | Guirguis et al. | |
| 6,322,488 B1 | 11/2001 | Westberg et al. | |
| 6,379,565 B1 | 4/2002 | Guirguis et al. | |
| 6,883,958 B2 | 4/2005 | Mayer | |
| 6,884,397 B2 | 4/2005 | Day | |
| 6,913,921 B2 | 7/2005 | Fischer | |
| 7,176,034 B2 | 2/2007 | Efthimiadis et al. | |
| 7,179,424 B2 | 2/2007 | Williamson, IV et al. | |
| 7,316,779 B2 | 1/2008 | Pressman et al. | |
| 7,488,297 B2 | 2/2009 | Flaherty | |
| 8,152,738 B2 | 4/2012 | Li et al. | |
| 8,268,171 B2 | 9/2012 | Liao | |
| 8,329,120 B2 | 12/2012 | Williamson, IV et al. | |
| 8,623,300 B2 | 1/2014 | Williamson, IV | |
| 8,647,574 B2 | 2/2014 | Halverson et al. | |
| 8,796,038 B2 | 8/2014 | Williamson, IV et al. | |
| 9,541,477 B2 | 1/2017 | Saqi et al. | |
| 2002/0130100 A1 | 9/2002 | Smith | |
| 2002/0192656 A1 | 12/2002 | Richardson et al. | |
| 2003/0215936 A1 | 11/2003 | Kallioniemi et al. | |
| 2004/0137417 A1 | 7/2004 | Ryan | |
| 2006/0037903 A1 | 2/2006 | Smith et al. | |
| 2006/0121597 A1 | 6/2006 | Li | |
| 2007/0166834 A1 | 7/2007 | Williamson et al. | |
| 2008/0097285 A1 | 4/2008 | Scampini | |
| 2010/0184127 A1 | 7/2010 | Williamson, IV et al. | |
| 2010/0248215 A1 | 9/2010 | Halverson et al. | |
| 2010/0297691 A1 | 11/2010 | Ribeiro | |
| 2013/0323711 A1 | 12/2013 | Singh et al. | |
| 2014/0205515 A1 | 7/2014 | Williamson, IV et al. | |
| 2014/0227732 A1 | 8/2014 | Saqi et al. | |
| 2017/0036203 A1 | 2/2017 | Le et al. | |
| 2017/0087228 A1 | 3/2017 | Turzi | |

FOREIGN PATENT DOCUMENTS

| | | |
|---|---|---|
| IN | 201825948 U | 5/2011 |
| JP | 2001-296220 A | 10/2001 |
| JP | 2001-522042 A | 11/2001 |
| JP | 2007-292580 A | 11/2007 |
| JP | 4779433 | 9/2011 |
| WO | 1993/010433 | 5/1993 |
| WO | 1995/014533 | 6/1995 |
| WO | 99/23468 A1 | 5/1999 |
| WO | 2004/041994 | 5/2004 |
| WO | 2006/058078 | 6/2006 |
| WO | 2008/073387 A1 | 6/2009 |
| WO | 2013/059526 A1 | 4/2013 |
| WO | 2014/081877 | 5/2014 |
| WO | 2016/028997 A1 | 2/2016 |

OTHER PUBLICATIONS

Nathan, NA et al. "Cell Block Cytology: Improved Preparation and Its Efficacy in Diagnostic Cytology" (2000) Am J Clin Pathol, vol. 114. Issue 4, pp. 599-606.

Nigro, K. et al. Comparison of Cell Block Preparation Methods for Nongynecologic ThinPrep Specimens (2007) Diagnostic Cytopathology, vol. 35. Issue 10, pp. 640-643.

Varsegi et al. "Cell Block Preparation from Cytology Specimen Predominance of Individually Scattered Cells." Journal of Visualized Experiments. 29: 1-7. Jul. 21, 2009.

Yang, G.C. et al. "Compact cell blocks. Use for body fluids, fine needle aspirations and endometrial brush biopsies." (1998) Acta Cytologica, vol. 42, Issue 3, pp. 703-706.

Extended European Search Report dated May 29, 2015 in corresponding Application No. 12841594.0.

Loukeris, K. et al. "Cytological Cell Blocks: Predictors of Squamous Cell Carcinoma and Adenocarcinoma Subtypes."(2010) Diagonostic Cytopathology, DOI 10.1002/dc21519.

Rekhtman.N. et al. "Suitability of Thoracic Cytology for New Therapeutic Paradigms in Non-small Cell Lung Carcinoma." (Mar. 2011) Journal of Thoracic Oncology, vol. 6, No. 3.

Rekhtmann, N., et al. "Immunohistochemical algorithm for differentiation of lung adenocarcinoma and squamous cell carcinoma based on large series of whole-tissue Sectuibs with validation in Small specimens" (2011) Modern Pathology, vol. 24, pp. 1348-1359.

International Search Report PCT/US12/60914, (dated Jan. 9, 2013).

Notice of Reasons for Refusal, Japanese Application No. 2015-544116 (dated Oct. 3, 2017), English translation (5 pages).

International Search Report and Written Opinion cited in International Application PCTIUS2020/018121 dated Aug. 20, 2020.

Examination Report No. 1 for Standard Patent Application cited in corresponding Australian Application No. 2017279815 dated Jun. 11, 2019.

Supplementary European Search Report cited in corresponding European Application No. 13856084 dated Jun. 16, 2016.

U.S. Appl. No. 16/192,153, filed Nov. 15, 2018.

U.S. Appl. No. 14/646,147, filed May 20, 2015.

* cited by examiner

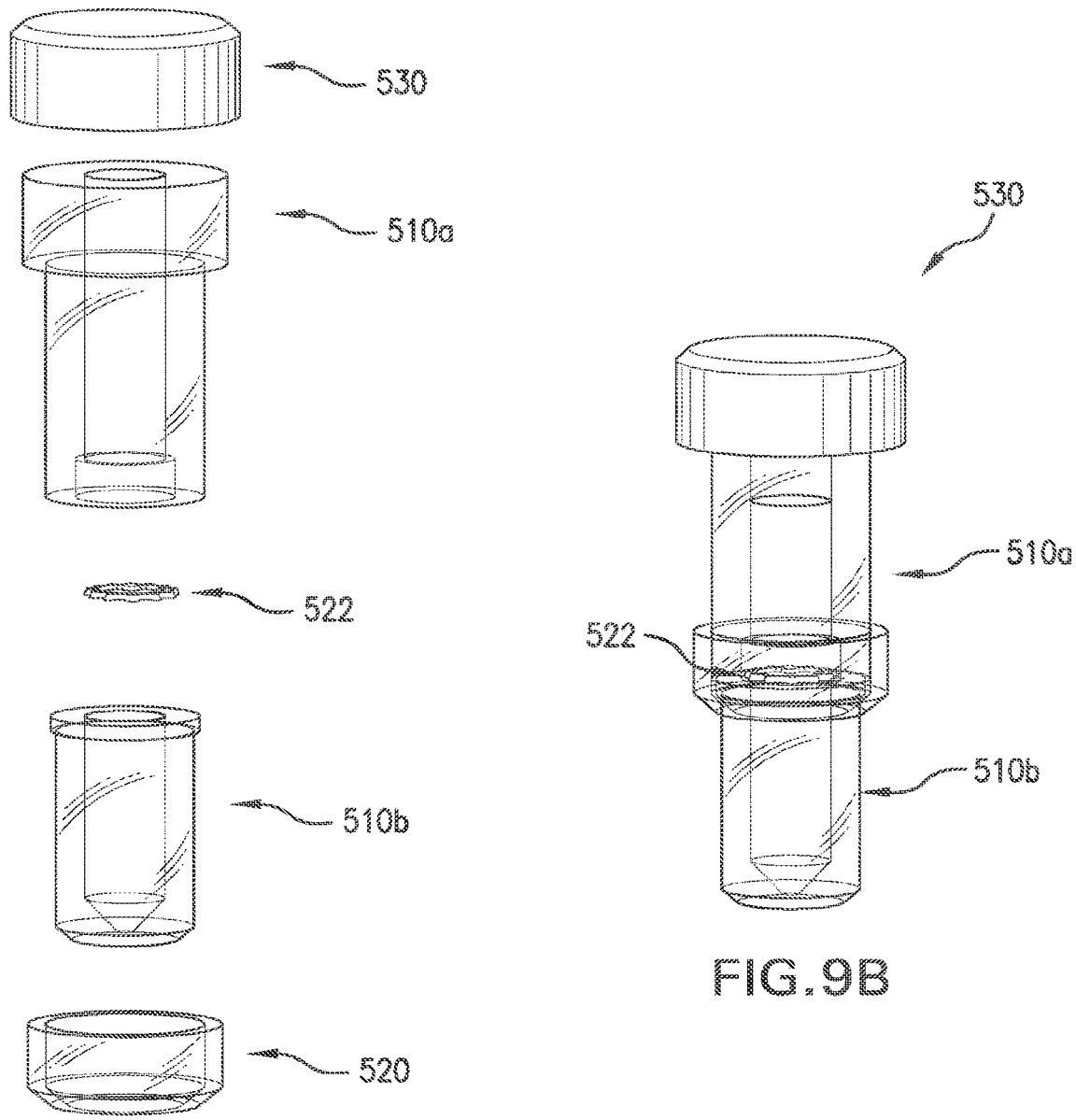

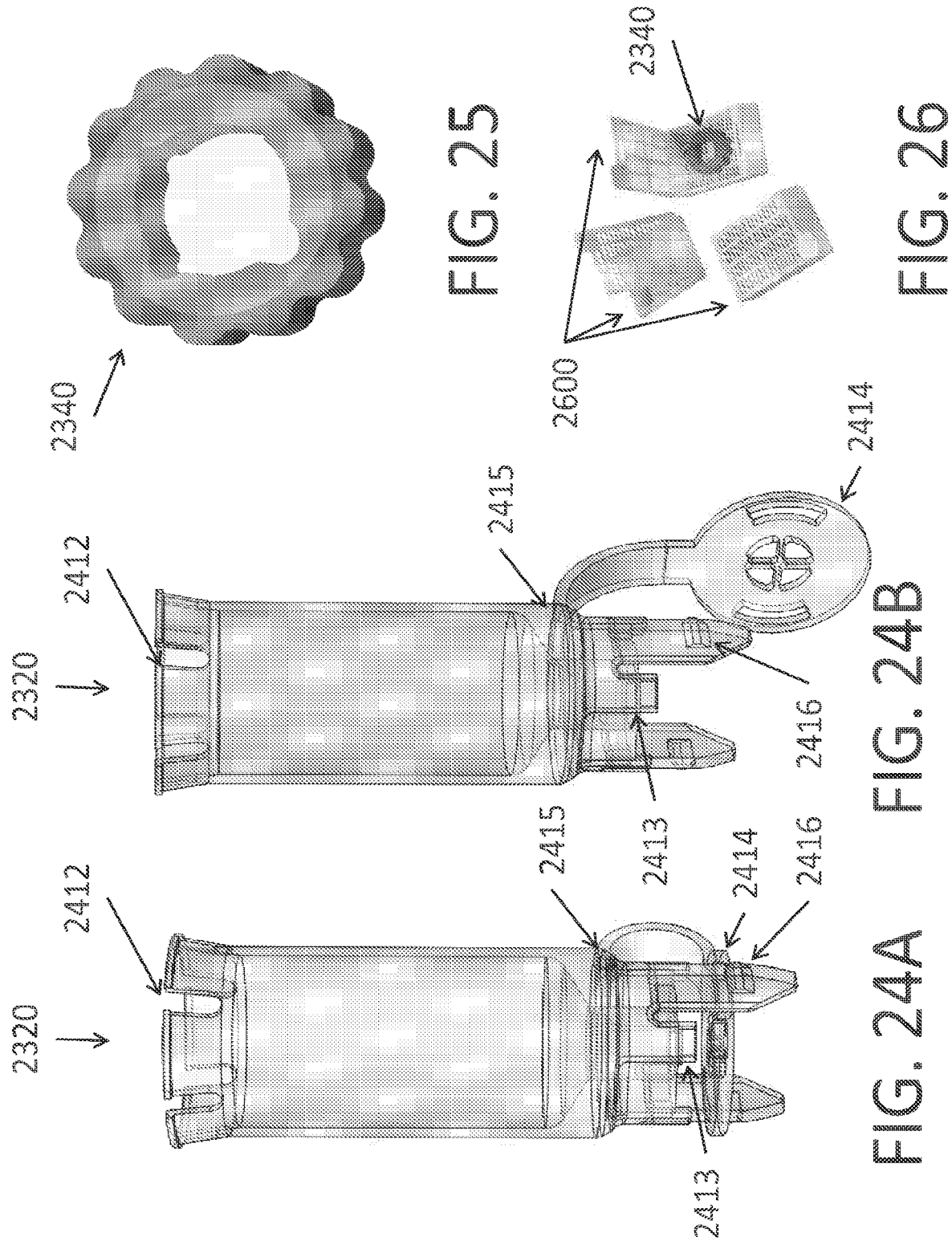

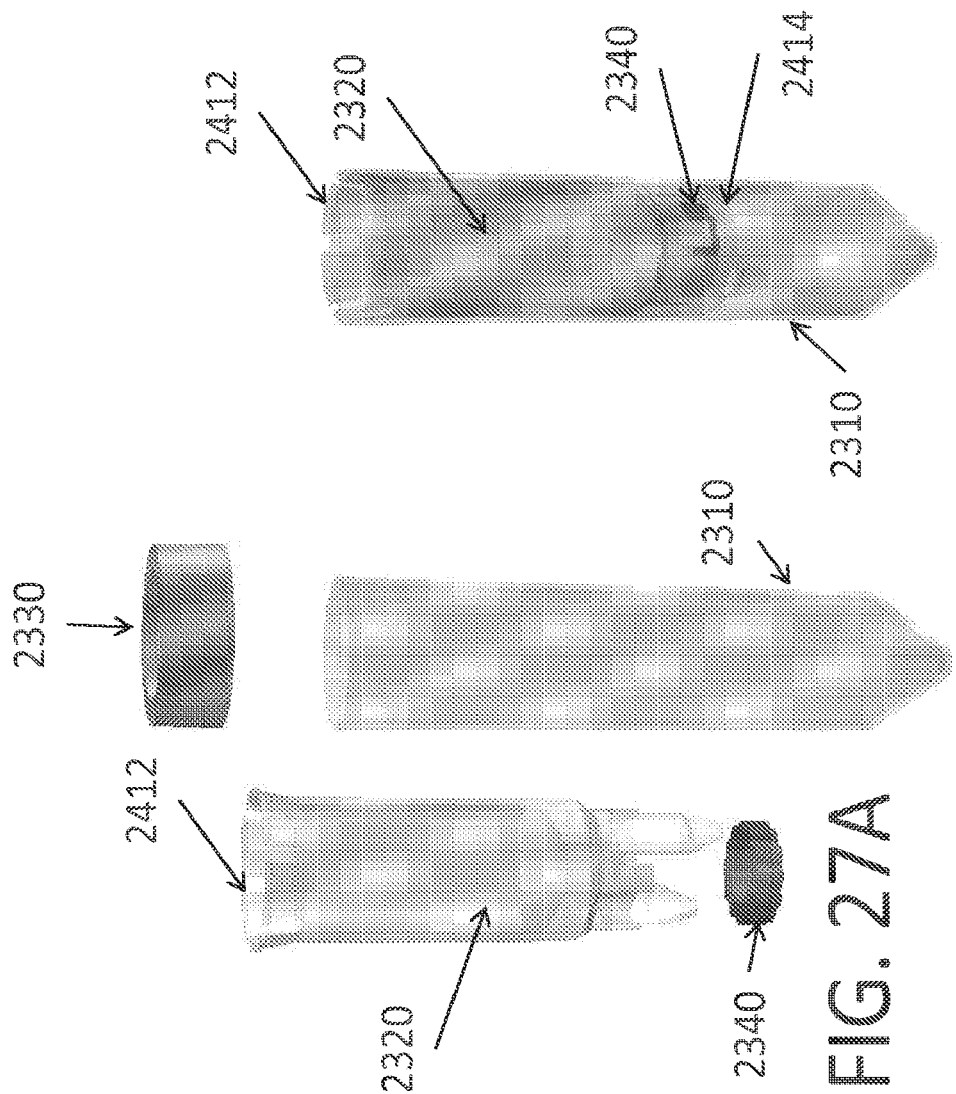

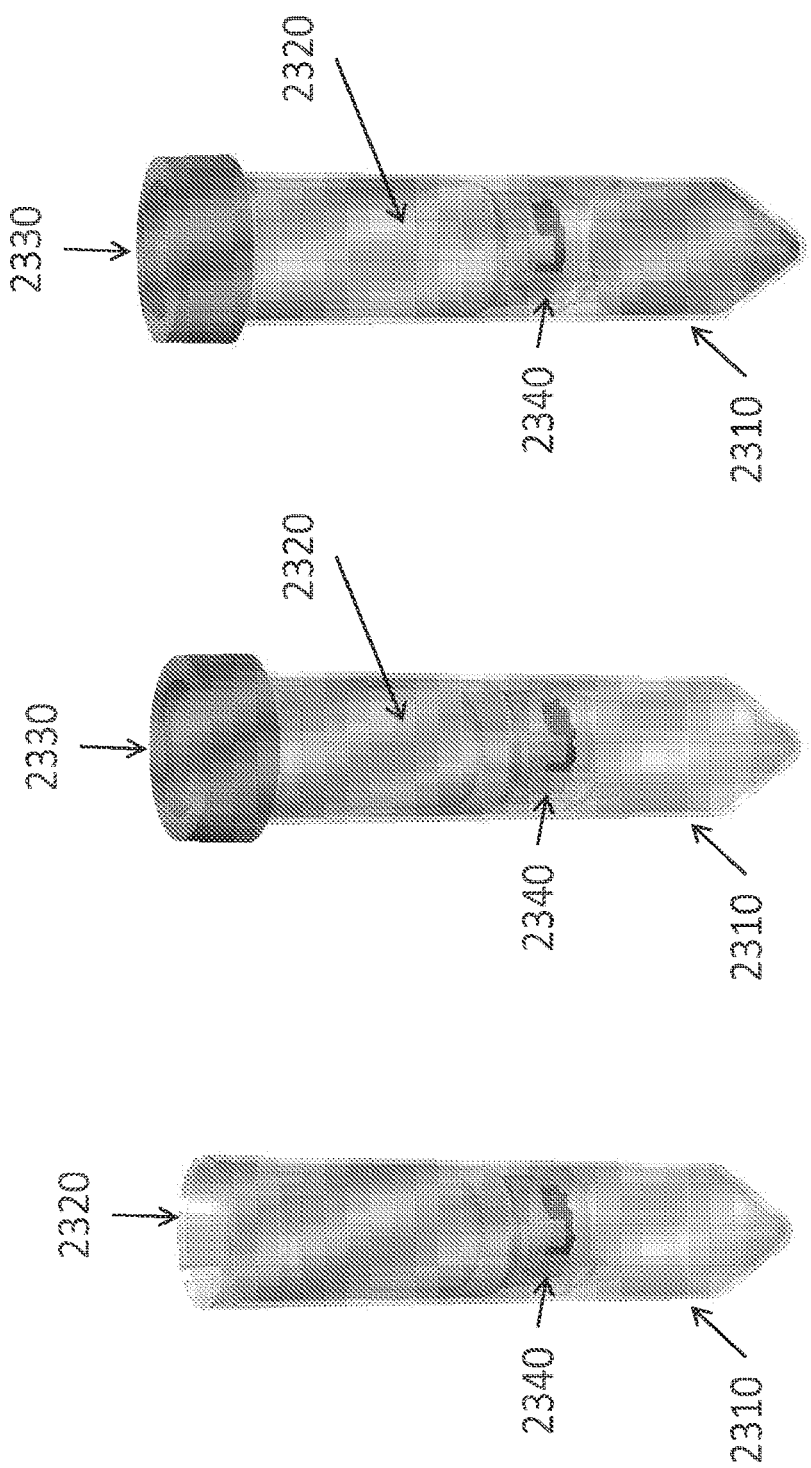

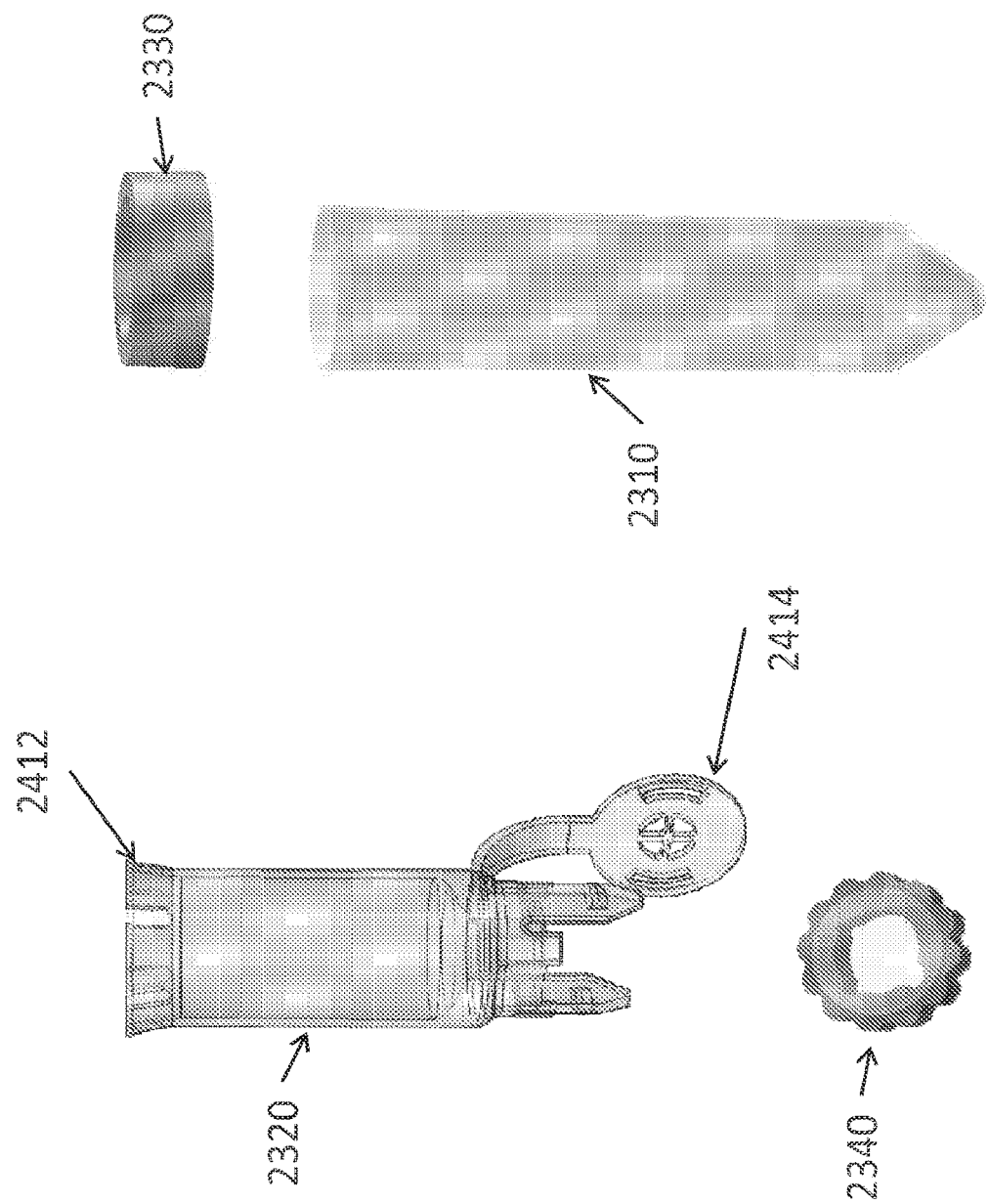

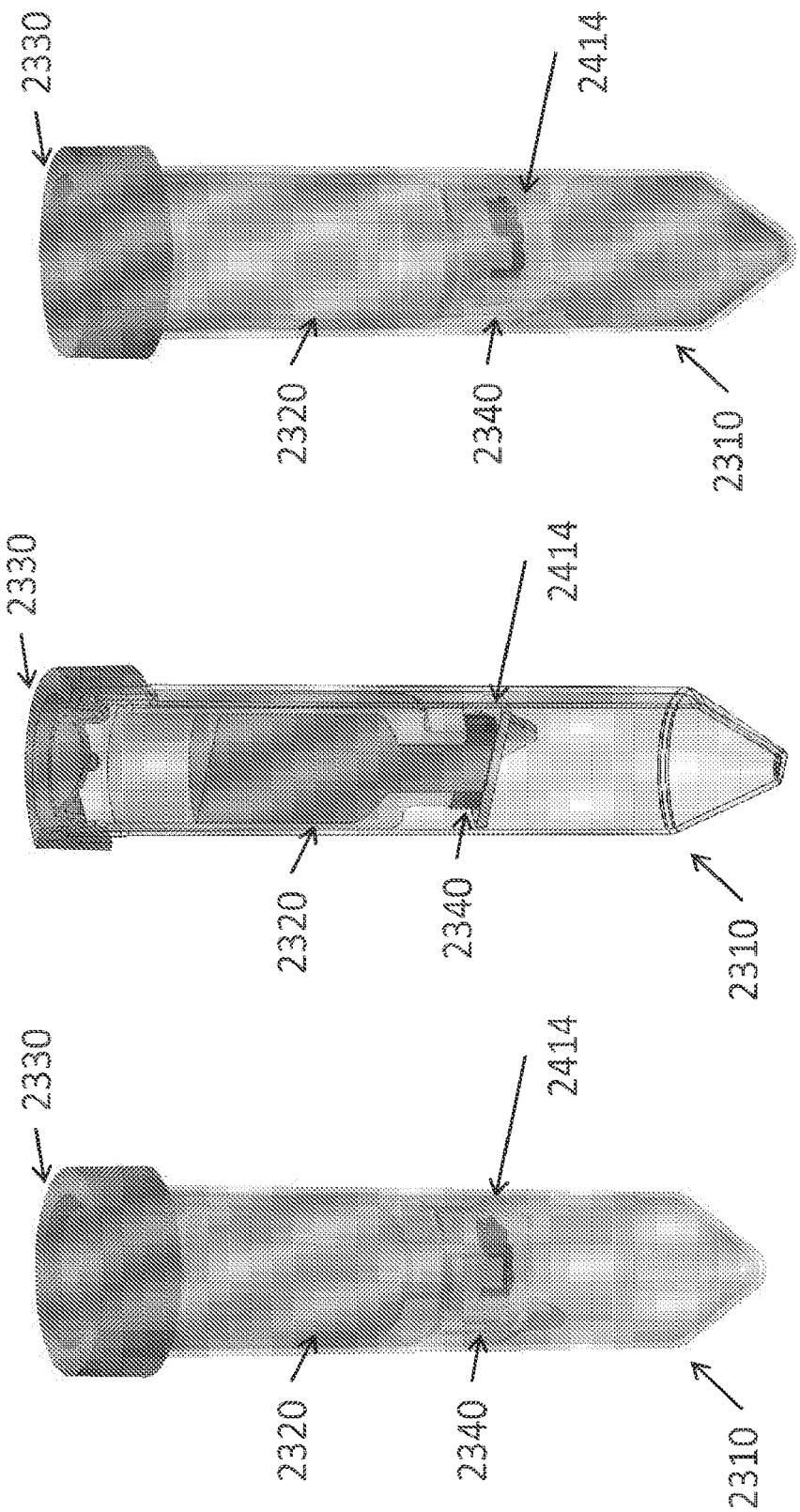

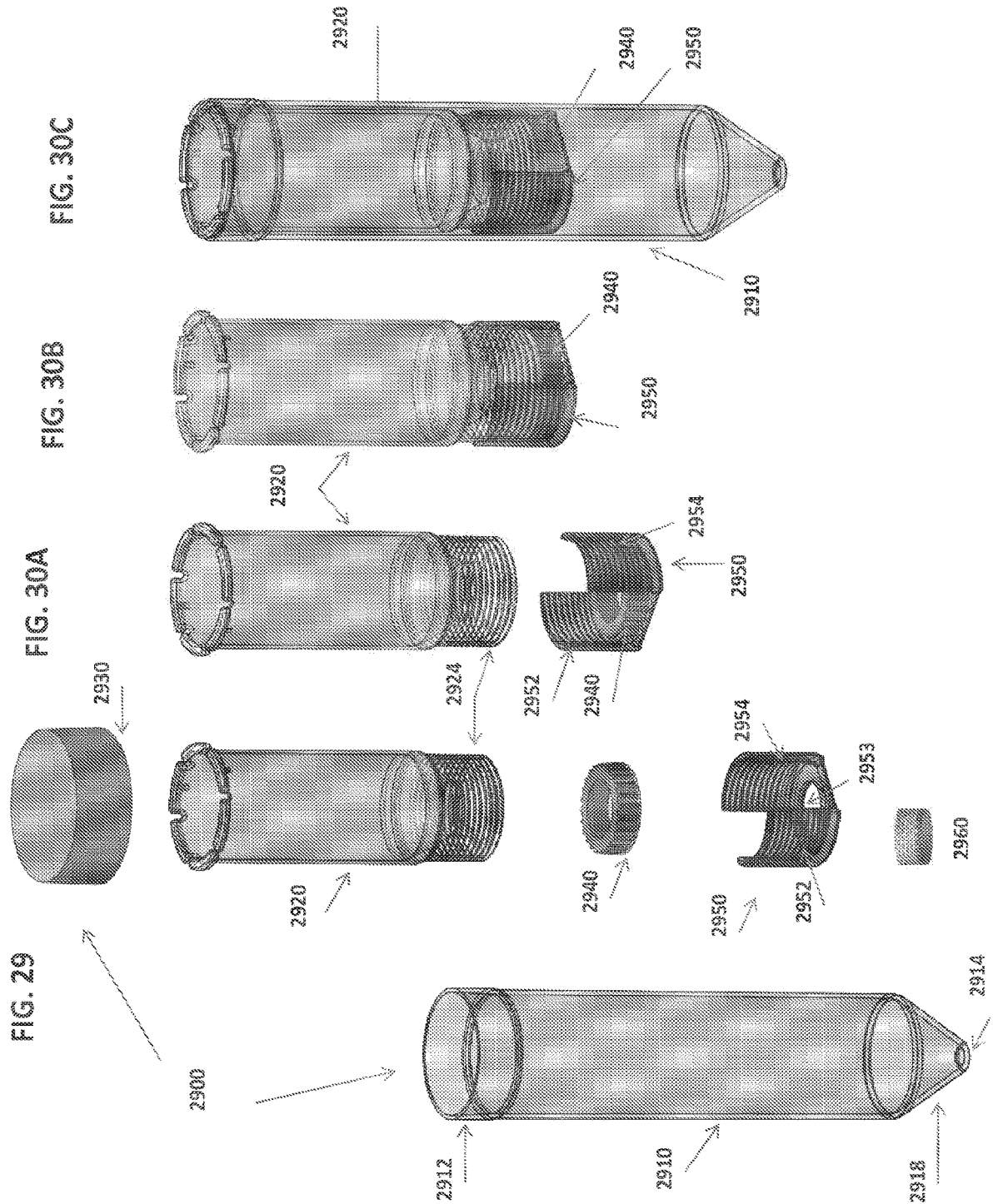

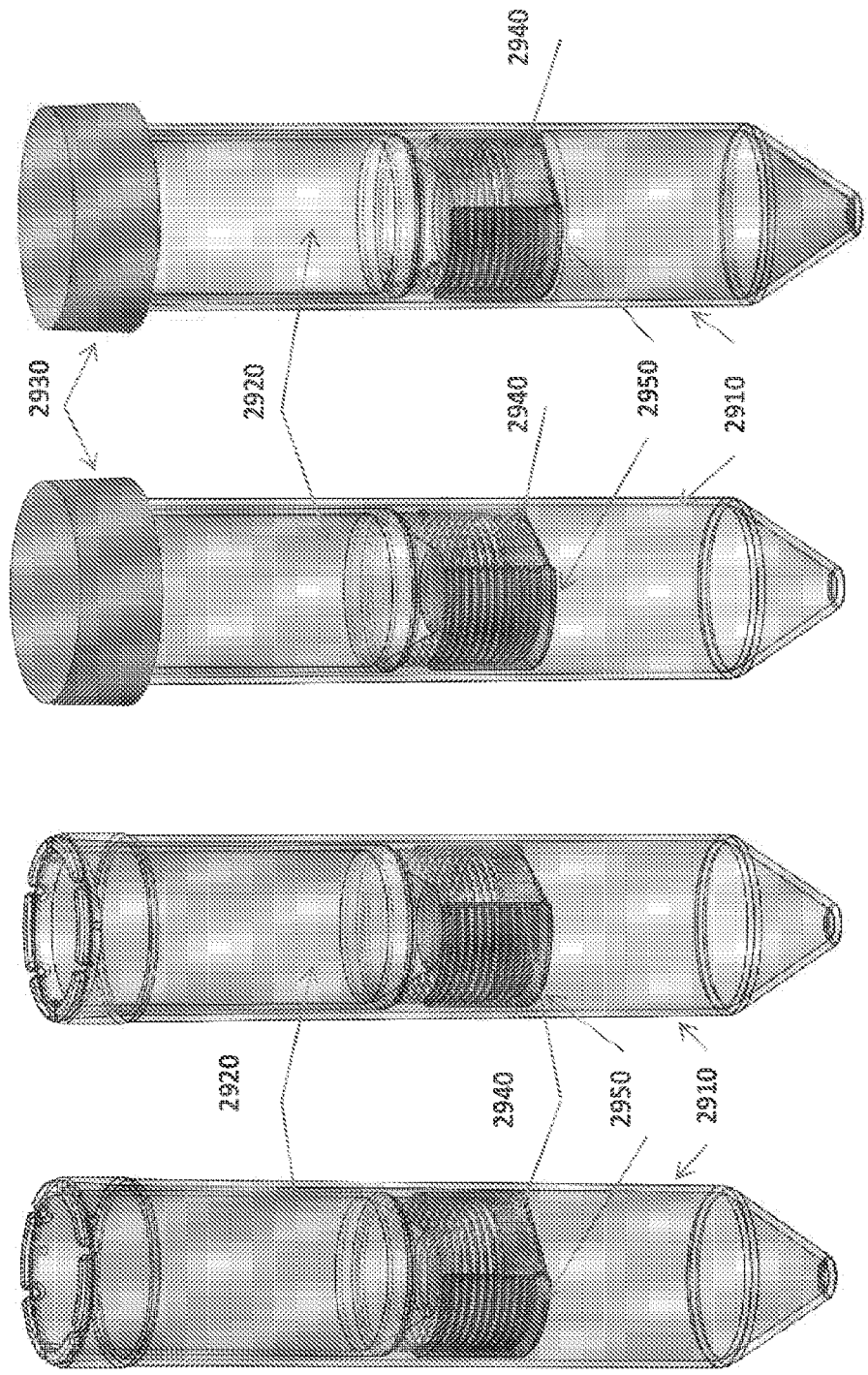

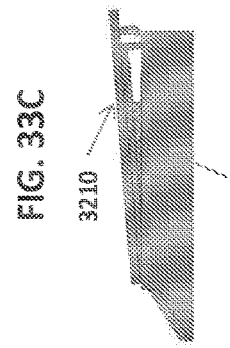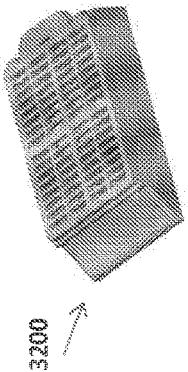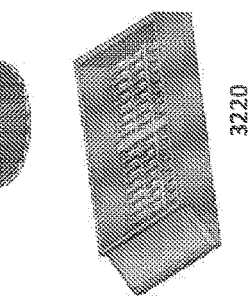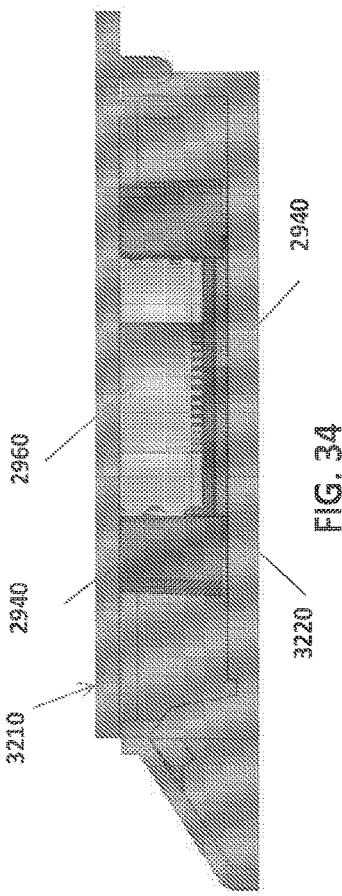

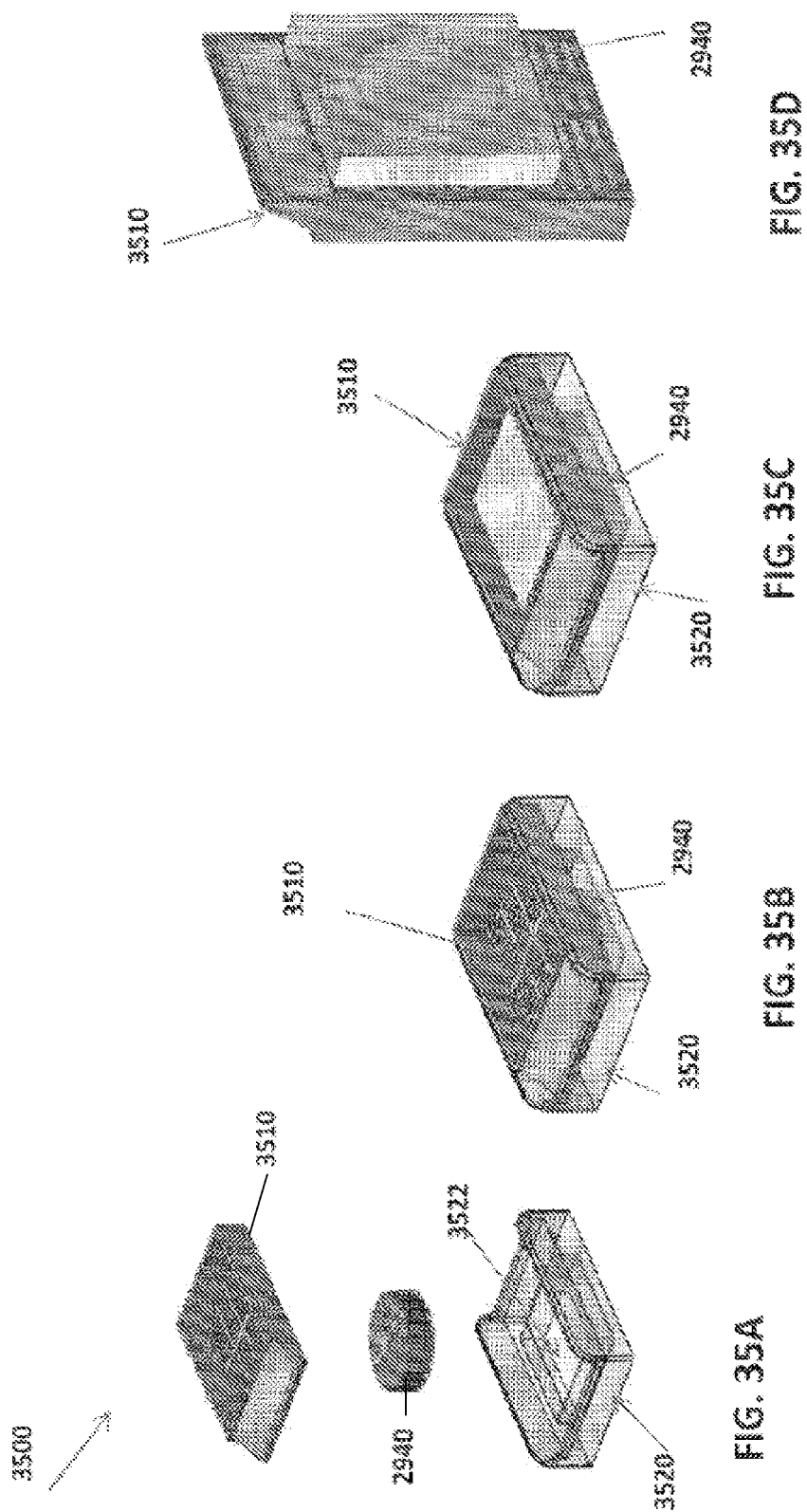

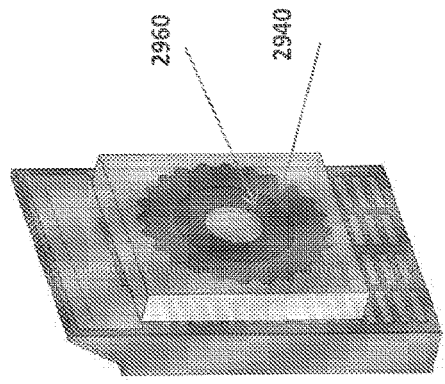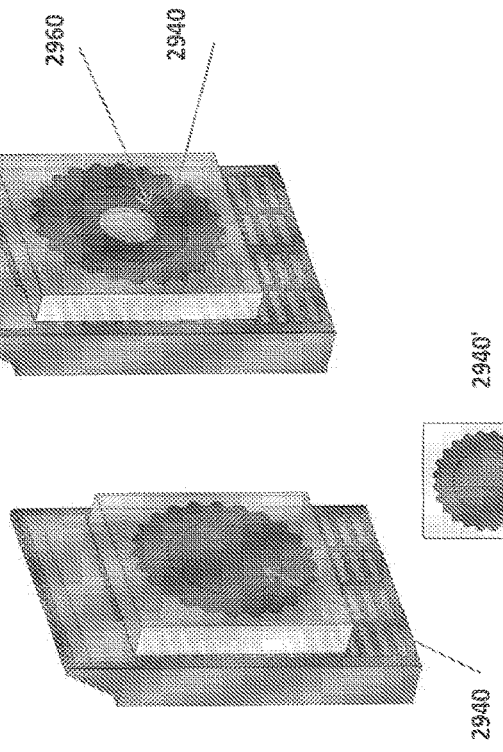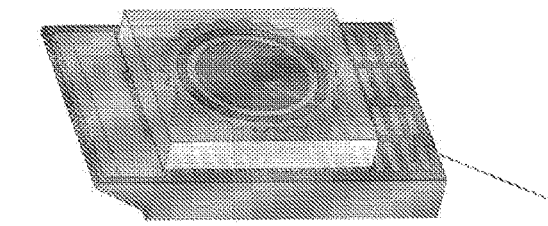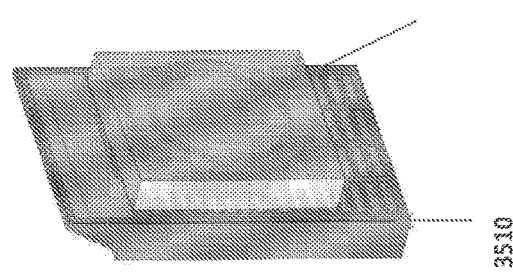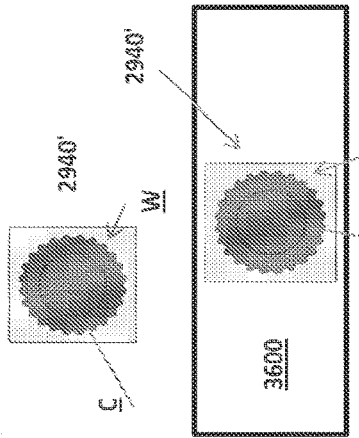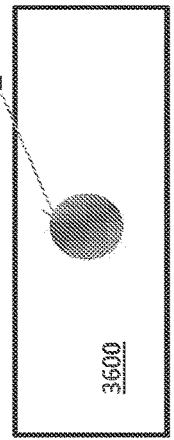

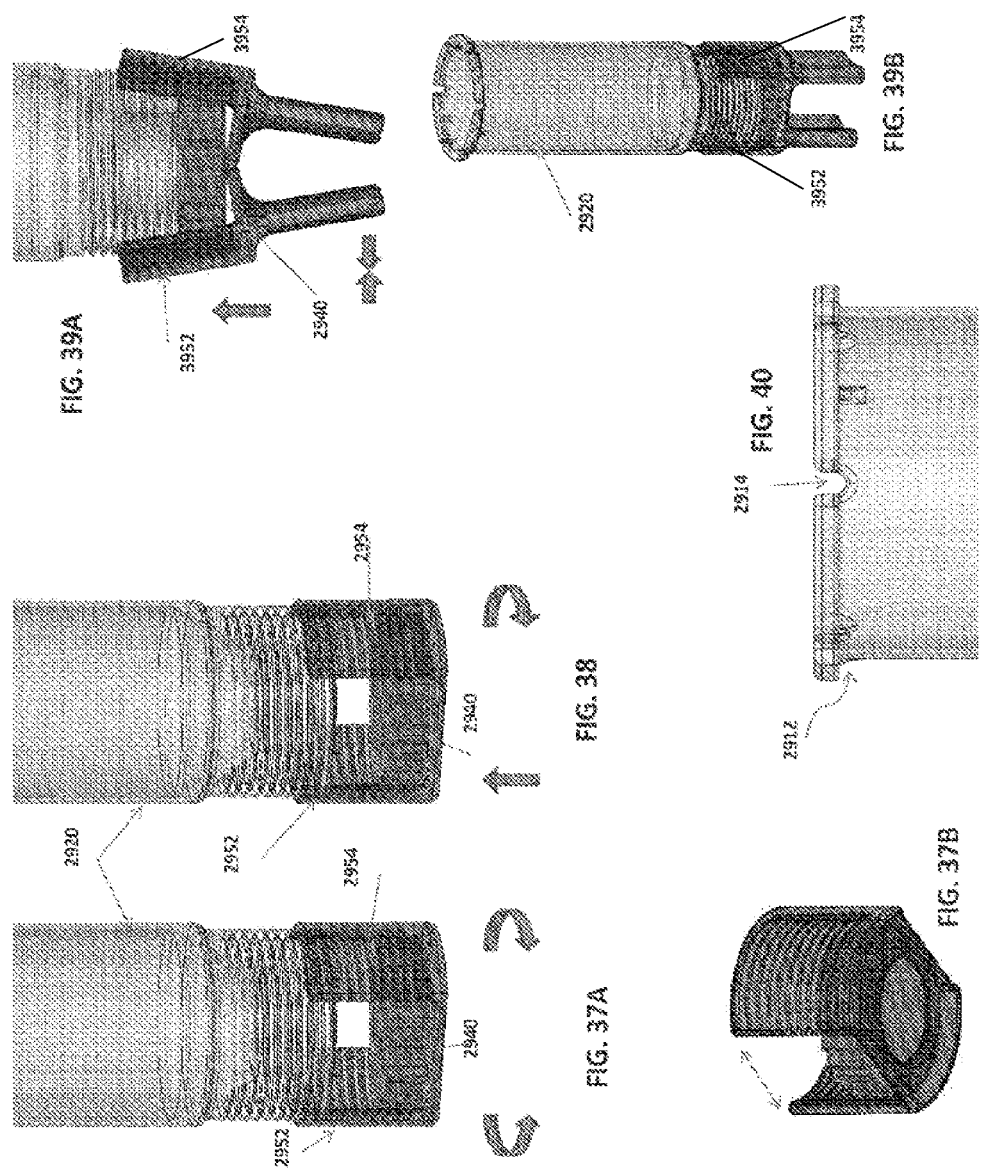

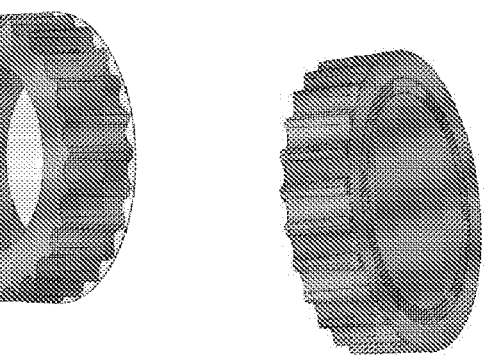
FIG. 41
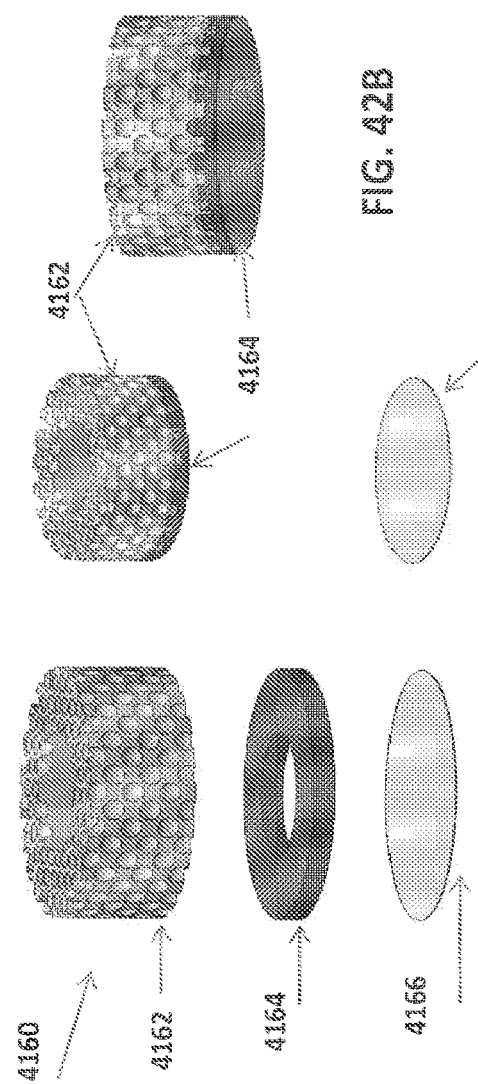
FIG. 42A
FIG. 42B
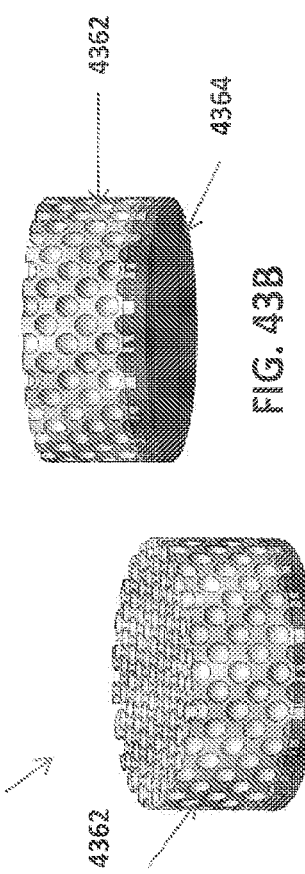
FIG. 43A
FIG. 43B

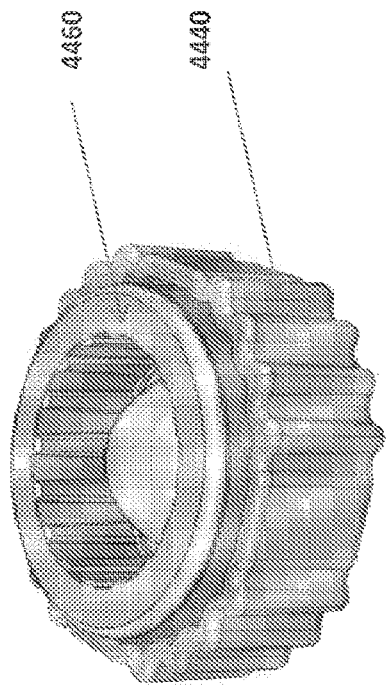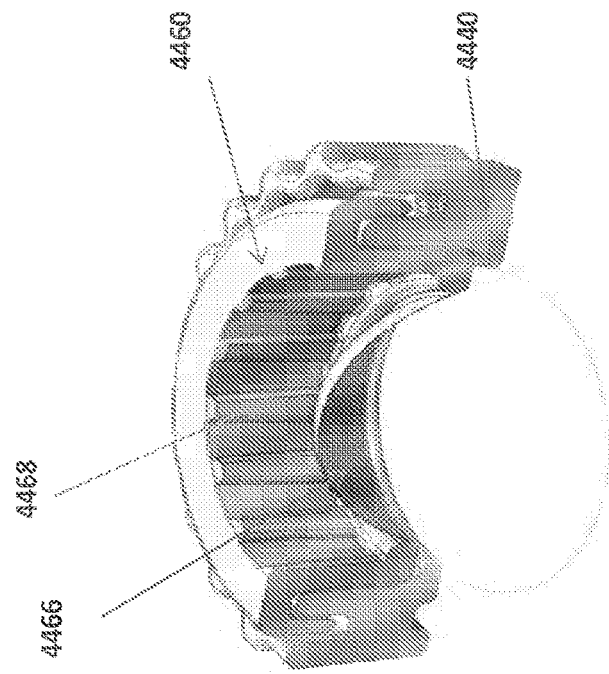
FIG. 45
FIG. 46A

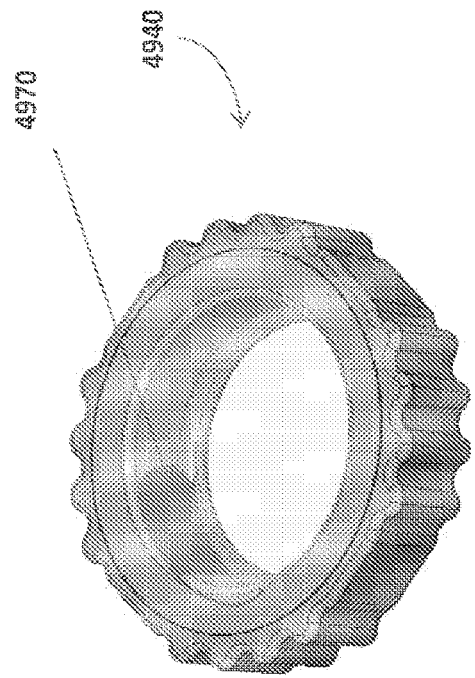
FIG. 49
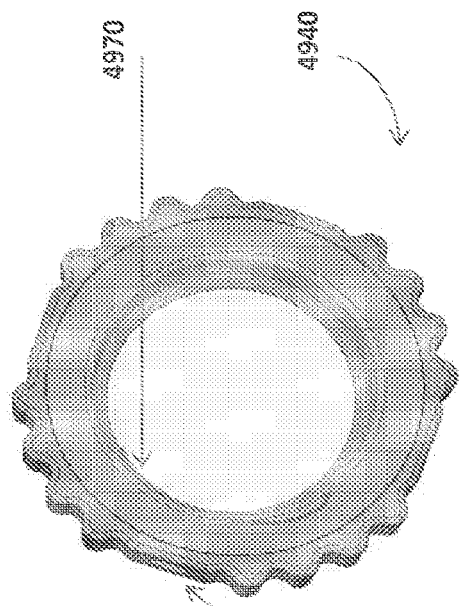
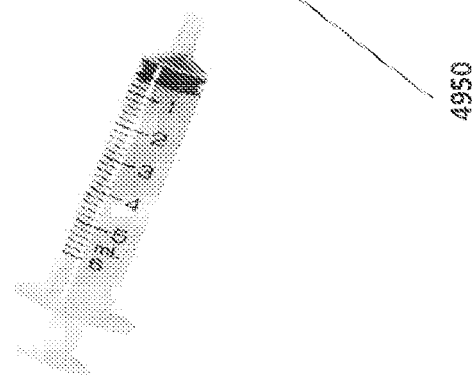
FIG. 50

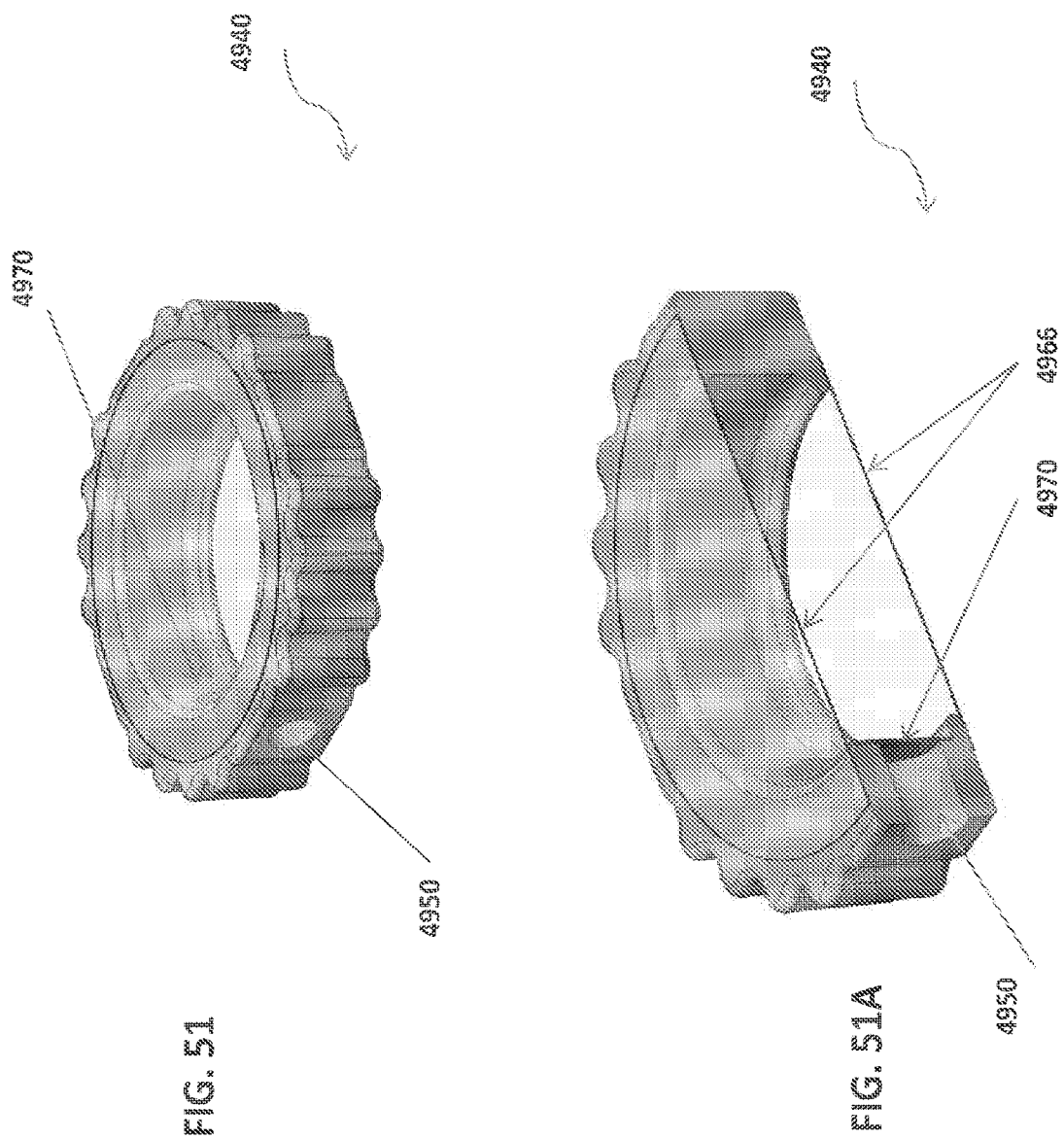

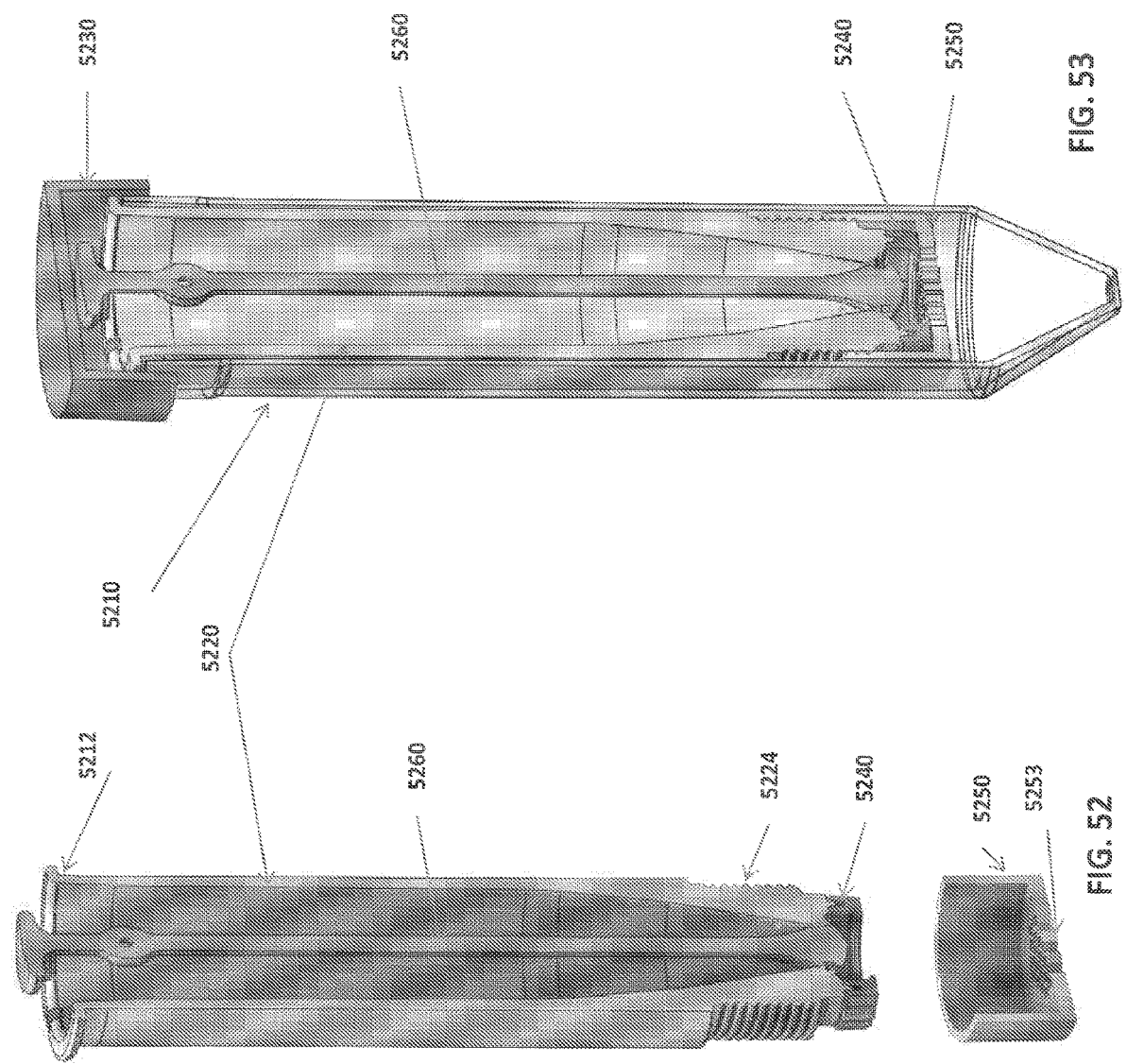

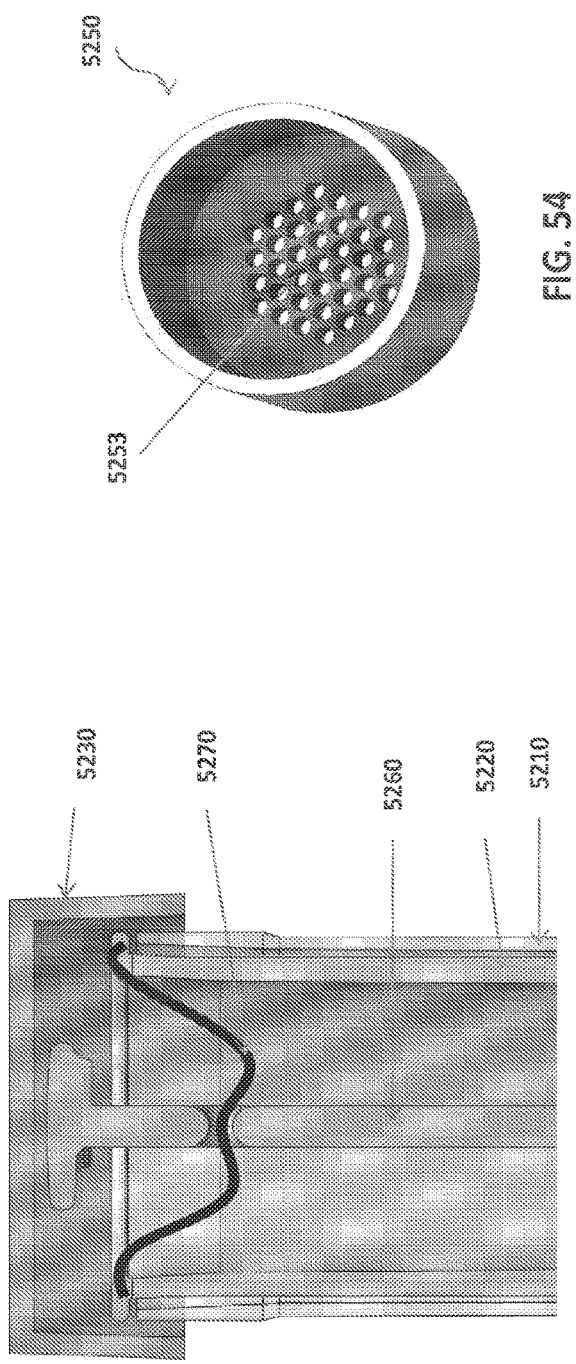
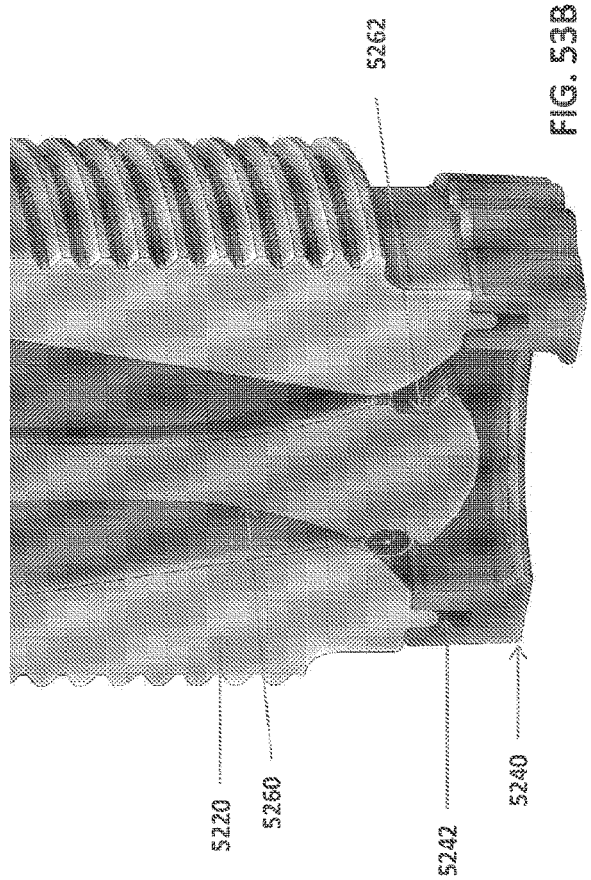
FIG. 53A
FIG. 53B
FIG. 54

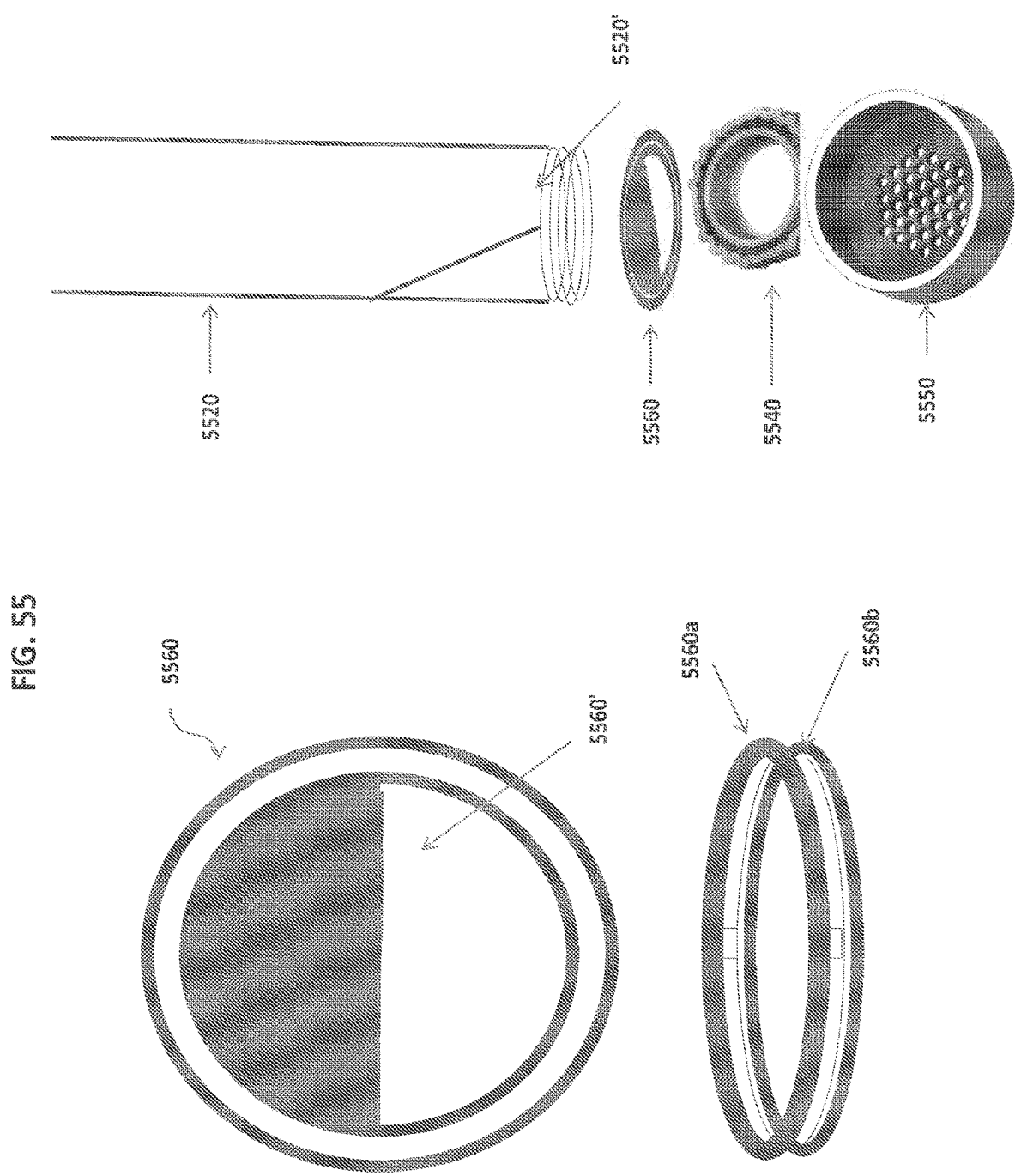

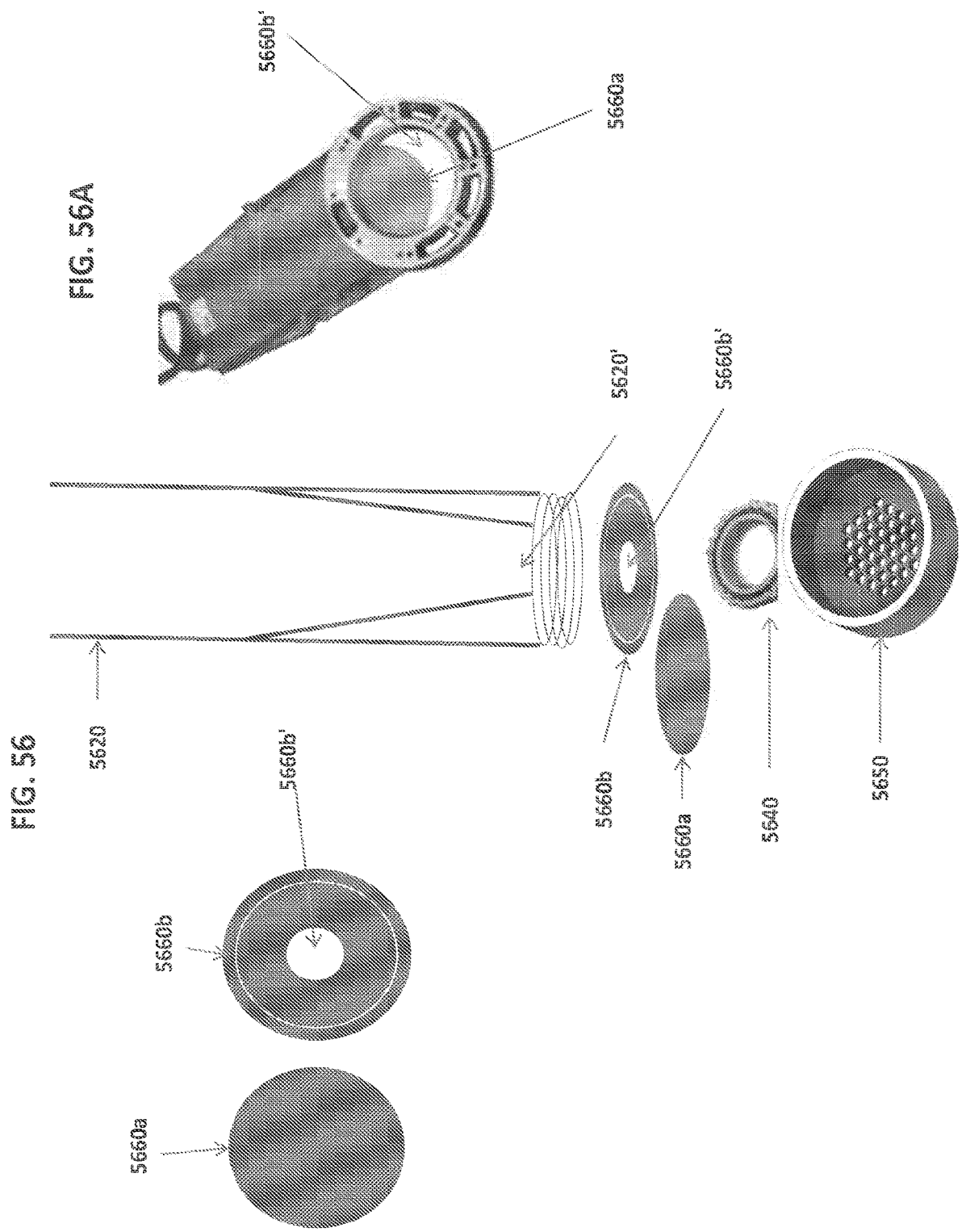

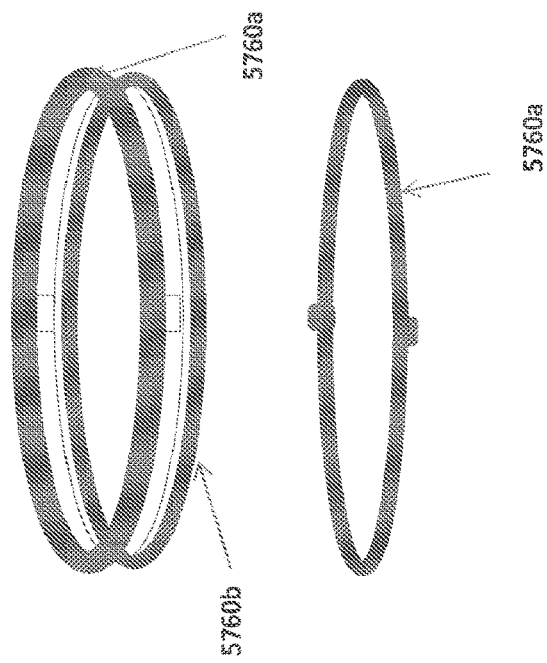
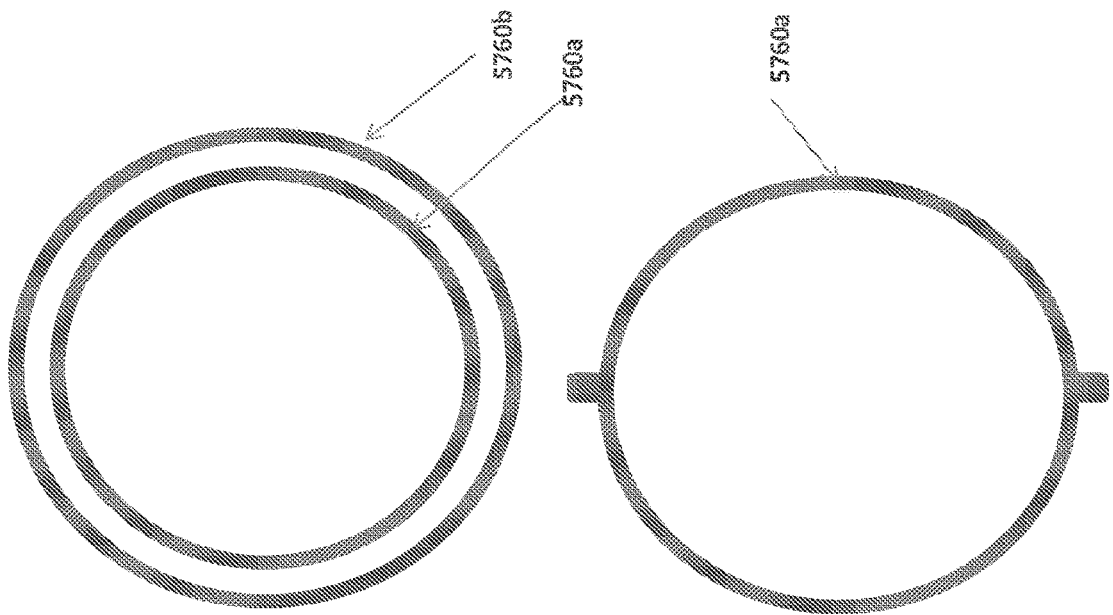

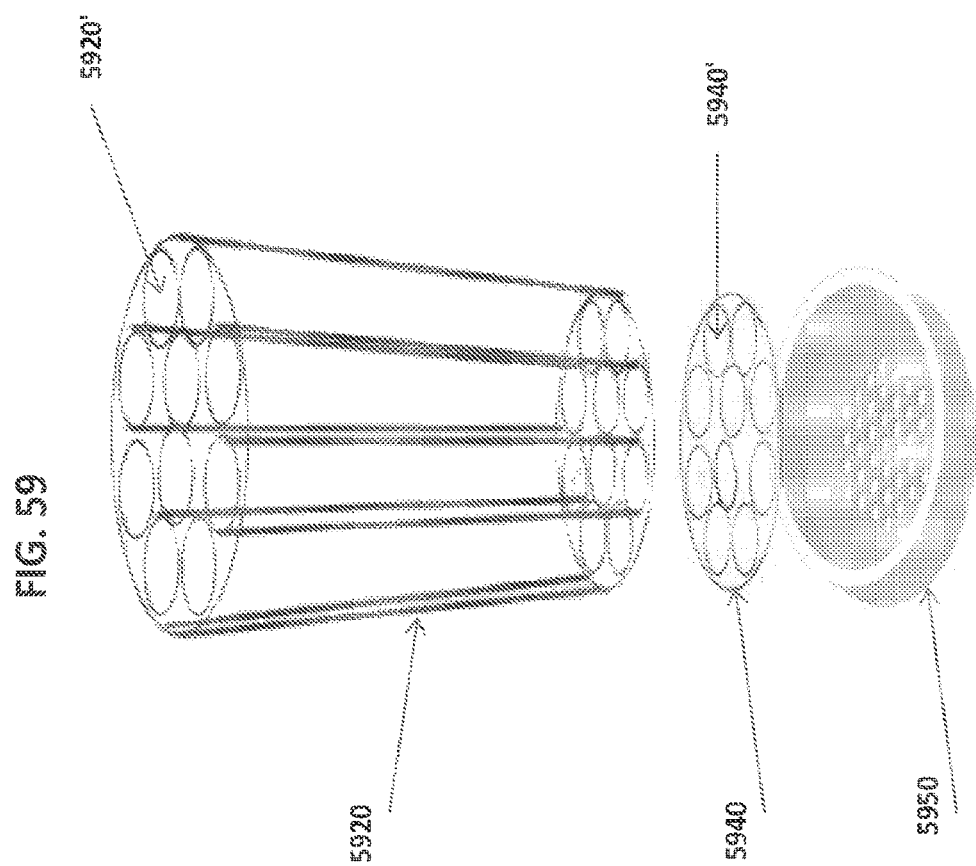

MEDICAL APPARATUS AND METHOD FOR COLLECTING BIOLOGICAL SAMPLES

CROSS REFERENCE TO RELATED APPLICATIONS

This application is a continuation of U.S. application Ser. No. 16/192,153, filed Nov. 15, 2018, which is a continuation of U.S. application Ser. No. 14/646,147 filed May 20, 2015, now U.S. Pat. No. 10,166,009, which is a 35 U.S.C. § 371 of International Patent Application No. PCT/US2013/071083, filed Nov. 20, 2013, which claims priority to U.S. Provisional Application No. 61/806,667 filed Mar. 29, 2013 and U.S. Provisional Application No. 61/728,682, filed Nov. 20, 2012, the contents of which are hereby incorporated by reference in their entirety.

FIELD

The disclosed subject matter relates to a system and method for preparing cells for diagnostic tests and procedures. Particularly, the disclosed subject matter relates to a cell block apparatus and methods for preparing a cell block.

BACKGROUND

Medicine is becoming less invasive and more personalized. For example, a patient presenting with a mass in the lung or pancreas is not necessarily scheduled for surgery to characterize the lesion as neoplastic or not. Instead, a minute sample of cells from the lesion is obtained through a procedure called a fine needle aspiration (FNA), which involves aspirating cells with a small needle after it is localized to the site of interest with the aid of CT scan and/or ultrasound. When performing FNA, either no incision is made, or the biopsy site is inconspicuous, similar to a puncture wound following a blood draw, which allows for outpatient procedures and prevents need for hospitalization. By examining cells under a microscope, pathologists render diagnoses of benignity or malignancy. At one time, there were limited treatment options and diagnoses of malignancy made on smears would suffice and treatment would ensue. Nowadays, ancillary tests afford greater information about the tumor and therapeutic options that are likely to be more effective. Though minimally invasive procedures and personalized treatment options provide better patient care, imparting greater levels of information on even smaller tissue samples is challenging and places a greater burden on pathologists and consequences for patients.

Ancillary tests to answer the pertinent questions are frequently conducted on cell blocks, pellets of cells formed from the FNA sample, if available. Currently, there is no accepted laboratory standard on the preparation of cell blocks, though labs frequently employ one of several "homebrew" methods. When samples are large, cell blocks are easier to form, but with smaller samples, the "homebrew" methods may fail or result in a suboptimal cell block. Thus, there is a growing need to develop a standardized apparatus and method for preparing cell blocks in a low cost and efficient manner to provide answers to clinicians that impact therapeutic decisions.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described herein, one aspect of the disclosed subject matter includes a medical, e.g., cell block, apparatus. Such a cell block apparatus is useful for collecting and condensing a biological sample (e.g., cellular tissue, blood and/or mucus) into a cohesive pellet and separating it from any serum and fixative or solution added to preserve the cells for analysis. In some embodiments the medical apparatus comprises a biological filter comprising a filter membrane with a top surface and a bottom surface and a frame having an upwardly extending sidewall circumscribing the filter membrane wherein the sidewall including a channel disposed therein. A bottom surface of the frame is disposed proximate the bottom surface of the filter membrane and the filter membrane and frame are sectionable (e.g., sliced into a plurality of pieces). A cover can also be provided having a flange with a downwardly extending sidewall and a central portion, the central portion having a raised (e.g. dome) surface having an apex disposed below the flange. Additionally, the cover flange includes a lip portion, the lip portion configured to matingly engage the frame channel. Also, the bottom surface of the frame can include a plurality of apertures. In some embodiments the border can be composed of wax and include undulating peaks and valleys as well as a planar surface. Also, the cover sidewall includes a plurality of vertical ribs.

In another embodiment, a biological filter comprises a first filter membrane, the first filter membrane having a top surface and a bottom surface; and a second filter membrane, the second filter membrane having a top surface and a bottom surface. A frame is also provided having an upwardly extending sidewall circumscribing the first and second filter membranes; a bottom surface of the frame disposed substantially coplanar with the bottom surface of the first filter membrane, and a top surface of the frame disposed substantially coplanar with the top surface of the second filter membrane, wherein the first and second filter membranes and frame are sectionable. An inlet port is disposed in the sidewall of the frame with a valve disposed on an interior surface of the frame sidewall proximate the inlet port. The valve is biased in a closed position.

In another embodiment a medical apparatus comprises a sample loading chamber having a proximal end and a distal end defining an interior space therebetween; a filter membrane disposed at the distal end of the sample loading chamber; and a valve stem, the valve stem disposed within the sample loading chamber, the valve stem biased in a closed position to prevent fluid communication between the sample loading chamber and the filter membrane. Additionally, a clamp is provided wherein the filter membrane is retained by the clamp. The clamp includes a bottom surface having at least one aperture and sidewall, and the clamp is attached to the sample loading chamber by a threaded engagement. Furthermore, the valve stem extends proximally beyond the sample loading chamber, and includes an aperture for receiving a spring. The spring extends across the proximal end of the sample loading chamber to engage the sidewalls thereof. Moreover a cap is provided which engages a proximal end of the valve stem to open the valve and permit fluid communication between the sample loading chamber and the filter membrane. The distal end of the sample loading chamber has a narrower opening than the proximal end such that the valve stem matingly engages the sidewalls of the sample loading chamber, when in the closed position.

Additionally, the apparatus or select components thereof can be disposable, or designed for repeated use and cleansing.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

FIG. 9A is an exploded view of an alternative exemplary embodiment of the disclosed subject matter;

FIG. 9B is a schematic diagrams showing the assembled embodiment of FIG. 9A;

FIG. 24A is a schematic diagram of a 15 mL sample holding chamber of an exemplary embodiment of the disclosed subject matter in a closed configuration.

FIG. 24B is a schematic diagram of a 15 mL sample holding chamber of an exemplary embodiment of the disclosed subject matter in an open configuration.

FIG. 25 is a schematic diagram of a filtration insert of an exemplary embodiment of the disclosed subject matter.

FIG. 26 is a schematic diagram of a container for storage of the filter membrane of FIG. 25 according to an exemplary embodiment of the disclosed subject matter.

FIGS. 27A-F are schematic diagrams of the assembly of the sample holding chamber of FIG. 24A-B and the filter membrane of FIG. 25 within a 50 mL tube according to an exemplary embodiment of the disclosed subject matter.

FIGS. 28A-E are schematic diagrams of the assembly of the sample holding chamber of FIG. 24A-B and the filter membrane of FIG. 25 within a 50 mL tube according to an exemplary embodiment of the disclosed subject matter.

FIG. 29 is an exploded-part view of an alternative exemplary embodiment of the disclosed subject matter.

FIGS. 30A-C are schematic diagrams of various stages of assembly of the components of FIG. 29.

FIGS. 31A-D are schematic diagrams of various stages of filtration of the embodiment of FIG. 30C in accordance with the disclosed subject matter.

FIG. 32 is an exploded-part view of a container for storage of the filter membrane according to an exemplary embodiment of the disclosed subject matter.

FIGS. 33A-D are schematic diagrams of various stages of processing of the filter membrane of FIG. 32 in accordance with the disclosed subject matter.

FIG. 34 is a cross-sectional view of the assembled container for storage of FIG. 32.

FIGS. 35A-D are schematic diagrams of various stages of embedding of the filter membrane of FIG. 32 in accordance with the disclosed subject matter.

FIGS. 36A-F are schematic diagrams of various stages of sectioning of the filter membrane of FIG. 32 in accordance with the disclosed subject matter.

FIGS. 37A-B are schematic zoom-in views of alternative clamping cap embodiments of the disclosed subject matter.

FIG. 38 is a schematic zoom-in view of alternative clamping cap embodiment of the disclosed subject matter.

FIG. 39A-B are schematic zoom-in views of alternative clamping cap embodiments of the disclosed subject matter.

FIG. 40 is a schematic zoom-in view of alternative tube embodiment of the disclosed subject matter.

FIG. 41 is an exploded-part schematic view of an embodiment of the post-filtration cap in accordance with the disclosed subject matter.

FIGS. 42A-B are schematic views of the post-filtration cap of FIG. 41.

FIGS. 43A-B are schematic view of alternative post-filtration cap embodiment of the disclosed subject matter.

FIGS. 46 and 46A are an assembled and cross sectional view of the assembled filter membrane and cover of FIG. 45.

FIGS. 49-51A are alternative embodiments of the filter membrane in accordance with the disclosed subject matter.

FIG. 52 is another embodiment of the filtration assembly in accordance with the disclosed subject matter.

FIG. 53-53B are cross sectional views of the embodiment of FIG. 52.

FIG. 54 is a schematic representation of a clamp component in accordance with the disclosed subject matter.

FIG. 55-56A are additional embodiments of the filtration assembly in accordance with the disclosed subject matter.

FIG. 57-58 are additional embodiments of the cover member in accordance with the disclosed subject matter.

FIG. 59 is an additional embodiment of the filtration assembly in accordance with the disclosed subject matter.

DETAILED DESCRIPTION OF SUBJECT MATTER

Reference will now be made in detail to select embodiments of the disclosed subject matter, examples of which are illustrated in the accompanying drawing. The method and corresponding steps of the disclosed subject matter will be described in conjunction with the detailed description of the system.

In accordance with the various embodiments of the disclosed subject matter, as summarized above and as described in further detail below, there is provided an apparatus for collecting and separating a liquid component from a cellular, or solid particle component, of a biological sample. While an exemplary embodiment disclosed herein includes fine needle aspiration, the apparatus and method of the disclosed subject matter is not limited to this exemplary embodiment and will be understood by an artisan of ordinary skill to be operable for collection and separation of any bodily fluids or specimens. In an exemplary embodiment, a disposable cell block apparatus and a method for using the apparatus, e.g., for tumor diagnosis, benign diagnosis, and other ancillary tests including research and development analyses, is provided. As used herein, the term "cell block" refers to a concentration of cells or solid particles from a biological sample, which is embedded in a medium, such as but not limited to paraffin wax. Thin sections from the medium with embedded cells are sliced or sectioned from the filter membrane of the cell block for mounting on a glass slide for analysis on a microscope or sliced from the cell block for other analyses. For example, visualization of the cells and the extracellular environment can provide information to determine whether the tissue collected is benign or malignant. Alternatively, the slices provide cellular material (DNA, RNA, proteins) for microcellular analysis. Although particular embodiments disclosed herein may focus on collection of the tissue or solid particle component in a biological sample for further diagnostics/testing, it will be understood by one of ordinary skill in the art that the disclosed apparatus and method is equally applicable for applications in which the fluid component of the biological sample is to be the subject of further diagnostics/testing.

Figure 1:
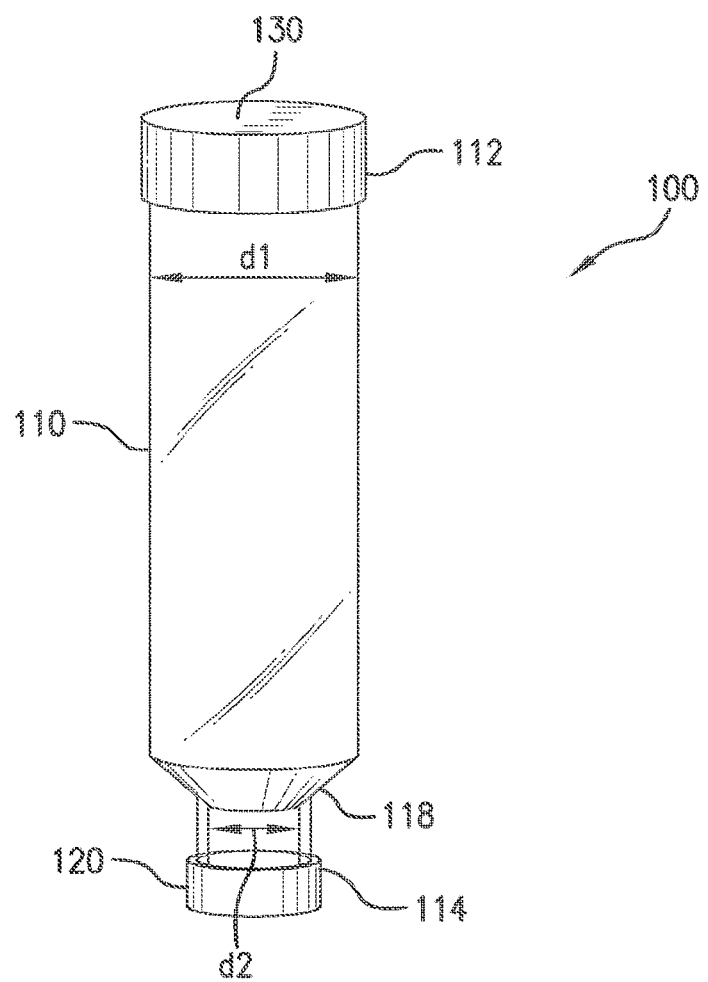
FIG. 1 is a schematic diagram showing an exemplary embodiment of the disclosed subject matter.

In one exemplary embodiment, the apparatus is configured as a cell block apparatus 100 is shown schematically in FIG. 1. Cell block apparatus 100 includes an elongate tubular body 110 and a filter assembly 120. The elongate tubular body 110 has a proximal end 112 and a distal end 114. In some embodiments, the elongate tubular body 110 has a first diameter (d1) at the proximal end and a second diameter (d2) at the distal end, wherein the second diameter is smaller than the first diameter. A section 118 disposed between the proximal end 112 and the distal end 114 of the elongate tubular body 110, has a decreasing diameter along a length thereof to define a generally conical distal section of the elongate tubular member 110. In some embodiments, a less gradual taper can be provided such that the elongate tubular body includes a step or abrupt restriction in diameter at 118. Various suitable volumes are available for elongate tubular body 110. For purpose of illustration and not limitation, suitable volumes include between about 15 ml to about 50 ml, or any other size that fits into a centrifuge, standard or otherwise. However, it will be understood by one of ordinary skill in the art that alternative sizes are within the scope of the disclosed subject matter. The elongate tubular body is sized to fit within a conventional centrifuge. In this manner, the cell block apparatus can receive the biological sample, for example, from a needle housing the biological sample obtained by fine needle aspiration techniques, and be disposed in the centrifuge for separation of the cells in the biological sample from any liquid to isolate and consolidate the cells into a concentrated pellet by centrifugation. Using the same unit for receiving the biological sample and separating the biological sample into component parts reduces the loss of sample size and reduces risk of contamination due to exchange between multiple components. In some embodiments, the elongate tubular body is suitable for relative centrifugal forces of between about 1,200 to about 16,000 RCF. For example, 12,000 RCF, 1,200 RCF, 16,000 RCF, 2,000 RCF, 9,400 RCF, 7,500 RCF. For further illustration in one embodiment, the elongate tubular member has a volume of 15 ml, and is suitable for centrifugation at 1,200 RCF or 12,000 RCF. In other embodiments, for example, the elongate tubular member has a volume of 50 ml and is suitable for centrifugation at 16,000 RCF or 2,000 RCF or 9,400 RCF. The elongate tubular body of the device can be formed of various materials and in particular various polymers, for example, polypropylene and/or polystyrene. Further, the materials used for the elongate tubular body, filter assembly, or compressive cover, which is described below, can be biodegradable materials.

Figure 2:
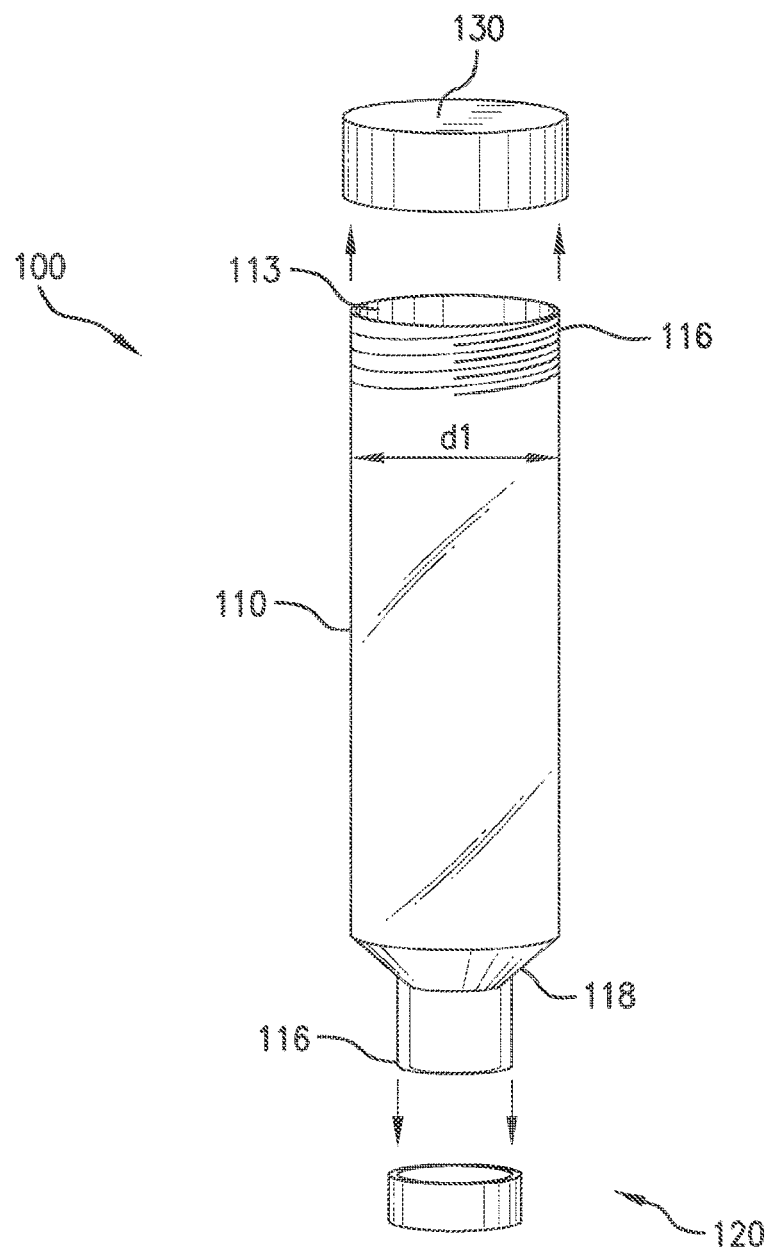
FIG. 2 is a schematic diagram showing an exploded view of the disclosed subject matter of FIG. 1.

Referring to FIG. 2, the elongate tubular body 110 defines an opening 113 at the proximal end of the body. In some embodiments, the opening 113 is closed by a lid 130. The lid can be configured with thread (not shown) to engage threads 116 disposed on a proximal section of the elongate tubular body 110. However, other suitable methods and features can be used to engage the lid 130 and elongate tubular body 110, such as interference fit or other methods of engagement, as would be appreciated by one of ordinary skill in the art. In one embodiment, the lid can be a stopper formed from a self sealing or resealable material. In this regard, the lid 130 is puncturable by a needle allowing transfer of the biological sample from the needle to the interior of the elongate tubular body. After deposit of the biological sample and removal of the needle from the lid 130, the material self-seals the puncture created by the needle entry. In the exemplary embodiment illustrated in FIG. 2, at the distal most end 116 of the elongate tubular body 110 the structure is configured to permit the filter assembly 120 to engage. In one embodiment, the material of the neck 116 has a thickened wall to allow the filter assembly 120 to securely engage the elongate tubular member 110. Further, the outer surface of the neck 116 can be configured with a thread or a plurality of threads to permit the base member 124 to securely engage the elongate tubular body 110.

In some embodiments, the elongate tubular body is preloaded with a fixative. A "fixative" as used herein refers to a compound, such as formalin, ethanol, methanol, RPMI, saline for preservation of the cells.

Figure 3:
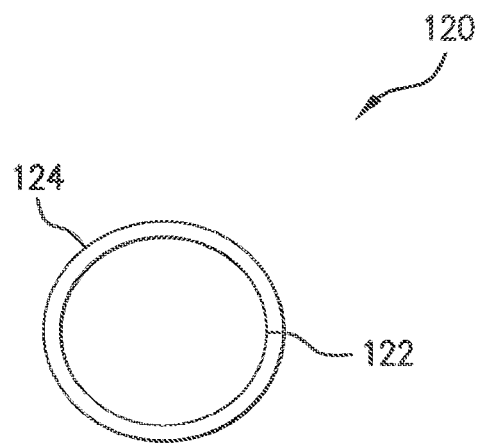
FIG. 3 is a schematic diagram of the filter assembly from a top view perspective including a filter membrane and a base member.
Figure 4:
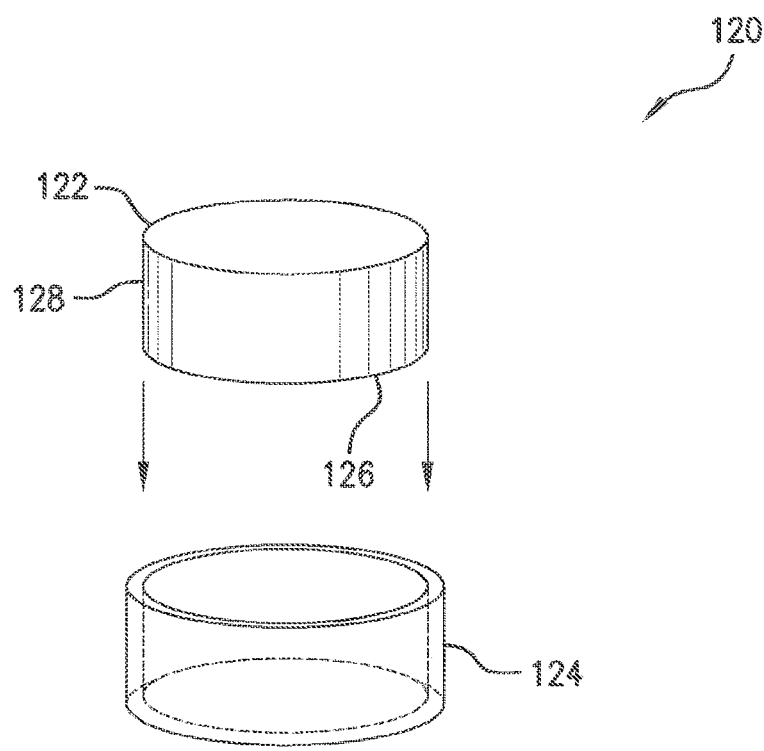
FIG. 4 is a schematic diagram of one embodiment of the filter assembly of the disclosed subject matter.

Referring to FIG. 3, a top view of a filter assembly 120 in accordance with the subject matter is provided. In an exemplary embodiment, the filter assembly 120 comprises a base member 124, such as a non-porous member, and a filter membrane 122 that is disposed within the body of the base member. Thus, in one embodiment, the filter assembly is removable. Additionally, the entire filter assembly, including filter membrane 122 and its border (or frame) is sectionable, i.e., capable of being cut or sliced into pieces or "sections" e.g., for mounting on a glass slide for analysis on a microscope or for other analyses such as microcellular analysis, e.g., DNA, RNA, and/or protein. As illustrated in FIG. 4, the filter membrane 122 is sized sufficiently smaller than the base member 124 so that it can slide into the interior space defined by the base member 124. In some embodiments, the filter membrane includes sidewalls formed of paraffin, paraform, plastic, rubber or foam. Referring back to the exemplary embodiment depicted in FIG. 1, the filter assembly 120 is associated, or coupled, with the distal end of the elongate tubular member. In this respect, the base member 124 can be configured with threads or some other engaging member to engage a distal portion of the elongate tubular body 110, and the filter membrane 122 member can be sized to engage the distal end of the elongate tubular member, for example, by an interference fit. The engagement of the filter membrane with the interior surface of the elongate tubular body provides a seal to prevent leakage around the periphery of the filter membrane. Consequently, any fluid within the distal portion of the elongate tubular body must first pass through, and be filtered, by the filter membrane. Thus, in this exemplary embodiment, the filter membrane 122 can be slidably received by the distal portion (e.g., neck) of the elongate member. The filter assembly 120 is detachable from the elongate tubular body. As described in detail below, the detached filter assembly 120 and its contents can be enclosed by a compressive cover 200 (as shown in FIG. 8).

The filter membrane 122 has a porosity sufficient to maintain the cells or cellular components from the biological sample while the liquid and fixative pass through. In some embodiments, the liquid is the fixative. However, in other embodiments, the liquid and fixative may be a mixture. For purpose of illustration and not limitation, in some embodiments the filter membrane 122 has pores between about 0.4 µm to about 5 µm. The pore density can be about $1\times10^8$ to about $6\times10^5$ pores/cm$^2$. Thus, in some embodiments, the filter membrane has a porosity of 5.0 µm and a pore density of $6\times10^5$ pores/cm2. In other embodiments, the filter membrane has a porosity of 5.0 µm and a pore density of $1\times10^8$. However, suitable porosity and pore density can be selected depending on the cells targeted for capture. In some embodiments, the filter membrane has a thickness of about 9 to about 100 µm, such as 17 µm. Although specific ranges are provided for exemplary purposes, it will be understood by one of ordinary skill in the art that alternative sizes are within the scope of the disclosed subject matter. Suitable materials can be used to from the filer membrane. For example, in one embodiment the filter membrane is formed from polyethylene terephthalate.

Figure 5:
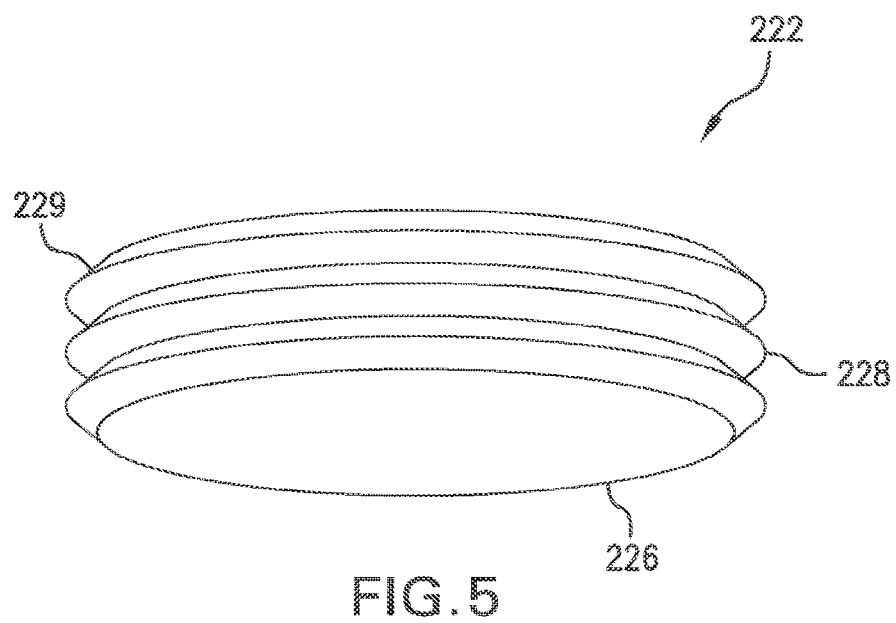
FIG. 5 is a schematic diagram of another exemplary embodiment of the filter membrane of the disclosed subject matter.
Figure 7:
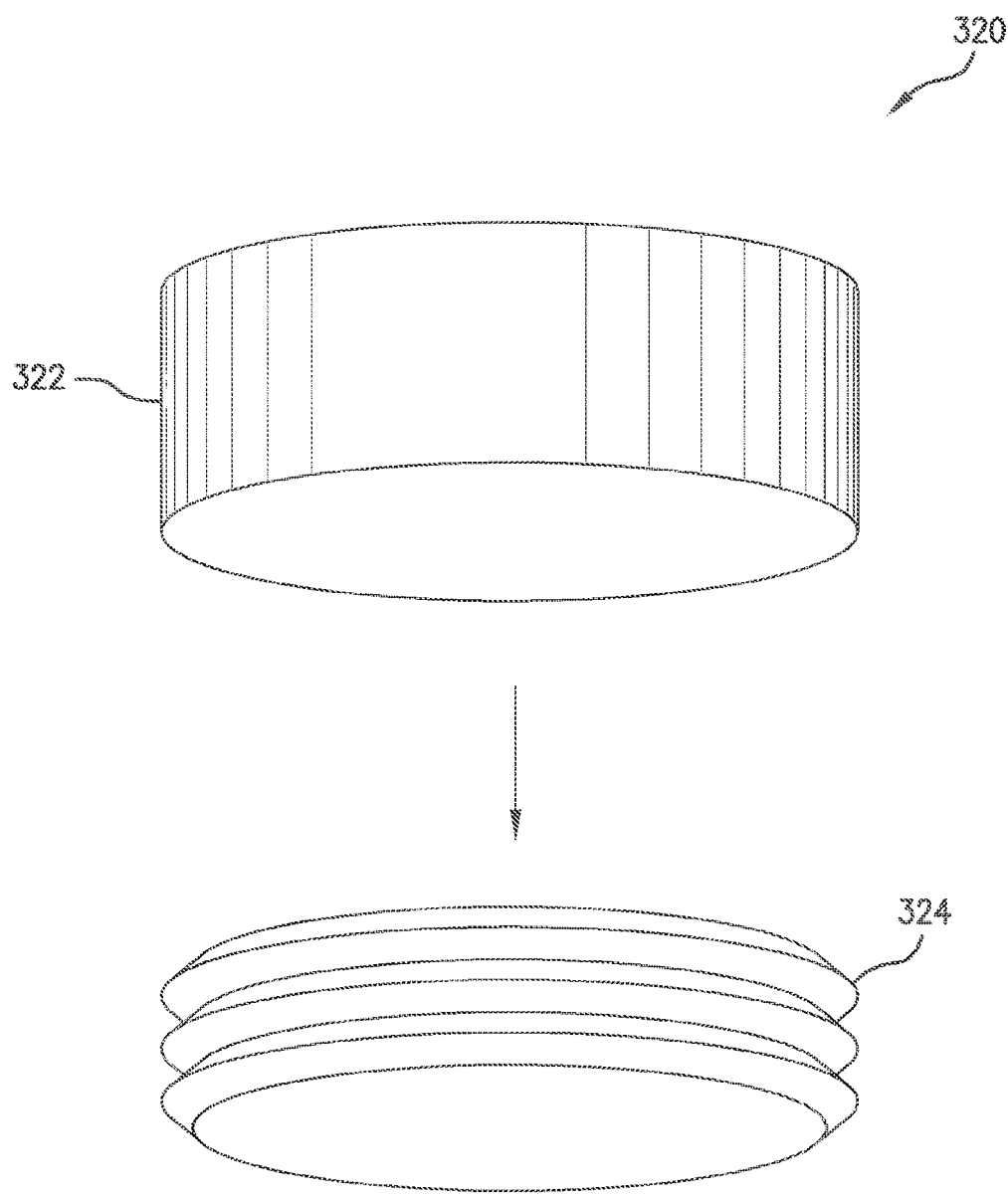
FIG. 7 is a schematic diagram of another exemplary embodiment of the filter assembly of the disclosed subject matter, including a filter membrane and a bellowed base member.

The filter membrane 122, as illustrated in FIG. 4, has a planar bottom surface 126 and an upwardly extending wall 128 around the periphery of the planar bottom surface 126. The upwardly extending wall can, in some embodiments, have a planar surface. Alternatively, as schematically shown in FIG. 5, the filter membrane 222 can include an upwardly extending wall 228 having one or a plurality of bellows 229 or a plurality of threads. In an alternative embodiment, as illustrated schematically in FIG. 7, the filter assembly 320 can include base member 324 having an upwardly extending wall with bellows and a filter membrane 322 having a planar side wall. In some embodiments, the bellows provide the capability of the base member or the filter membrane to adjust to sample size. The bellowed side wall compresses the cells into a tablet, which further facilitates an even distribution of cells. For example, in some instances, the smaller the sample, the greater the bellows will expand to create a compact pellet. The filter membrane and the base member permit essential fluids for fixation and processing to enter the base member but do not allow the cells to pass through. Thus, the cells remain on the filter membrane.

While the filter assembly in the exemplary embodiments is depicted as two discrete members (i.e. a filter membrane and base member), alternative configurations (e.g., an integrally formed and unitary filter assembly) will be understood by artisans of ordinary skill to be within the scope of the disclosed subject matter.

The combination of cells can be embedded in paraffin and cut, within the filter assembly or separately, into slices for diagnosis and ancillary tests. In other words, the filter membrane's structural characteristics allow for a blade to slice through the membrane and base member without flaking or splintering such that no unwanted debris is produced that might contaminate or compromise the pellet retained within or on the membrane. Further, the filter assembly is of sufficient rigidity to maintain its form and orientation indicia (described in further detail below), yet is sufficiently malleable and flexible so as to avoid damaging the cutting blade.

In this manner, the presently disclosed subject matter provides for a method for preparing a cell block in which the filter assembly remains with the specimen throughout processing to eliminate the risk of particle loss and cross contamination that can occur during various procedural steps, which involved eight transfers under prior art techniques. Additionally, the disclosed subject matter provides a standardized technique for processing samples which allows for more consistency and accuracy to pathological evaluations. In some embodiments, the method comprises introducing a biological sample into a cell block apparatus described herein. The cell block apparatus containing the biological sample is disposed into a centrifuge to centrifuge the biological sample for a sufficient amount of time to separate the cells, or tissue, from the liquid component and form a pellet. Again, for purpose of illustration and not limitation, the biological sample can be centrifuged at relative centrifugal forces of between about 1,200 to about 16,000 RCF for about five to ten minutes, or longer as necessitated by the nature and amount of biological sample collected. Although specific ranges are provided for exemplary purposes, it will be understood by one of ordinary skill in the art that alternative centrifuge times are within the scope of the disclosed subject matter.

The pellet is then processed, for example, in a cassette though any alternative suitable housing can be employed. The cassette is placed in formalin and into a tissue processor for processing through several steps (including dehydration to remove any aqueous solutions, then clearing of dehydrant, and finally infiltration by an embedding agent, such as paraffin). The processing time of the cellular pellet varies upon the tissue processors. In one embodiment, the processing time is less than about three hours. Then the processed pellet is embedded into a medium to form a cell block. The medium, can be for example, paraffin, paraform, or the like. Various materials can be used for the embedding step.

In accordance with another aspect of the disclosed subject matter, multiple cell blocks can be formed simultaneously via batch processing in under about three hours. In such batch processing applications, a plurality of cell block apparatuses (each including an elongate tubular body having an interior space) is associated with a respective detachable filter assembly disposed in communication with the interior space of the elongate tubular body. As described above, in some embodiments the filter assembly includes a base member configured to engage the distal end of the elongate tubular body, and a membrane having a porosity of between about 0.4 µm to about 10.0 µm. Although an exemplary range is provided for illustrative purposes, it will be understood by one of ordinary skill in the art that alternative sizes are within the scope of the disclosed subject matter. Multiple biological samples, same or different, can be introduced into the cell block apparatuses. The elongate tubular bodies can be interconnected or configured as discrete units. The elongate tubular bodies are each sized sufficiently to fit into a centrifuge device configured with a plurality of receptacles to receive the plurality of elongate tubular bodies of the cell block apparatuses. Upon completion of the centrifuge cycle, the biological samples in each cell block apparatus forms a cellular pellet ready for individual processing or embedding into a plurality of cell blocks. Accordingly, the method disclosed herein can achieve an array of cell blocks.

Figure 6:
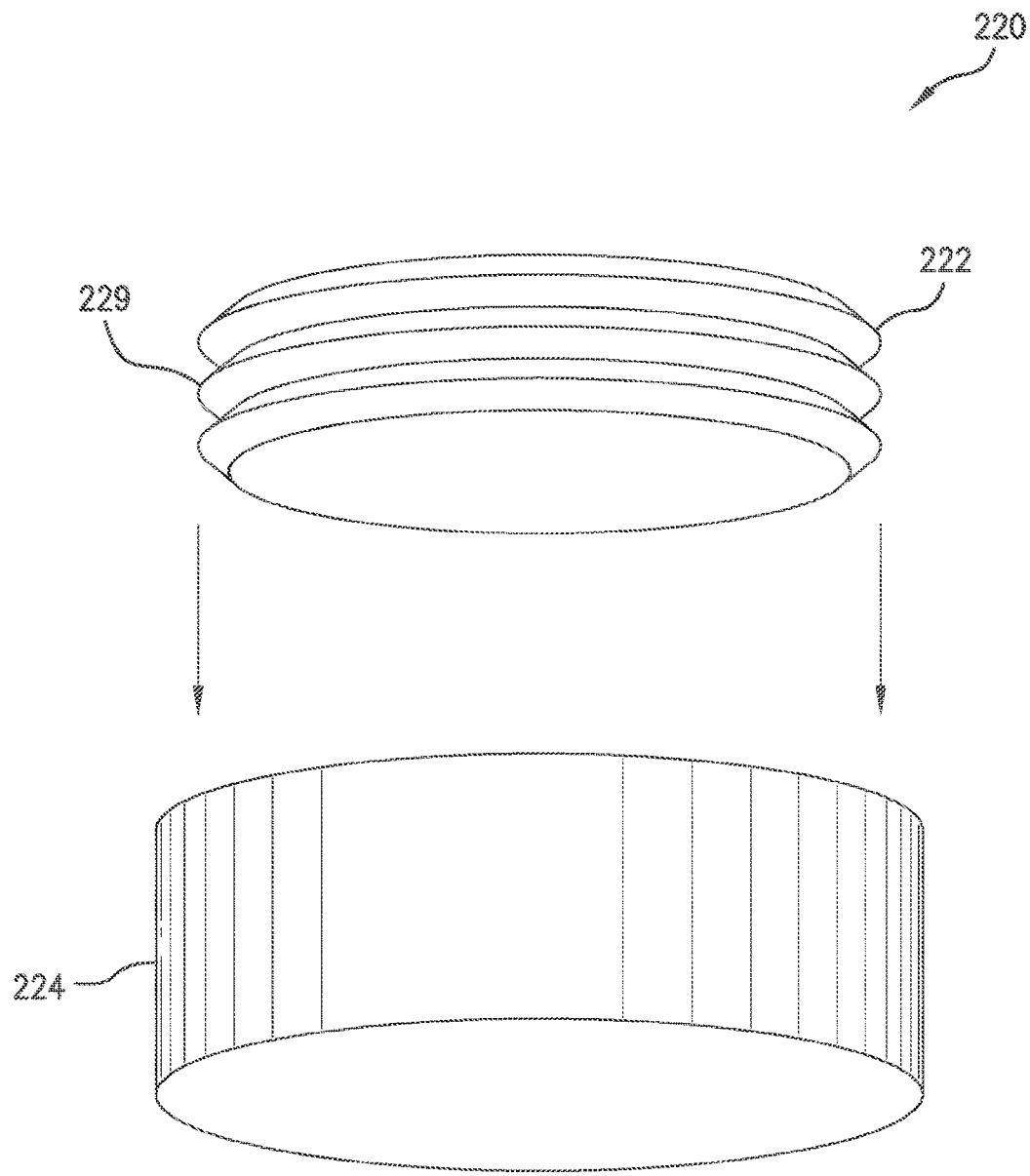
FIG. 6 is a schematic diagram of an exemplary embodiment of the filter assembly of the disclosed subject matter, including a bellowed filter membrane of FIG. 5 and base member.

In accordance with another aspect of the subject matter, the apparatus and system disclosed herein can be configured as a kit, or collection of discrete components designed to function as a unit. The kit includes a needle, such as but not limited to a fine aspiration needle, and a cell block apparatus described above. In some embodiments, the elongate tubular member is preloaded with a fixative. The kit may include a second, replaceable, filter assembly. Referring to FIG. 6, the second filter assembly 220 may include a base member 224 and a filter membrane 222 having a planar bottom surface and wall upwardly extending from the planar bottom surface of the filter membrane. The upwardly extending wall can include one or a plurality of bellows 229 or plurality of threads. In another embodiment, a kit is provided which provides one or more filter assemblies for samples that are not associated with a large quantity of liquid or blood. Tissue sealed in the filter assembly can then be placed in a container of formalin for clinicians performing FNAs or biopsies. In such instances, for example, the specimen does not need to be centrifuged in a tubular structure. Instead, it can be embedded in the filter assembly and undergo histology directly.

Figure 8A:
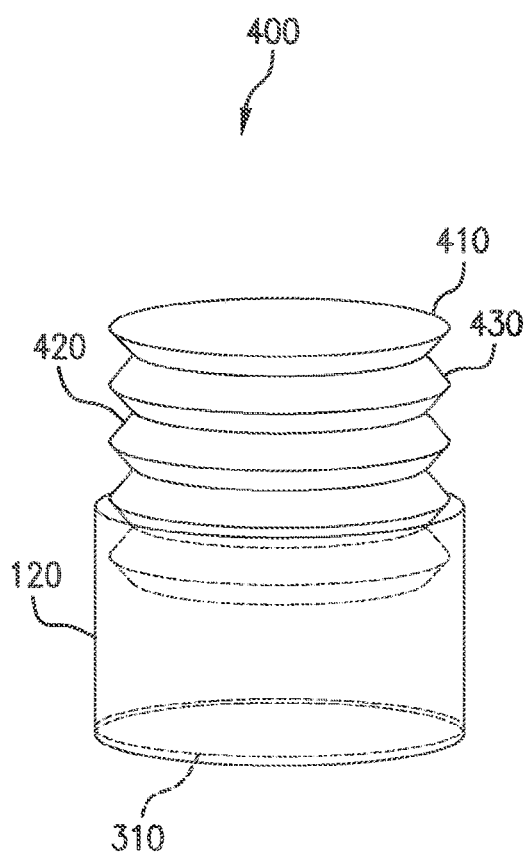
FIGS. 8A-D are schematic diagrams showing perspective views of a filter assembly and a compressive cover in accordance with the disclosed subject matter.
Figure 8B:
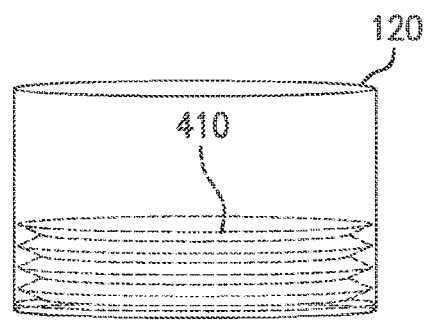
Figure 8C:
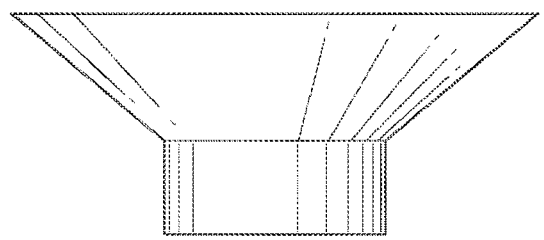
Figure 8D:

In yet another embodiment, as illustrated in FIGS. 8A and 8B, a filter assembly 120 is provided (as described above), which includes a compressive cover 400. As illustrated in FIG. 8A the filter assembly 120 can include a tissue sample 310. The compressive cover 400 is disposed within the filter assembly 120 and is able to close the filter assembly so that the contents are enclosed in a sealed manner. In this regard, the compressive cover can be configured with a planar top surface 410 that serves as a cap. The compressive cover 400 includes a planar bottom surface and a sidewall 412. As illustrated, the sidewall 412 can include a plurality of bellows 430, which can contract and expand. When in a contracted state (shown in FIG. 8B), a compressive force is exerted on the sample 310 contained within the filter assembly 120. Additionally or alternatively to the structural features described above which facilitate the generation of compressive forces, the cover can be formed of elastomeric material with innate compressive and expansive properties to enhance the compressive force exerted on the collected sample and filter membrane. The application of pressure to the sample 310 concentrates and constrains the sample. Additionally, the compressive cover facilitates an even distribution of cells and also helps the paraffin to penetrate the sample 310 to provide improved embedding of the cells of the tissue sample. Further, the compressive cover 400 serves to close the filter assembly from the external environment, thereby preserving the integrity of the collected tissue sample.

The compressive cover can have a planar surface formed from the same filter membrane material as that on the filter assembly. For example, in one embodiment, the compressive cover is lined by a filter membrane, which can be similar in pore size, thickness and density as the filter membrane 122 of the filter assembly 120. In another example, the compressive cover has a planar surface having a porosity of between about 0.4 µm to about 10.0 µm. Although an exemplary range is provided for illustrative purposes, it will be understood by one of ordinary skill in the art that alternative sizes are within the scope of the disclosed subject matter. The use of a compressive cover is advantageous in that it eliminates the need for more complex equipment and processes (e.g., hydraulic, vacuum and pneumatic regulators) to condense the tissue, remove excess liquid, and contain all cells.

Although FIGS. 8A-B depict generally circular compressive covers, alternative geometries such as a bowl shape (FIG. 8C) or elliptical-disc shape (FIG. 8D) can be employed if so desired. Similarly, alternative embodiments can include covers with non-planar bottom or top surfaces such that the cover can impart a pattern or non-uniform distribution of the collected sample, as well as covers having different diameters than the filter membrane. Also, the covers can include a retention mechanism (e.g., latch, tongue-groove coupling, etc.) for engagement with a corresponding structure on the filter assembly to lock or retain the sample on the filter membrane. Such an enclosure is advantageous in preventing debris from contaminating the collected sample, as well as facilitating storage and/or transport of the collected sample, if so desired.

The filter assembly 120 and compressive cover 400 together, for example, can be used for non-FNA specimens, such as biopsies. For example, the specimen can be placed directly in the filter assembly at the time the clinician removes the tissue from the patient (rather than placing loose piece(s) of tissue in jar of formalin to be handled by pathology laboratory personnel thereafter). Such application is advantageous in that it: (1) eliminates the chance of cross contamination which is possible with transferring and handling tissue multiple times; (2) eliminates the loss of minute pieces of tissue with multiple transfers; and (3) prevents leaving a specimen behind in a formalin jar, for example, because the specimen was inadvertently undetected. Typically, tissue samples are transferred from different media and/or containers several times before being ready for cutting for microscopic examination. The filter assembly and compressive cover disclosed herein serve to overcome the disadvantages of such procedures.

In another exemplary embodiment, the elongate tubular body can be configured of multiple pieces 510 $a$, 510 $b$ with a filter membrane 522 can be disposed between pieces 510$a$ and 510$b$, e.g., at the midpoint of the assembled tubular body, as depicted in FIGS. 9A-B. It is to be understood that although specific reference may be made only to the filter membrane in the exemplary embodiments disclosed below, it is within the scope of the disclosed subject matter to include a cover and base member with the filter membrane, if so desired. In this exemplary embodiment of FIGS. 9A-B, the filter membrane 522 is clamped between the two tubular portions 510$a$ and 510$b$ to capture particulates while liquid passes from 510$a$ to 510$b$ during centrifuging. The lower tubular member 510 $b$ can be configured with a lip or recess proximate on its upper end to receive the filter membrane 522 therein. Alternatively, the upper tubular member 510 $a$ can be configured with a support member, such as shelf or flange (described in further detail below), which receives the filter membrane 522 therein. Locating the filter membrane at the midpoint of the tubular body is advantageous in that such a configuration results in the reservoir disposed above the filter membrane to be of equivalent size as the reservoir below the filter membrane, and therefore equivalent amounts of fluid can be contained within each reservoir. However, the filter membrane can be disposed at alternative locations closer to the top or bottom of either tubular portion 510$a$, 510$b$ is within the scope of the disclosed subject matter.

The elongate tubular pieces 510$a$, 510$b$ can be attached, e.g., by via an interference fit or a threaded engagement between the respective inner and outer sidewalls. Although the exemplary embodiment depicted in FIGS. 9A-B depict the upper tubular member 510$a$ as the male component and the lower tubular member 510B as the female component, these configurations can be reversed, as so desired. Additionally, or alternatively, the tubular members can be formed with an equivalent inner and outer diameters, and coupled by any suitable device, e.g., magnets.

Figure 9C:
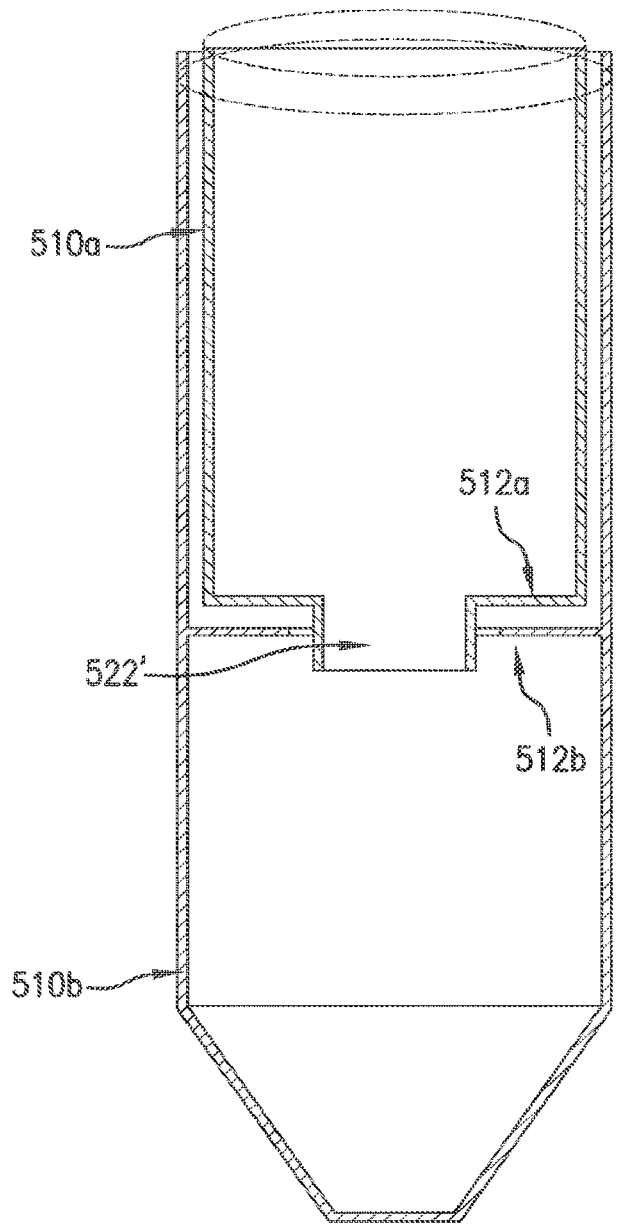
FIG. 9C is cross-sectional view of an alternative exemplary embodiment of the disclosed subject matter.

In another exemplary embodiment, the tube pieces 510$a$, 510$b$ can be configured such that one of the pieces is received, at least partially, in a telescoping manner within the other as shown in FIG. 9C. In the embodiment illustrated in FIG. 9C, the upper tube 510$a$ can have a bottom portion with a platform for the filter assembly that would fit at 522' and a circumscribing shelf or lip 512$a$ configured to rest against an inwardly protruding lip or shelf 512$b$ formed in the lower tube portion 510$b$. Additionally or alternatively, the inwardly protruding shelf 512$a$ can also receive the filter membrane. Further, the dimensions of the protruding shelves 512$a$, 512$b$ can vary both in terms of the cross-sectional thickness as well as the distance the lips radially protrude so as to accommodate filter membranes of varying sizes. The elongate tubular pieces 510$a$, 510$b$ can be attached via an interference fit, a threaded engagement between the respective inner and outer sidewalls, or via mating engagement between shelves 512$a$ and 512$b$.

Figure 9D:
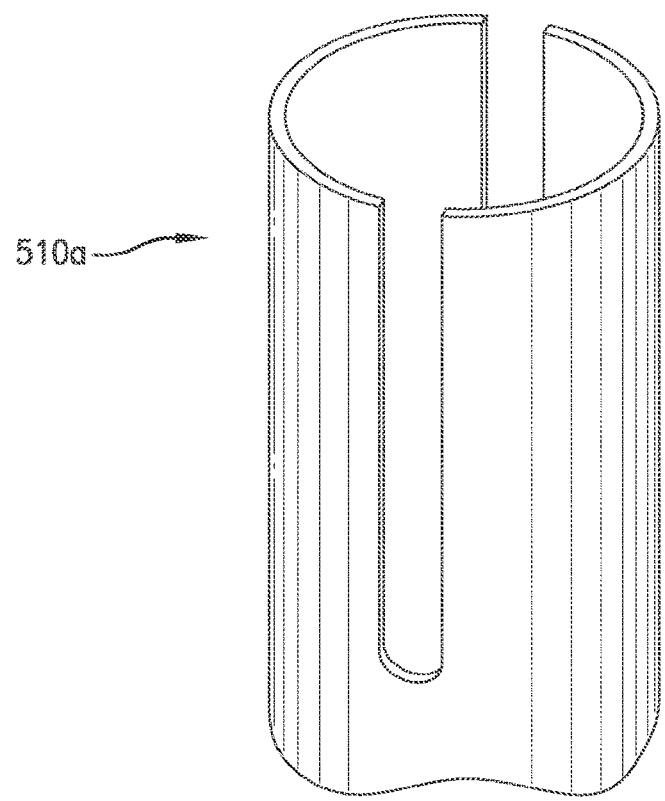
FIG. 9D is schematic diagram of a tubular member m accordance with the embodiment of FIG. 9C.

In some embodiments comprising two elongate tubular members, the inner tubular member 510$a$ can be formed with a slot or channel formed in the sidewall which extends along the longitudinal axis of the tubular member, as shown in FIG. 9D. This slot is sized to receive the filter membrane and allows for rapid removal of the filter membrane after the centrifuge process, without the need to disassemble the two elongate tubular members. Although the exemplary embodiment of FIG. 9D depicts vertical slots, alternative designs (such as a staggered or tortious path) are within the scope of the disclosed subject matter. Such tortious path designs can be advantageous in requiring deliberate and careful removal of the filter membrane, thereby preventing accidental removal or dislodgment of the filter membrane after the centrifuging process.

Figure 10A:
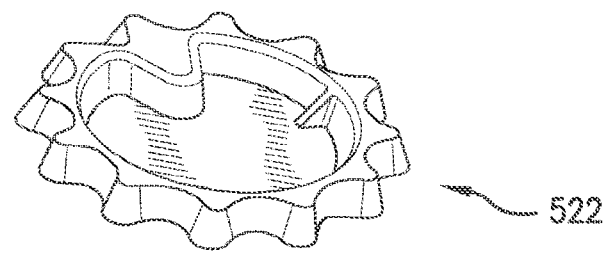
FIGS. 10A-H are schematic diagrams of another embodiment of the filter membrane of the disclosed subject matter.
Figure 10B:
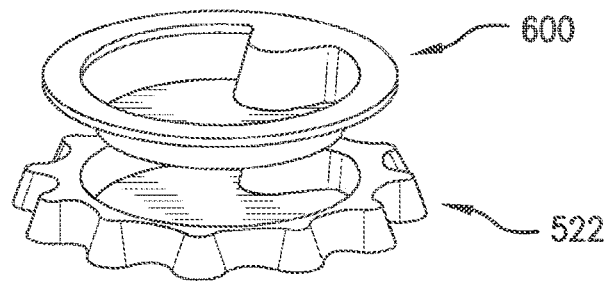
Figure 10C:
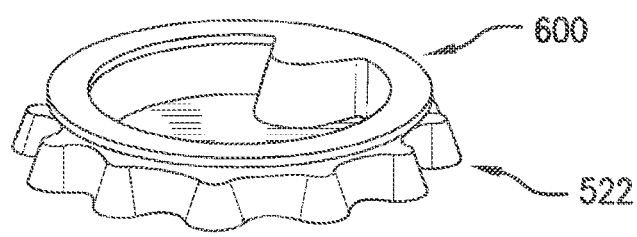
Figure 10D:
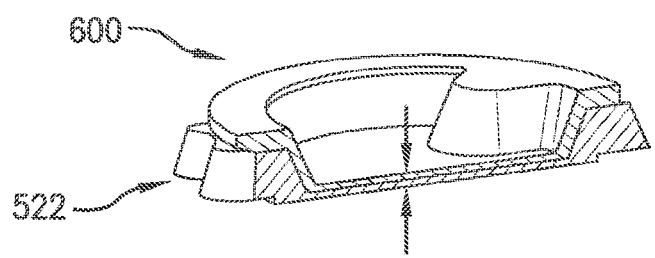

As previously described above with respect to FIGS. 8A-D, some embodiments of the disclosed subject matter can employ a compressive cover or cap to facilitate the concentration and isolation of the collected sample on the filter membrane. For example, the filter membrane 522 of FIG. 10A can be configured to receive a cover 600 which matingly engages the filter membrane 522 as shown in FIGS. 10B-D. As indicated by the arrows depicted in FIG. 10D, the cover 600 can apply a compressive force to concentrate and constrain the particulate for subsequent steps, such as dehydration, clearing, infiltration, etc. The compressive force exerted by the cover 600 can be supplied by the technician or by an external device (not shown) such as a spring-loaded plunger.

Figure 11A:
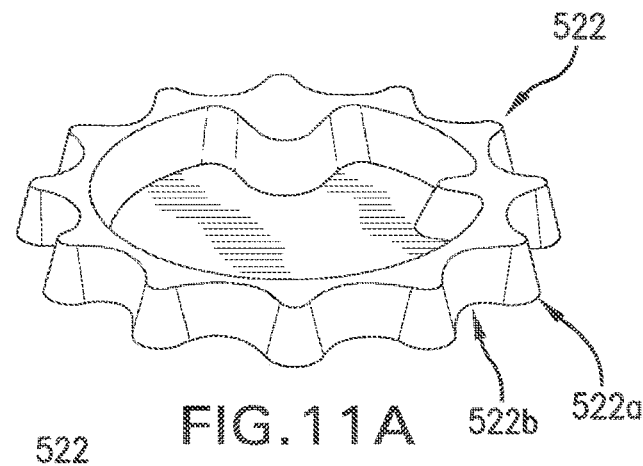
FIGS. 11A-C are schematic diagrams of another embodiment of the filter membrane of the disclosed subject matter.
Figure 11B:
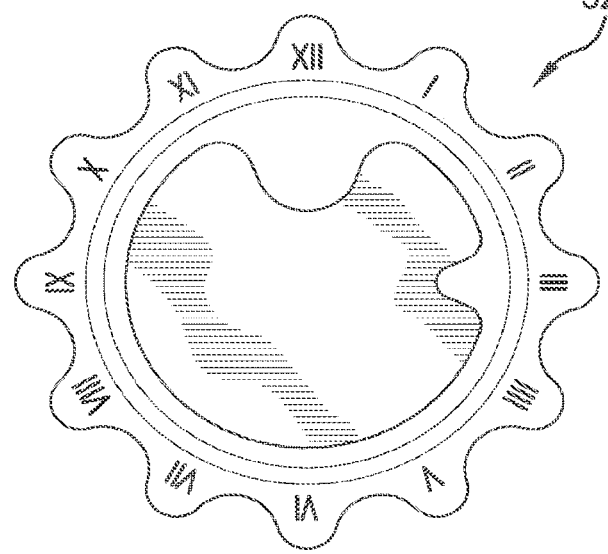
Figure 11C:
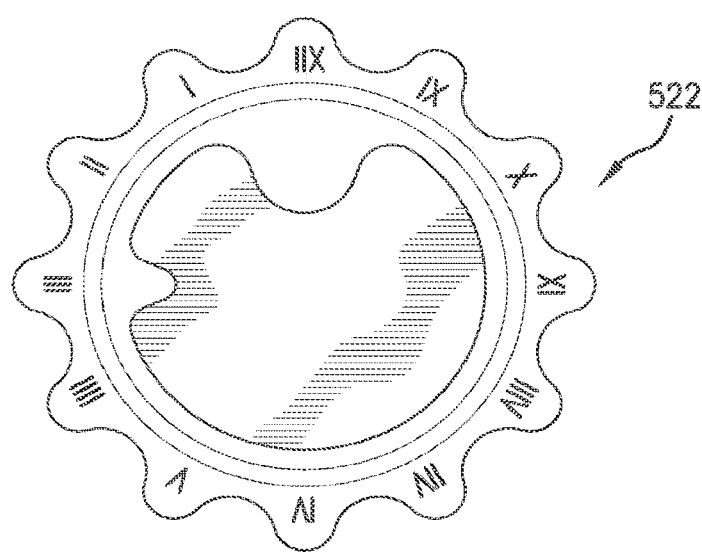
Figure 11D:
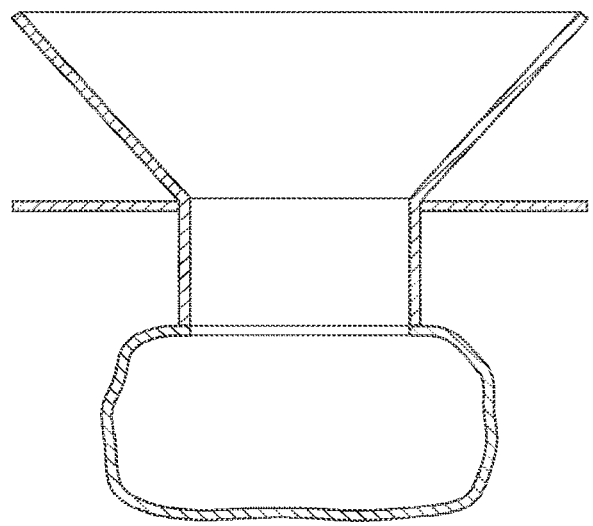
FIG. 11D is a cross-sectional view of another embodiment of the filter membrane of the disclosed subject matter.

In accordance with an aspect of the presently disclosed subject matter, the filter membrane 522 includes alignment features illustrated in the exemplary embodiment as Roman numeral indicia, as shown in FIGS. 11B-C. These indicia allow users to easily and precisely reference a specific region of interest (e.g., location "III", or the "three-o'clock position"). Additionally, the indicia allow for different slices of the filter membrane to be oriented as so desired with respect to each other, as well as evidencing whether the filter membrane 522 is flipped or inverted. The filter membrane 522 can be formed with alternating peaks 522$a$ and valleys 522$b$ around its circumference, as shown in FIG. 11A, to increase the surface area and provide greater stability and reliability during both the centrifuge step as well as the subsequent sectioning (i.e. cutting). In addition to this indicia, the border (or frame) of the filter membrane can be formed with a greater thickness than the porous filter portion, and serve as a gasket which forms a seal with the interior surface of the tubular body. Further, this border portion can be formed of opaque material which further serves as a visual aid to easily identify particular areas of interest in the sample collected on the inner porous material. Furthermore, this border portion of the filter membrane can be formed of a porous material, e.g. open cell foam or foam rubber, which allows the cutting blade to easily slice through the filter membrane without excessive force, thereby eliminating any undesired buckling of the filter membrane, damage to the blade, or splintering or flaking of the filter membrane. Additionally, the filter membrane can be formed separately from the remainder of the filter assembly (e.g., the porous filter membrane which serves to separate the tissue(s), or cell block, from the collected sample of fluid/tissue can be distinct from the surrounding frame having the undulating structure and indicia as shown in FIG. 10A). The porous filter membrane can be attached to the surrounding structure via adhesive or ultrasonic welding.

Figure 10F:
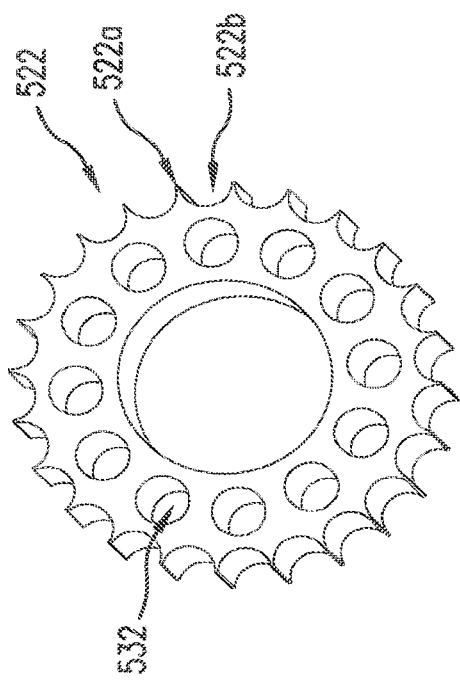
Figure 10H:
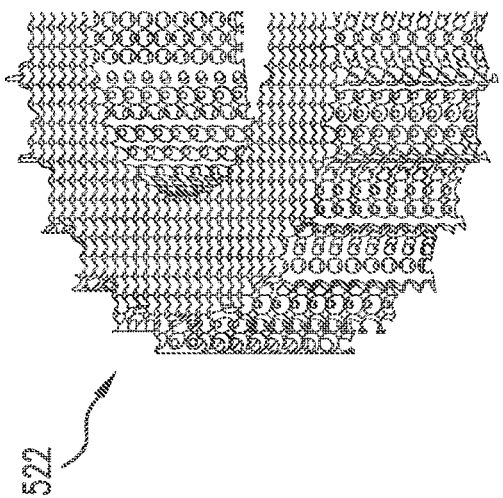
Figure 10E:
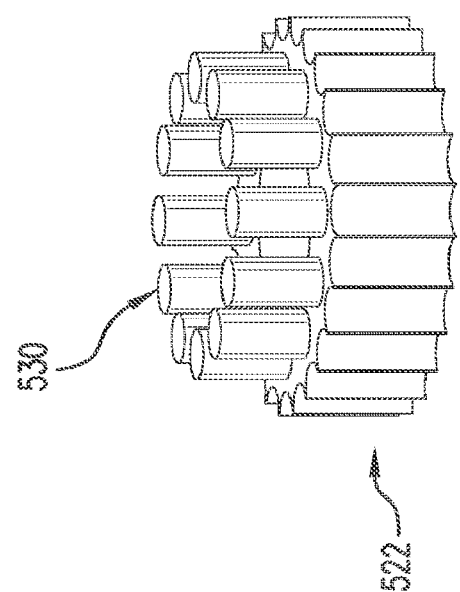
Figure 10G:
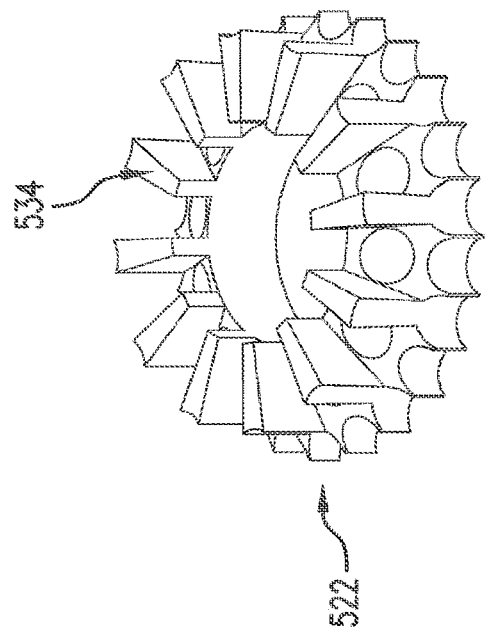

In further regards to the structure of the filter membrane (or assembly, if present), and as disclosed above, the increase in surface area provided by the peaks and valleys formed in the periphery of the filter membrane (or assembly, if present) facilitates integration with the embedding medium (e.g., wax) and improved anchoring of the filter membrane. The number of peaks and valleys can be varied as so desired, and in some embodiments the peaks and valleys are configured as obtuse rounded edges (FIGS. 10A-D), whereas in other embodiments the peaks and valleys are formed as acute apices (FIGS. 10E-F). Additionally or alternatively, the filter membrane 522 (or assembly, if present) can be formed recesses 532, as illustrated in FIGS. 10E-G, which similarly increase the surface area for engagement of the filter membrane with the embedding medium. In other embodiments the filter membrane can be formed with surface features, such as cylindrical posts 530 (FIG. 10E) or ribs 534 (FIG. 10G) which also increase the surface area for engagement with the embedding medium. Additionally or alternatively, as illustrated in FIG. 10H, the filter membrane can be formed as a porous member, e.g. foam, which permits the embedding medium to penetrate through and infiltrate the entire filter membrane and/or assembly. In each of these embodiments, the enhanced engagement and integration of the filter membrane with the wax results in a more reliable and consistent sectioning. Moreover, the various structural features described above (e.g. peaks/valleys, holes, ribs, porous foam) for increasing the surface area of the filter membrane also allow for a user to selectively orient the filter membrane during assembly, sectioning, and/or placing in a diagnostic apparatus (e.g. microscope).

Although the particular exemplary embodiments of the filter membrane shown in FIGS. 10-11C depict a generally circular filter membrane formed of a semi-rigid material, alternative configurations of filter membrane geometries and construction are within the scope of the disclosed subject matter. For example, the filter membrane can be configured as a flexible bag-like member, as shown in FIG. 11D. The bag-like filter membrane is made with a desired porosity, as described above, and provides an amorphous shape which allows the membrane to distort as needed under the forces generated during the centrifuge process, which can relieve some of the stresses that may be imparted on the other components of the apparatus when a rigid filter membrane is employed. Additionally, such a flexible bag-like filter embodiment allows for greater design flexibility in that the amorphous filter can accommodate differing volumes of cells. Furthermore, the amorphous bag-like structure effectively increases the surface area through which the biological sample passes, which in turn expedites the filtration process and minimizes the risk of clogging the filter membrane in applications of cellular specimens. The exemplary embodiment depicted in FIG. 11D illustrates a filter membrane which also includes structural reinforcement features, described in further detail below.

Figure 12A:
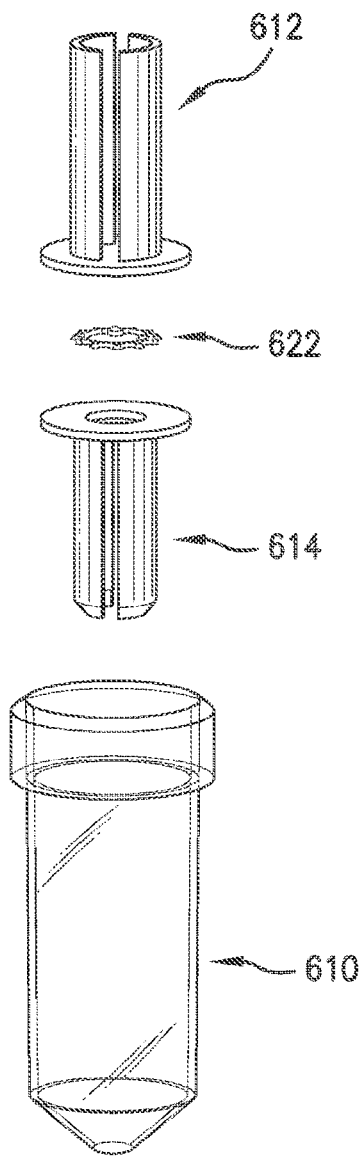
FIG. 12A is an exploded view of an alternative exemplary embodiment of the disclosed subject matter.
Figure 12B:
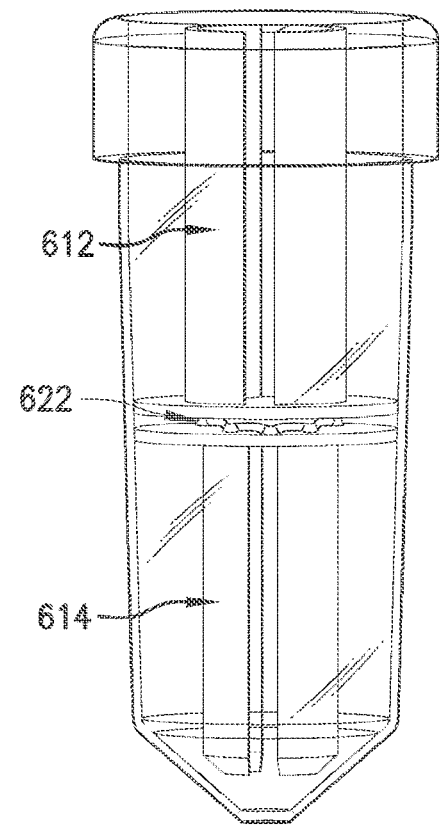
FIG. 12B is a schematic diagrams showing the assembled embodiment of FIG. 12A.

In an alternative embodiment, a singular elongate tubular body 610 can include sealing plungers 612 and 614 disposed therein, and a filter membrane 622 disposed between the plungers, as depicted in FIG. 12A-B. The plungers support the filter membrane 622 at a location suspended between the ends of the tubular body 610, e.g., at a midpoint of the tubular body 610, and have a radial flange circumscribing the plunger which seals off an upper and lower reservoir within the tubular body 610. This seal prohibits fluid transfer between reservoirs during centrifugation, thereby forcing all liquid to pass through the filter membrane 622. As described above, locating the filter membrane at the midpoint of the tubular body is advantageous in that it provides reservoirs of equivalent size and amounts of fluid contained therein. However, the plungers 612, 614 can be sized as so desired to position the filter membrane at any point along the tubular body 610.

Figure 13A:
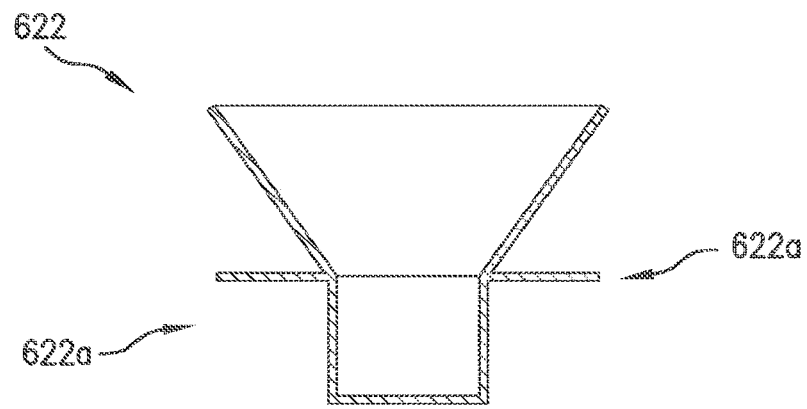
FIGS. 13A-D are cross-sectional diagrams of another embodiment of the filter membrane of the disclosed subject matter.
Figure 13B:
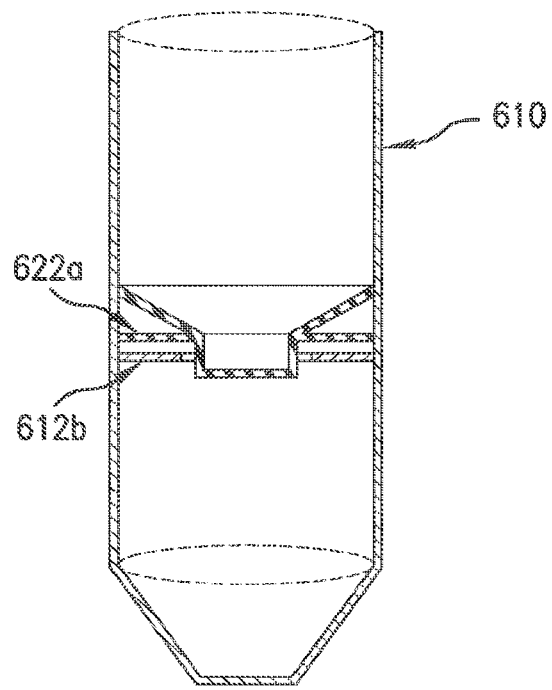
Figure 13C:
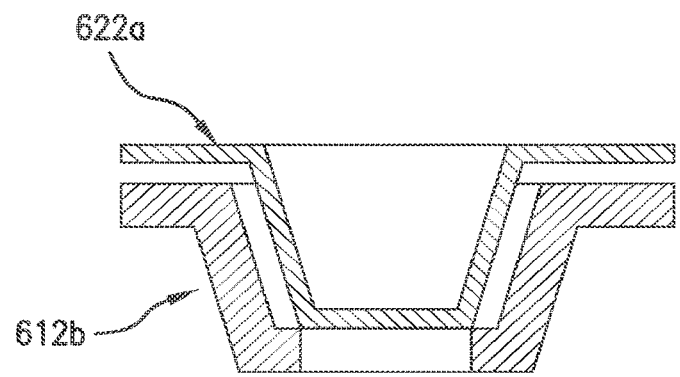

In some embodiments the filter membrane can include structural reinforcement features. In the exemplary embodiment shown in FIG. 13A, a bowl-like filter membrane 622 (shown in cross-sectional view) includes radially outwardly extending protrusions or shelves 622a that are sized to engage a corresponding shelf or lip in the elongate tube 610 which receives the filter membrane, as shown in FIG. 13B. These radially outwardly extending protrusions or shelves 622a strengthen the sidewalls of the filter membrane and absorb some of the forces generated during the centrifuge process. In some embodiments, the shelves 612b of the elongate tube member 610 are contoured to engage the filter membrane shelves 622a over a greater surface area (e.g., the sidewalls of the bowl-like filter membrane) as shown in FIG. 13C. This increased area of engagement between the filter membrane and the elongate tubular member provides additional support to the filter membrane during centrifuge process. Furthermore, the structural reinforcement features 622a and 612b allow for the filter membrane to be securely positioned within a single piece elongate tubular member 610. This can be advantageous in that it reduces the total number of parts as well as the assembly/disassembly steps required to carry out the method of the disclosed subject matter.

Figure 13D:
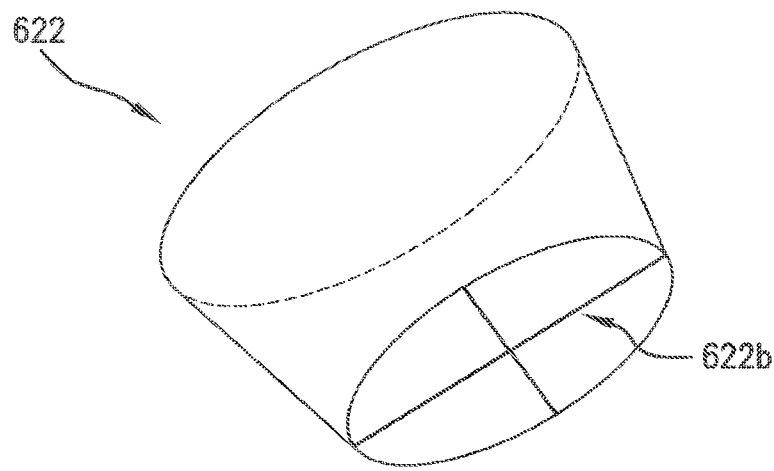

Additionally or alternatively, the structural reinforcement features can include struts 622b disposed at the bottom of the filter membrane which extend across the length, e.g., diameter, of the filter membrane 622, as shown in FIG. 13D. These struts 622b prevent the filter membrane from warping or breaking when exposed to forces associated with the centrifuge process. These structural reinforcement features disclosed herein can be formed integrally with the filter membrane, or alternatively formed as a separate insert that is positioned below the filter membrane.

Additionally, a handle (not shown) can be incorporated into the filter membrane which extends above the opening of the elongate tube member to allow the membrane to be easily removed. In this regard, the operator grasps the handle at a location which is spaced above the collected cell sample, thereby eliminating any risk of contamination or accidental loss of the sample. In some embodiments, the handle can extend radially outward through a slot formed in the tubular body, as described above and shown in FIG. 9D.

Figure 14A:
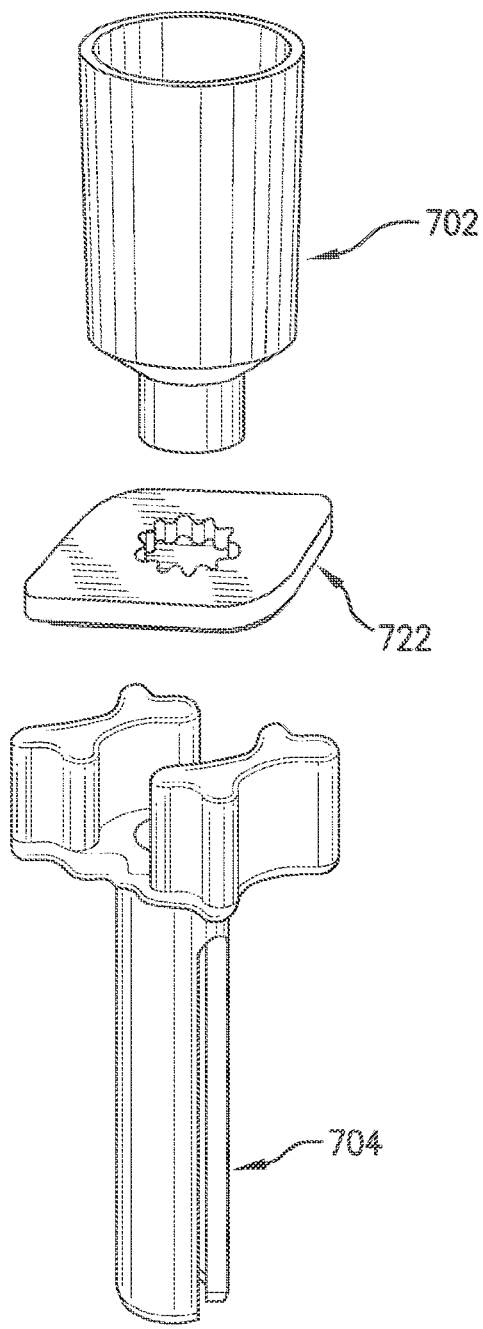
FIG. 14A is an exploded view of an alternative exemplary embodiment of the disclosed subject matter.
Figure 14B:
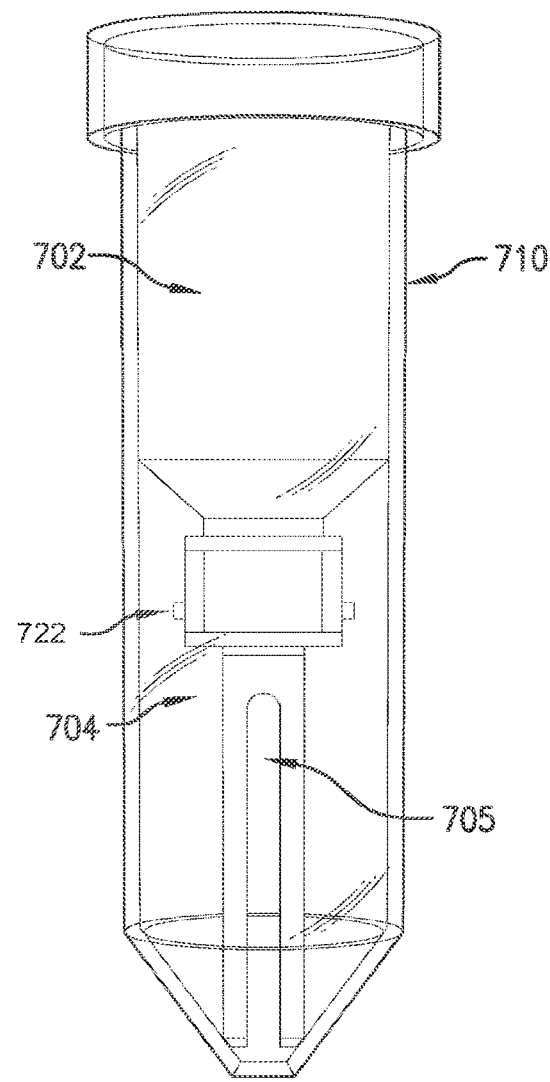
FIG. 14B is a schematic diagram showing the assembled embodiment of FIG. 14A.
Figure 14C:
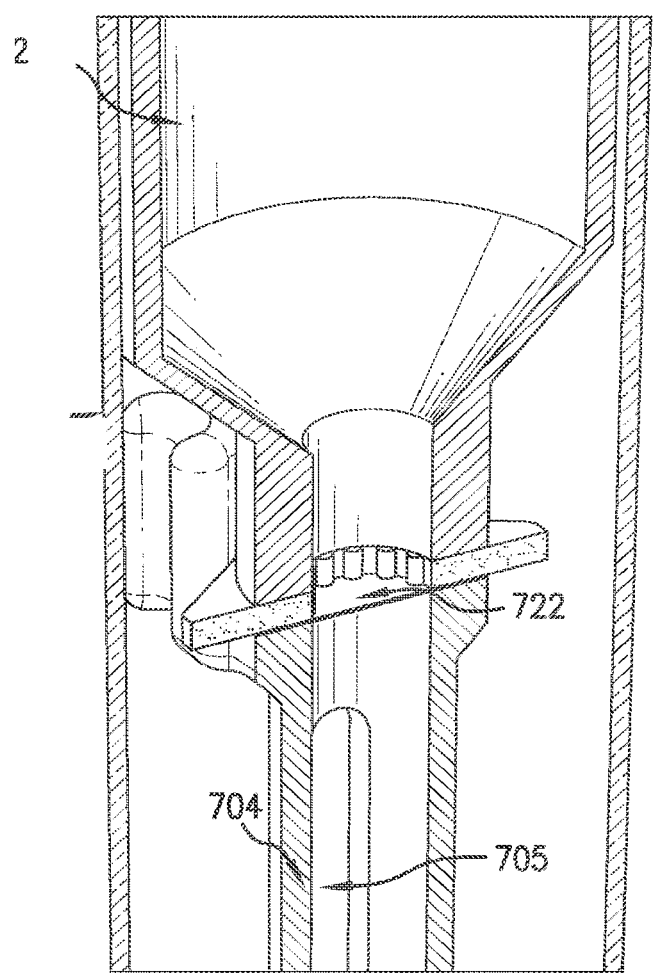
FIG. 14C is a cross-sectional view showing the assembled embodiment of FIG. 14B.

In an alternative exemplary embodiment, a sample loading chamber 702 and filter membrane 722 are disposed on a support post 704 and housed within a unitary elongate tubular body 710, as shown in FIGS. 14A-C. The support post 704 is disposed below the filter membrane and extends longitudinally to position the filter membrane 722 at a location suspended between the ends of the tube 710, e.g., at a midpoint of the tube 710. The filter membrane 722 can include a radially extending border portion, e.g., flange, which seals off an upper and lower reservoir within the elongate tubular member 710. This seal prohibits fluid transfer between reservoirs during centrifugation, thereby forcing all material to pass through the filter membrane. As described above, locating the filter membrane at the midpoint of the tube is advantageous in that such a configuration results in equivalent size reservoirs. However, alternative locations of the filter membrane are within the scope of the disclosed subject matter.

The support post 704 can include longitudinally extending slots or channels 705. These slots serve as passageways which allow for the liquid disposed below the filter membrane to freely move around within the lower reservoir formed during the centrifuge process to avoid localized pockets or cells of concentrated liquid. Additionally or alternatively, the slots can be configured as discontinuous local openings, e.g., circular apertures. An additional advantage of the embodiment depicted in FIGS. 14A-C is that it can be readily configured to fit existing centrifuge tubes, thus avoiding expensive or complex retrofit operations. In addition to allowing for passage of fluid, the slot 705 allows for deflection of the support post 704 to compensate and adjust for variances in length (e.g. due to manufacturing tolerances) of the various pieces upon assembly of the apparatus. That is, the components 702, 722, and 704 are positioned inside the tube 710 and compressed when the cap is attached at the top of the tube. The slot 705 provides a spring action which can bend to allow the filter membrane/assembly to be compressed for a range of height variations.

Figure 15:
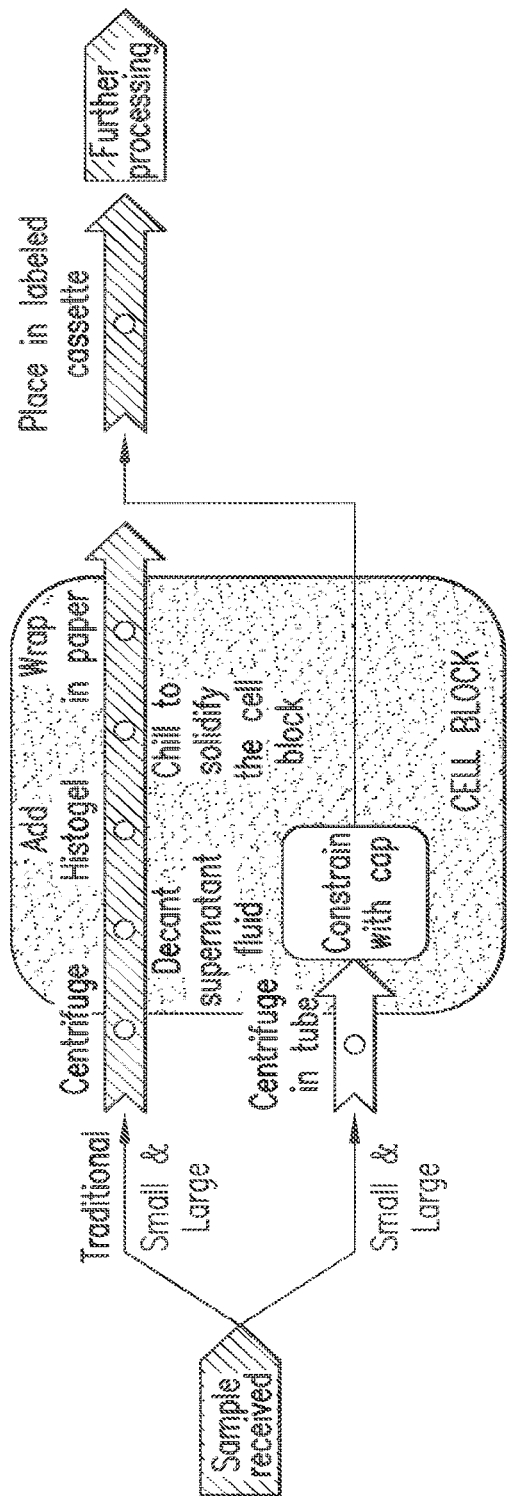
FIG. 15 is a flow diagram of the process of the disclosed subject matter.

In accordance with another aspect of the disclosed subject matter, the systems disclosed herein allow for an improved FNA processing protocol which reduces the number of steps of the presently disclosed subject matter (denoted by reference numeral 20) as compared to traditional prior art techniques (denoted by reference numeral 10), as shown in FIG. 15.

Figure 16:
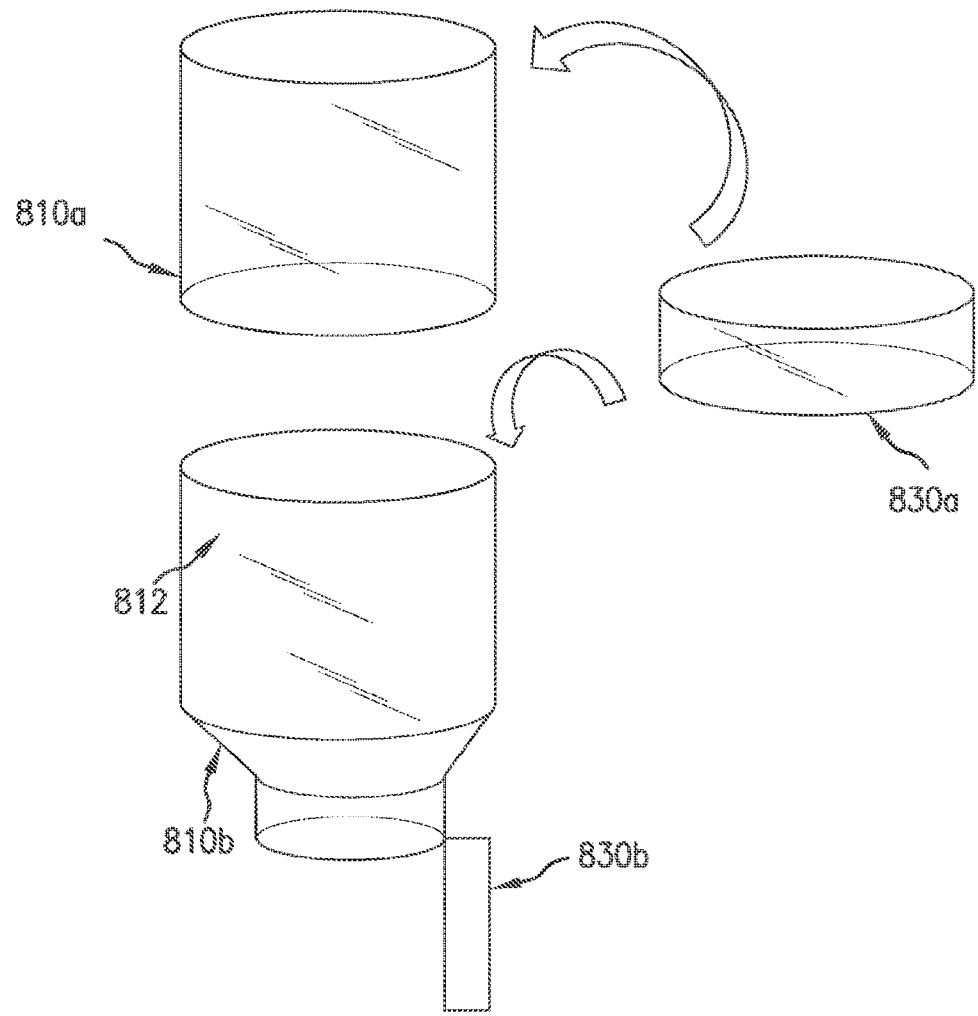
FIG. 16 is an exploded view of an alternative exemplary embodiment of the disclosed subject matter.

From a pathology perspective, physicians are typically interested in examining the cells collected by the filter membrane, whereas from a diagnostic, biochemical, and molecular perspective, physicians are typically interested in examining the liquid or "supernatant" which passes through filter membrane. Consequently, in some scenarios both portions of the sample (i.e. cell and supernatant) are retained and need to be sent to two different laboratories. Thus, and in accordance with another aspect of the disclosed subject matter, the filter membrane with the collected cell sample can be removed, while the supernatant is secured within the tube for parallel processing. In the exemplary embodiment illustrated in FIG. 16, after a centrifuge process is performed the sample cell is retained by filter membrane (not shown) to rest on shelves 812, and the fluid or supernatant is contained within lower tubular member 810 b.

A first cap 830 a is provided to engage with the top of either the elongate tubular member 810a (for scenarios in which it is desirable to remove the filter membrane and collected cell sample while packaging the fluid supernatant in the two tubes 810a, 810b together), or elongate tubular member 810b (for scenarios in which it is desirable to remove the filter membrane and collected cell sample while packaging the fluid supernatant in tube 810b alone). A second cap 830b is provided to engage with the bottom of elongate tubular member 810b. In some embodiments the second cap 830b is hingedly attached to the tubular member 810b and allowed to pivot between open and closed positions. This allows for rapid removal of the fluid in a controlled manner that is not obstructed by the filter assembly above.

The first cap 830a can be configured with both internal and external threads such that a single cap can be employed with a plurality of tube sizes (i.e., male engagement with smaller diameter tubes, and a female engagement with larger diameter tubes). It is to be understood that the disclosed cap arrangements can be employed on any of the disclosed tubular configurations (e.g., one piece, two-piece, telescopingly received, etc.) and for any desired size. Furthermore, in some embodiments, prior to use of the apparatus, the components of the disclosed subject matter are sized such that as the cap 830a is tightened on the tube a compressive force is applied to further compress the filter membrane to ensure a leak-tight seal is formed (between the filter membrane and interior surface of the tubular body) during the centrifuge process. Similarly, upon insertion of the filter assembly components within the tube(s), the user can compress the assembly such that the frictional forces retained between the filter assembly components and the tube sidewall creates a seal which allows a user to pour the contents into the tube without concern for unwanted leakage past the filter membrane prior to centrifuging.

Figure 17A:
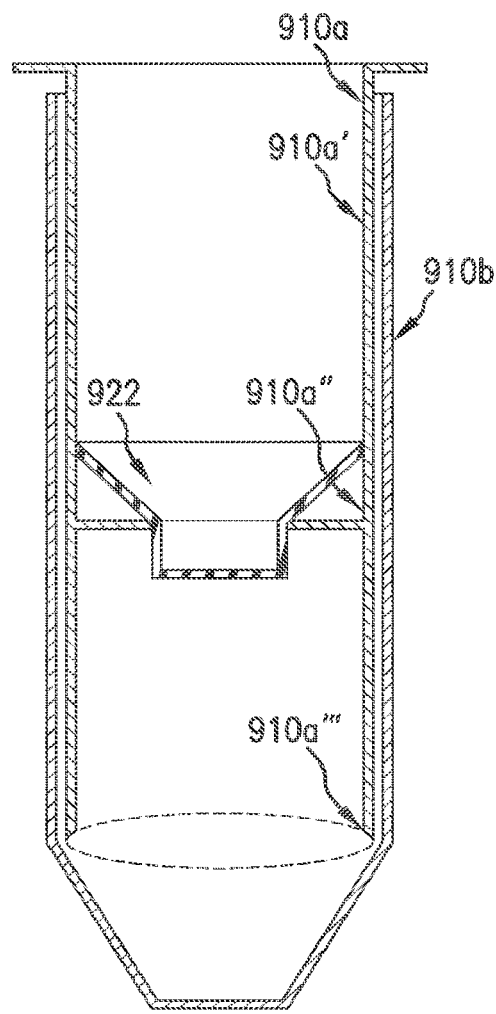
FIG. 17A is a schematic diagram of an alternative exemplary embodiment of the disclosed subject matter.
Figure 17B:
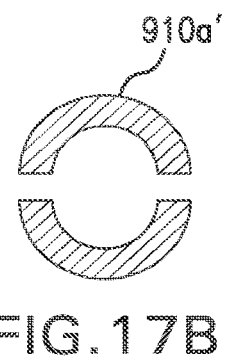
FIG. 17B-D are cross-sectional plan views showing the assembled embodiment of FIG. 17A.
Figure 17C:
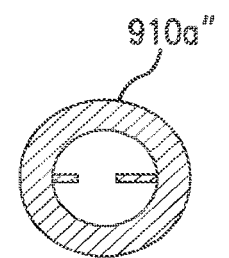
Figure 17D:
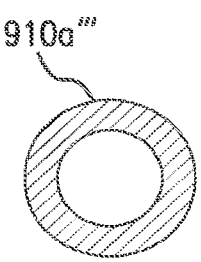

FIG. 17A depicts another exemplary embodiment of the disclosed subject matter in which the first elongate tubular body 910a is fully inserted within the second elongate tubular body 910b. The filter membrane is inserted within the first (or inner) elongate tubular body 910a and includes structural reinforcement members in the form of an outwardly protruding shelf to be received by corresponding inwardly protruding shelf of the first (or inner) elongate tubular body 91a. As described above, the first elongate tubular body 910 a can include longitudinally extending slots formed in the sidewall of the tube. These slots extend from the location of the filter membrane retaining shelf (e.g., the midpoint of tube 910 a) upwards to the top of the container. FIGS. 17B-D depict a top view of a cross-section of the first elongate tubular body 910a at the respective locations 910a', 910a", and 910a'" along the length of the elongate tubular body as designated in FIG. 17A. The upwardly extending slots are advantageous in that they allow for a filter membrane to be easily placed and readily removed from within the first tube 910a by grabbing the filter membrane 922 from exterior of the elongate tubular body 910 (e.g., by the handles described above, if present) and sliding the filter membrane up and out of the tube 910a. An additional advantage of the embodiment depicted in FIGS. 17A-D is that it can be readily configured to fit existing centrifuge tubes, thus avoiding expensive or complex retrofit operations.

Figure 18:
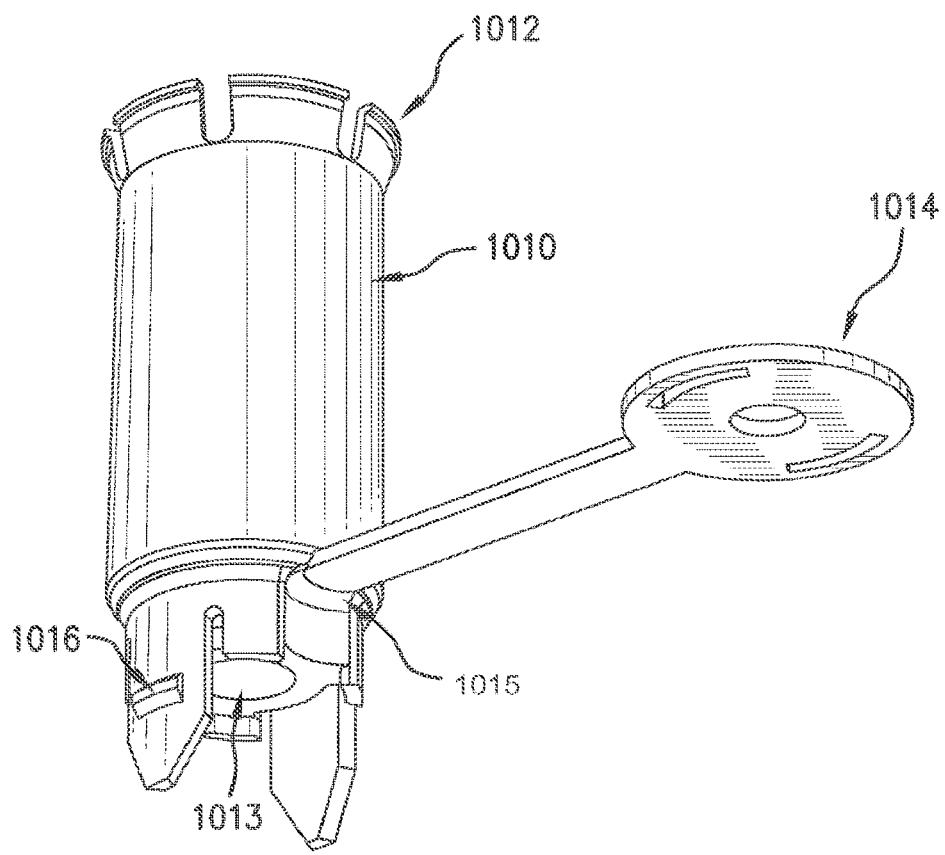
FIG. 18 is a schematic diagram of an alternative exemplary embodiment of the disclosed subject matter.

In another embodiment, and as depicted in FIG. 18, an elongate tubular body 1010 which is designed to be inserted within a second elongate tubular body (not shown). The elongate tubular body 1010 includes a proximal or top end having a structural retention feature 1012, (e.g., flange or ledge) configured to engage the top of the second elongate tubular body upon insertion therein. The structural retention feature 1012 can extend so as to curl or overlay a lip formed in the second elongate tubular body to provide a more secure union. At a distal or bottom end of the elongate tubular body 1010, a closing mechanism (e.g., cap) 1014 is hingedly attached at 1015 (e.g. by a living hinge) to the elongate tubular body 1010. Accordingly, the closing mechanism 1014 can pivot between open and closed positions. A filter membrane or assembly (not shown) can be positioned at the distal end 1013 of the elongate tubular body 1010 and securely retained in this position by rotating the closing mechanism 1014 from the open (as depicted in FIG. 18) to closed (not shown) positions. A locking mechanism (e.g., protrusion) 1016 can be included on the distal end of the elongate tubular body 1010 in order to secure the closing mechanism 1014 in the closed position and retain the filter membrane/assembly therein for commencement of a filtration process. In the embodiment depicted in FIG. 18, the closing mechanism 1014 includes slots for receiving in a snap-fit engagement the locking mechanism 1016. Upon completion of the filtration process, a user can squeeze the downwardly extending tabs of the elongate tubular body 1010 to cause deflection and release of the locking mechanism 1016 from the slots within the closing mechanism 1014.

Figure 19B:
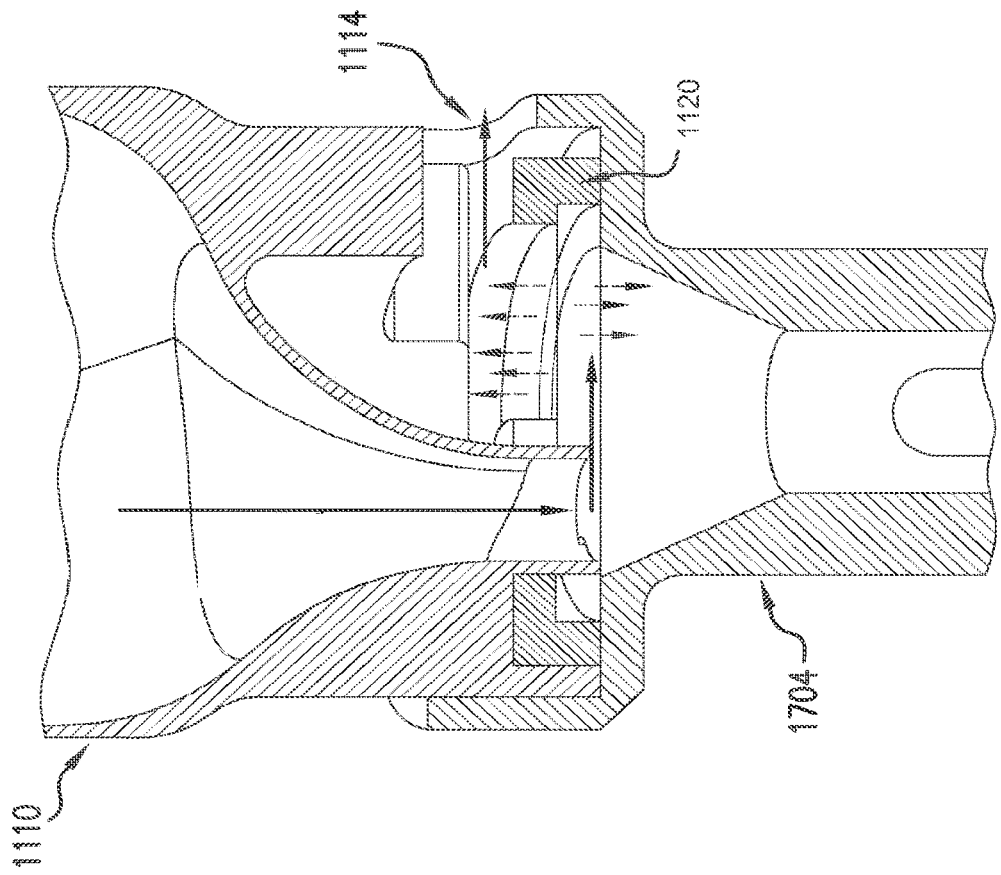
FIGS. 19A-B are schematic diagrams of an alternative exemplary embodiment of the disclosed subject matter, with FIG. 19B depicting a zoom-in view of a cross-sectional view.
Figure 19A:
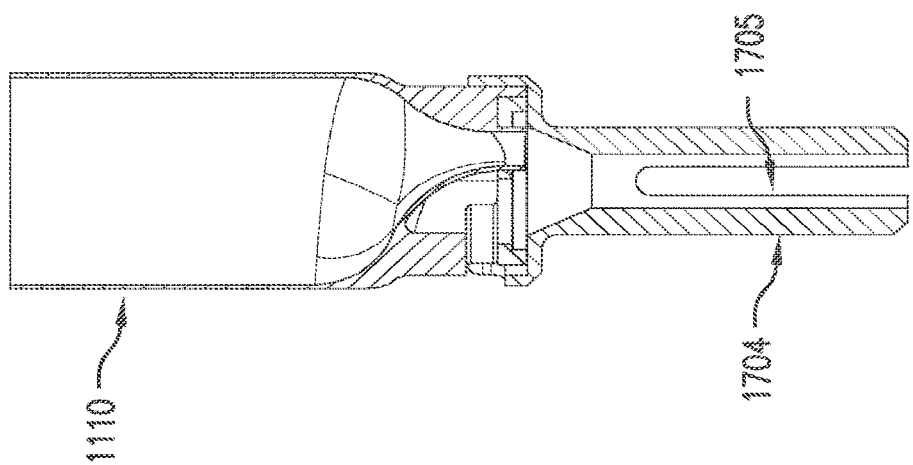
Figure 20A:
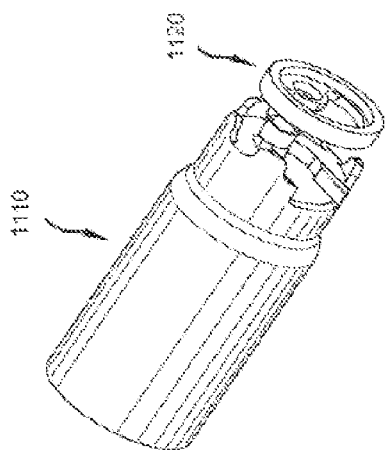
FIG. 20A-D are schematic diagrams of the embodiment of FIGS. 19A-B, with FIG. 20A depicting a exploded view, FIGS. 20B-C depicting partially assembled views, and FIG. 20D depicting a fully assembled view.
Figure 20B:
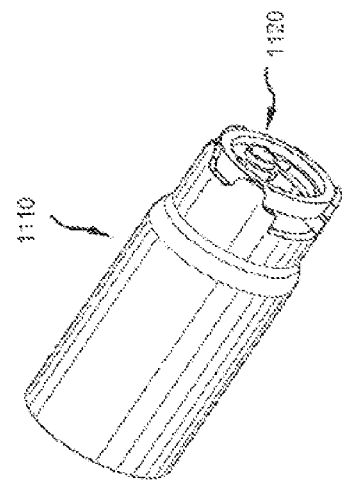
Figure 20C:
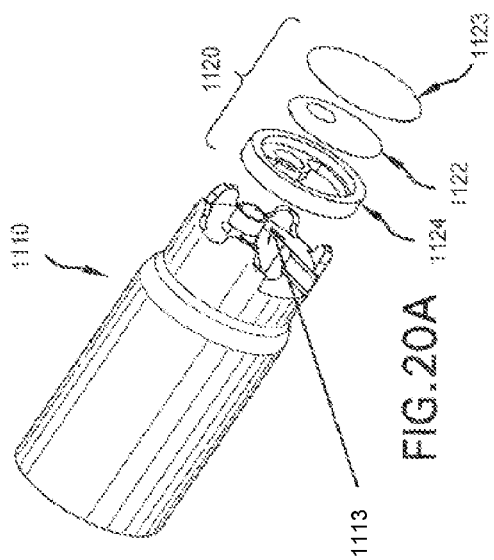
Figure 20D:
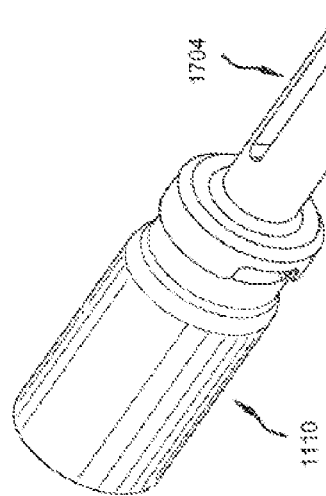

In yet another embodiment, an alternative geometry is provided which employs cross-flow filtration which increases the filtration surface area and thereby reduces the overall cycle time required for a desired amount of filtration, as well as minimizes clogging. The structure depicted in FIG. 19A-B includes an elongate tubular body 1110 and underlying support member 1704 which can be configured for assembly and placement within a second elongate tubular body (not shown). Also, the support member 1704 includes a slot or channel 1705, which functions similarly to the slot 705 disclosed above with respect to FIGS. 14A-C. The filter membrane 1120 (or assembly, if configured as discrete components) includes two filtration surfaces, i.e. upper surface 1122 and lower surface 1123 (see FIG. 20A). The upper filtration surface 1122 is sized such that it is received within the housing or border portion 1124. The lower filtration surface 1123 is sized such that it has an equivalent outer diameter as the housing 1124.

The elongate tubular body 1110 has an internal taper resulting in a reduced diameter (relative to the proximal opening or mouth) outlet 1112 which extends into the filtration space defined between the upper and lower surfaces of the filter membrane 1120. The outlet includes a non-planar surface 1113 at the opening, such as a notch or recess. Accordingly, only a portion of the outlet 1112 engages the lower filtration surface 1120, when assembled, resulting in a lateral port or recess which presents a path of least resistance for exiting fluid. Consequently, as fluid exits the outlet, the non-uniform surface at the outlet 1113 imparts a force on the exiting fluid which directs a portion of the flow in a transverse or tangential direction, across the filter surface (as indicated by the arrows in FIG. 19B). The elongate tubular body 110, and/or the underlying support member 1704, also include a side port 1114 which allows fluid to exit the apparatus and enter the main centrifuge tube (not shown).

Figure 22:
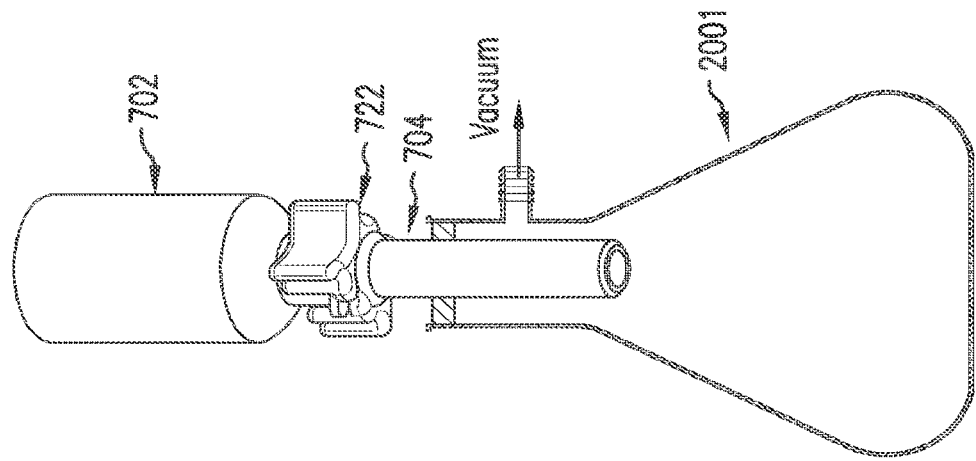
FIGS. 21-22 are schematic diagrams of an alternative exemplary embodiment of the disclosed subject matter depicting vacuum mechanisms.
Figure 21:
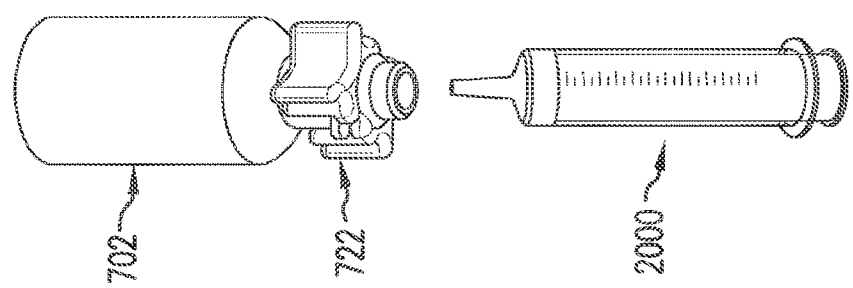

In accordance with another aspect of the disclosed subject matter, and as an alternative to conventional centrifuging processes, the filtration force employed in concert with the apparatus disclosed herein can be provided by a suction force. For purposes of illustration and not limitation, FIGS. 21-22 illustrate some embodiments wherein the driving force is provided via a syringe (FIG. 21) or a vacuum source (FIG. 22). For example, the support member 722 (as previously disclosed with respect to FIGS. 14A-C) can be configured with a tapered opening to sealingly couple with an external syringe 2000. The user can then pull back on the syringe plunger to draw the fluid from the elongate tubular body 702, through the filter membrane 722 and into the barrel of the syringe. Similarly, and as depicted in FIG. 22, an external vacuum source can be coupled to the support member 704 and activated to draw the fluid from the elongate tubular body 702, through the filter membrane 722 and into a receptacle or reservoir 2001 of the vacuum.

Figure 23A:
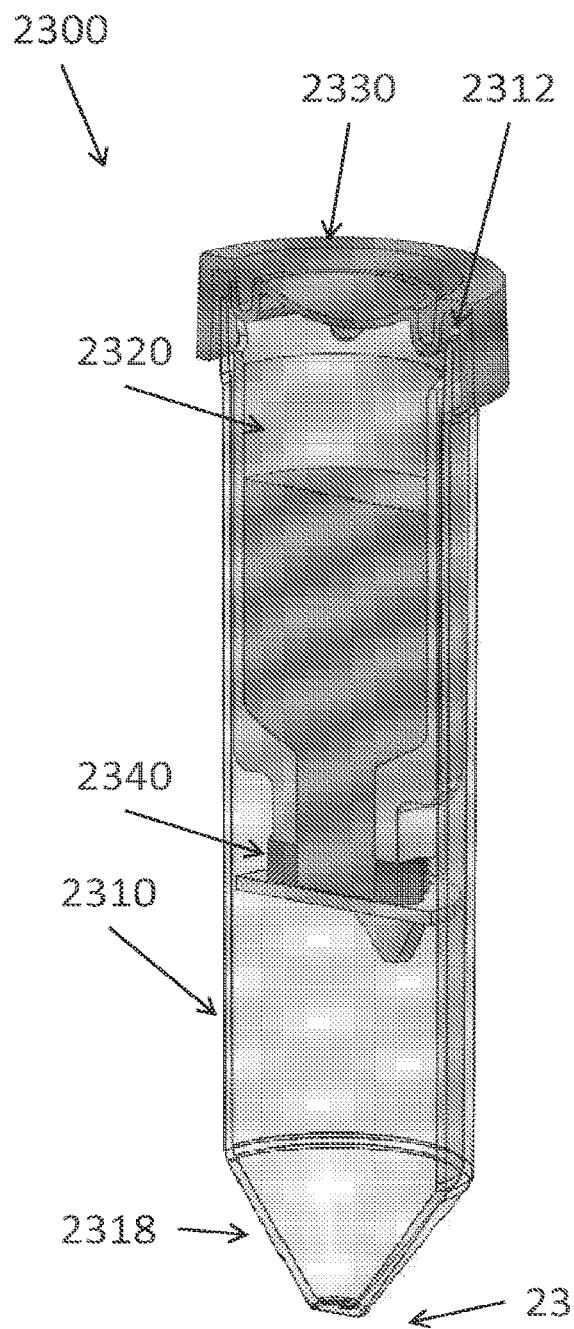
FIGS. 23A-B are cross-sectional views of an alternative exemplary embodiment of the disclosed subject matter.
Figure 23B:
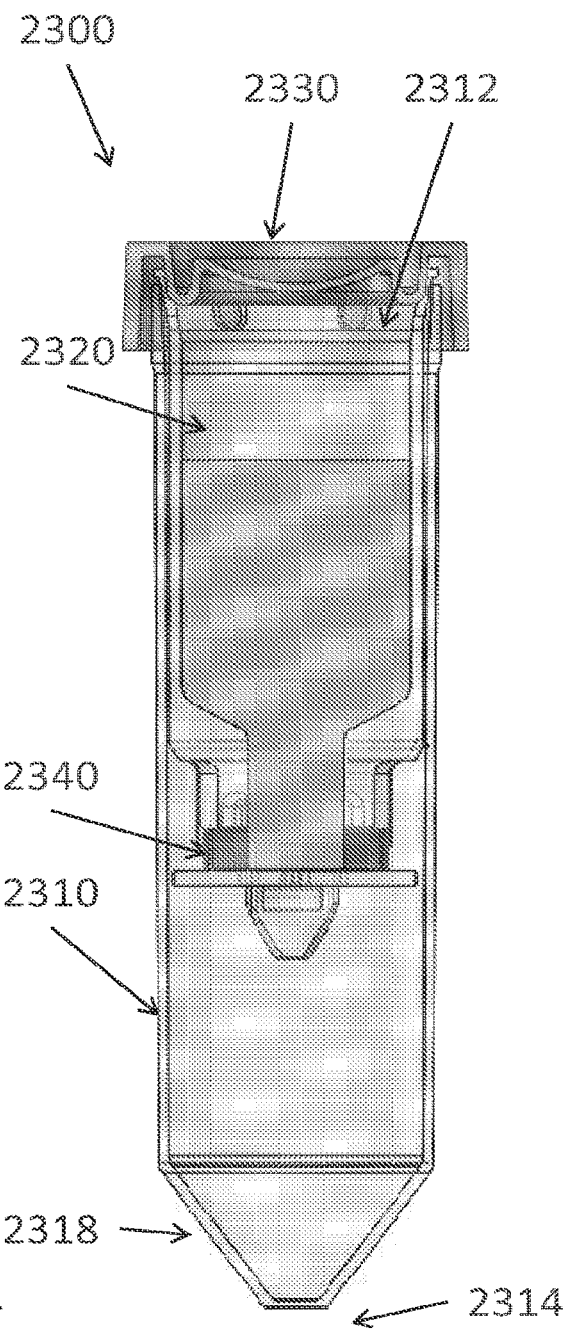

In one exemplary embodiment, the apparatus is configured as a cell block apparatus 2300 as shown schematically in FIG. 23A-B. Cell block apparatus 2300 includes an elongate tubular body 2310 and a sample loading chamber 2320. The elongate tubular body 2310 has a proximal end 2312 and a distal end 2314. In some embodiments, the elongate tubular body 2310 has a first diameter (d1) at the proximal end and a second diameter (d2) at the distal end, wherein the second diameter is smaller than the first diameter. A section 2318 disposed between the proximal end 2312 and the distal end 2314 of the elongate tubular body 2310, has a decreasing diameter along a length thereof to define a generally conical distal section of the elongate tubular member 2310. In some embodiments, a less gradual taper can be provided such that the elongate tubular body includes a step or abrupt restriction in diameter at 2318. A cover 2330 is detachably disposed at the proximal end of elongate tubular body 2310. A filter membrane (or filtration insert) 2340 (which can be the filter membrane alone, or an assembly as described above, e.g. in FIGS. 4-8 and 10-11) is disposed on the sample loading chamber 2320 within the elongate tubular body 2310. Various suitable volumes are available for elongate tubular body 2310. For purpose of illustration and not limitation, suitable volumes include between about 15 ml to about 50 ml, or any other size that fits into a centrifuge, standard or otherwise. Various suitable volumes are available for sample loading chamber 2320. For purpose of illustration and not limitation, suitable volumes include between about 15 ml to about 50 ml, or any other size that fits into elongate tubular body 2310. However, it will be understood by one of ordinary skill in the art that alternative sizes are within the scope of the disclosed subject matter. The elongate tubular body is sized to fit within a conventional centrifuge. In this manner, the cell block apparatus can receive the biological sample, for example, from a needle housing the biological sample obtained by fine needle aspiration techniques, and be disposed in the centrifuge for separation of the cells in the biological sample from any liquid to isolate and consolidate the cells into a concentrated pellet by centrifugation. Using the same unit for receiving the biological sample and separating the biological sample into component parts reduces the loss of sample size and reduces risk of contamination due to exchange between multiple components. In some embodiments, the elongate tubular body is suitable for relative centrifugal forces of between about 1,200 to about 16,000 RCF. For example, 12,000 RCF, 1,200 RCF, 16,000 RCF, 2,000 RCF, 9,400 RCF, 7,500 RCF. For further illustration in one embodiment, the elongate tubular member has a volume of 15 ml, and is suitable for centrifugation at 1,200 RCF or 12,000 RCF. In other embodiments, for example, the elongate tubular member has a volume of 50 ml and is suitable for centrifugation at 16,000 RCF or 2,000 RCF or 9,400 RCF. The elongate tubular body of the device can be formed of various materials and in particular various polymers, for example, polypropylene and/or polystyrene. Further, the materials used for the elongate tubular body, sample loading chamber, or cover, can be biodegradable materials.

In one exemplary embodiment, and as depicted in FIG. 24A-B, a sample loading chamber 2320 is designed to be inserted within elongate tubular body 2310. The sample loading chamber 2320 includes a proximal or top end having a structural retention feature 2412, (e.g., flange or ledge) configured to engage the top of the elongate tubular body 2310 upon insertion therein. The structural retention feature 2412 can extend so as to curl or overlay a lip formed in the elongate tubular body 2310 to provide a more secure union. At a distal or bottom end of the sample loading chamber 2320, a closing mechanism (e.g., cap) 2414 is hingedly attached at 2415 (e.g. by a living hinge) to the sample loading chamber 2320. Accordingly, the closing mechanism 2414 can pivot between open (as depicted in FIG. 24B) and closed (FIG. 24A) positions. A filter membrane 2340 (not shown) can be positioned at the distal end 2413 of the sample loading chamber 2320 and securely retained in this position by rotating the closing mechanism 2414 from the open (as depicted in FIG. 24B) to closed (as depicted in FIG. 24A) positions. A locking mechanism (e.g., protrusion) 2416 can be included on the distal end of the sample loading chamber 2320 in order to secure the closing mechanism 2414 in the closed position and retain the filtration membrane 2340 for commencement of a filtration process. In the embodiment depicted in FIG. 24A-B, the closing mechanism 2414 includes slots for receiving in a snap-fit engagement the locking mechanism 2416. In alternative embodiments (not pictured), closing mechanism 2414 is not attached to sample loading chamber 2320, but may be opened and closed by disengaging and engaging locking mechanism 2416. Upon completion of the filtration process, a user can squeeze the downwardly extending tabs of the sample loading chamber 2320 to cause deflection and release of the locking mechanism 2416 from the slots within the closing mechanism 2414.

In accordance with an aspect of the presently disclosed subject matter, the filtration membrane 2340, can be formed with alternating peaks and valleys around its circumference, as shown in FIG. 25, to increase the surface area and provide greater stability and reliability during both the centrifuge step as well as the subsequent sectioning (i.e. cutting). The border (or frame) of the filter membrane can be formed with a greater thickness than the porous filter portion, and serve as a gasket which forms a seal with the interior surface of the sample loading chamber 2320. Further, this border portion can be formed of opaque material which further serves as a visual aid to easily identify particular areas of interest in the sample collected on the inner porous material. Furthermore, this border portion of the filter membrane can be formed of a porous material, e.g. open cell foam or foam rubber, which allows the cutting blade to easily slice through the filter membrane without excessive force, thereby eliminating any undesired buckling of the filter membrane, damage to the blade, or splintering or flaking of the filter membrane. Additionally, the filter membrane can be formed separately from the remainder of the filter assembly (e.g., the porous filter membrane which serves to separate the tissue(s), or cell block, from the collected sample of fluid/tissue can be distinct from the surrounding frame having the undulating structure and indicia as shown in FIG. 10A). The porous filter membrane can be attached to the surrounding structure via adhesive or ultrasonic welding.

In accordance with an aspect of the presently disclosed subject matter, containers 2600 are adapted to contain filter membrane 2340 as depicted in FIG. 26. Containers 2600 are substantially rectilinear, having a hinged top surface, a fixed bottom surface, and four perpendicular sides. The top and bottom surfaces are perforated by a series of regularly spaces slots to form a grating. The top surface is affixed to one side of the container by a hinge. The side opposite the hinge is inclined towards the center line of the container so as to allow access to a tab disposed on the edge of the top surface opposite the hinge. Containers 2600 are used for storage of filter membranes 2340. The grating in container 2600 allows the passage of air, water, or clearing solutions in order to clean filter membrane 2340.

FIGS. 27A-F depict the assembly of cell block apparatus 2300 according to an exemplary embodiment of the disclosed subject matter. Filter membrane 2340 is placed at the distal end of the sample loading chamber 2320 (FIG. 27A), and is fixed in place using closing mechanism 2414. Cover 2330 is removed from elongate tubular body 2310 (FIG. 27B). Sample loading chamber 2320 is placed within elongate tubular body 2310 (FIG. 27C), and is held in place at the top of the elongate tubular body 2310 by structural retention feature 2412. A biological sample is placed in sample loading chamber 2320 (FIG. 27D), and the cover 2330 is replaced on elongate tubular body 2310 (FIG. 27E). After spinning in a centrifuge, a liquid portion of the biological sample collects in the distal end of the elongate tubular body 2310 (FIG. 27F).

FIGS. 28A-E depict the assembly of cell block apparatus 2300 according to an exemplary embodiment of the disclosed subject matter. Filter membrane 2340 is placed at the distal end of the sample loading chamber 2320 (FIG. 28A), and is fixed in place using closing mechanism 2414. Cover 2330 is removed from elongate tubular body 2310 (FIG. 28B). A biological sample is placed in sample loading chamber 2320, sample loading chamber 2320 is placed within elongate tubular body 2310, and cover 2330 is replaced on elongate tubular body 2310 (FIGS. 28C-D). After spinning in a centrifuge, a liquid portion of the biological sample collects in the distal end of the elongate tubular body 2310 (FIG. 28E).

In another exemplary embodiment, the apparatus is configured as a cell block apparatus 2900 as shown schematically in FIG. 29. Cell block apparatus 2900 includes an elongate tubular body 2910 and a sample loading chamber 2920. The elongate tubular body 2910 has a proximal end 2912 and a distal end 2914. In some embodiments, the elongate tubular body 2910 has a first diameter (d1) at the proximal end and a second diameter (d2) at the distal end, wherein the second diameter is smaller than the first diameter. A section 2918 disposed between the proximal end 2912 and the distal end 2914 of the elongate tubular body 2910, has a decreasing diameter along a length thereof to define a generally conical distal section of the elongate tubular member 2910. In some embodiments, a less gradual taper can be provided such that the elongate tubular body includes a step or abrupt restriction in diameter at 2918. A cover 2930 is detachably disposed at the proximal end of elongate tubular body 2910. A filter membrane 2940 is disposed on the sample loading chamber 2920 within the elongate tubular body 2310. As previously described in connection with the alternative embodiments, various suitable volumes are available for elongate tubular body 2910 and sample loading chamber 2920. For purpose of illustration and not limitation, suitable volumes include between about 15 ml to about 50 ml, or any other size that fits into a centrifuge, standard or otherwise.

As previously described, the elongate tubular body is sized to fit within a centrifuge and the cell block apparatus can receive the biological sample, for example, from a needle housing the biological sample obtained by fine needle aspiration techniques, and be disposed in the centrifuge for separation of the cells in the biological sample from any liquid to isolate and consolidate the cells into a concentrated pellet by centrifugation. Similarly to the previously described embodiments, the elongate tubular body of the device can be formed of various materials and in particular various polymers, for example, polypropylene and/or polystyrene. Further, the materials used for the elongate tubular body, sample loading chamber, or cover, can be biodegradable materials.

In the embodiment depicted in FIGS. 29 and 30A-C, a sample loading chamber 2920 is designed to be inserted within elongate tubular body 2910. The sample loading chamber 2920 includes a proximal or top end having a structural retention feature 2912, (e.g., flange or ledge) configured to engage the top of the elongate tubular body 2910 upon insertion therein. The structural retention feature 2912 can extend so as to curl or overlay a lip formed in the elongate tubular body 2910 to provide a more secure union. In the exemplary embodiment shown in FIG. 40, the lip 2912 can include recesses or notches which serve as a vacuum relief mechanism to prevent formation of a vacuum during the centrifuge process. Referring again to FIGS. 29 and 30A-C, the distal or bottom end 2924 of the sample loading chamber 2920 can be configured with a decreasing internal diameter and substantially constant external diameter such that the loading chamber has an internal taper while retaining a generally cylindrical exterior. The distal portion 2924 of the sample loading chamber can include a plurality of fastening features (e.g. threads, protrusions, recesses, etc.) on the exterior for matingly engaging complementary fastening features on the clamp 2950 (described in more detail below). Further, the external diameter of distal portion 2924 can be less than the diameter of the remainder of sample loading tube 2920, such that distal portion is recessed to allow the clamp 2950 to form a flush (co-planar) fitting with the sample loading tube 2920, when assembled.

Similar to the previously described embodiments, the filter membrane 2940, can be formed with alternating peaks and valleys around its circumference to increase the surface area and provide greater stability and reliability during both the centrifuge step as well as the subsequent sectioning (i.e. cutting). The border (or frame) of the filter membrane can be formed with a greater thickness than the porous filter portion, and serve as a gasket which forms a seal with the interior surface of the sample loading chamber 2920. Further, this border portion can be formed of opaque material which further serves as a visual aid to easily identify particular areas of interest in the sample collected on the inner porous material. Furthermore, this border portion of the filter membrane can be formed of a porous material, e.g. open cell foam or foam rubber, which allows the cutting blade to easily slice through the filter membrane without excessive force, thereby eliminating any undesired buckling of the filter membrane, damage to the blade, or splintering or flaking of the filter membrane. Additionally, the filter membrane can be formed separately from the remainder of the filter assembly (e.g., the porous filter membrane which serves to separate the tissue(s), or cell block, from the collected sample of fluid/tissue can be distinct from the surrounding frame having the undulating structure and indicia as shown in FIG. 10A). The porous filter membrane can be attached to the surrounding structure via adhesive or ultrasonic welding Also included in the exemplary embodiment of FIG. 29 is a post-filtration cap 2960. This post filtration cap 2960 can be inserted into the recess formed within the filter membrane 2940 so as to sealingly contain the collected sample within the filter membrane 2940 for further processing. Although the exemplary embodiment of FIG. 29 depicts a cylindrical post-filtration cap 2960, it is to be understood that a variety of sizes and/or shapes can be employed as so desired and that it is the dimensions of the filter membrane 2940 which determine the size/shape of the post-filtration cap 2960. In the exemplary embodiment shown in FIGS. 41-42B, the post-filtration cap 4160 includes a foam portion 4162 and a wax or low-density polyethylene (LDPE) portion 4164 disposed over the filter portion 4166 (FIG. 41). The foam 4162 can be infiltrated with wax 4164 (FIG. 42A) and this subassembly can be welded to the filter 4166 (FIG. 42B). In the embodiment shown in FIGS. 43A-B, the filter portion is omitted and the post-filtration cap 4360 includes only the foam 4362 and wax/LDPE portion 4364. In some embodiments, the wax is mixed with low density polyethylene (LDPE) to create a material (which can be used for portion 4164 as well as the filtration insert 2940) with similar properties to the embedding paraffin wax to facilitate sectioning, but exhibits a higher melting temperature to maintain integrity of the collected cell block during tissue processing.

As shown in FIGS. 30A-C, the filtration insert 2940 is disposed within the clamp 2950 which is in turn attached to the distal end of the sample loading chamber 2920 (see FIG. 30B). This subassembly is then disposed within the elongate tubular body 2910 and ready to receive a biological sample at the proximal end (see FIG. 30C). The clamp 2950 can be configured with a planar bottom surface having at least one aperture 2953 therein for allowing liquid to easily pass through during the centrifuge process. As best shown in FIG. 29, the clamp 2950 also includes two sidewalls 2952, 2954 extending upwardly from the planar bottom surface. As noted above, the sidewalls include fastening features (e.g. threads, protrusions, recesses, etc.) on the interior surface which are configured to releasably engage the fastening features on the exterior surface of the distal portion 2924 of the sample loading chamber. The sidewalls are configured with an arcuate shape having a radius of curvature that coincides with the contour of the sample loading chamber 2920. A recess or opening is disposed between the two sidewalls 2952, 2954 which allows for easy access to the filtration insert 2940 to facilitate insertion and removal of the filter membrane 2940 with respect to the clamp 2950.

Referring again to the clamp member 2950, as previously described with respect to FIGS. 29-30C, the two arcuate sidewalls 2952, 2954 include fastening features to engage complementary fastening features on the sample loading chamber 2920. In the exemplary embodiment of FIGS. 37-38, the filter membrane 2940 is positioned within the clamp 2950 via the finger access slots or openings between sidewalls 2952, 2954. Thereafter, the clamp is securely coupled to the sample loading chamber 2920 via a threaded engagement by twisting or screwing the clamp 2950 in a clockwise or counterclockwise direction. In the exemplary embodiment of FIG. 38, the clamp is securely coupled to the loading chamber 2920 via a ratchet engagement (i.e. a combination of rotation and translational movement). In other words, the operator pushes the clamp upwards or towards the sample loading chamber 2920 while simultaneously twisting the clamp 2950 in a clockwise or counterclockwise direction. In the alternative embodiment of FIGS. 39A-B, the sidewalls 3952, 3954 include downwardly extending tabs, which upon completion of the filtration process, an operator can squeeze to cause deflection (FIG. 39A) and release of the filter membrane 2940 from the slots within the clamp 2950.

FIGS. 31A-D depict the various stages of the filtration process. After assembly of the filtration device (FIGS. 30C and 31A) a biological sample is deposited within the sample loading chamber 2920 (FIG. 31B) and cover 2930 is placed on elongate tubular body 2910 (FIG. 31C). After spinning in a centrifuge, a liquid portion of the biological sample collects in the distal end of the elongate tubular body 2910 while the cells are collected in the filter membrane 2940 (FIG. 31D).

In accordance with an aspect of the disclosed subject matter, containers 3200 are adapted to contain filter membrane 2940 (and post-filtration cap 2960, if present) as depicted in FIG. 32. These containers 3200 are advantageous in that they serve as a convenient and secure storage mechanism for retaining the filter membrane 2940, which contains the captured cells, and facilitates additional processing of filtration insert 2940 (and captured cells). In the embodiment depicted in FIGS. 32-34, containers 3200 are substantially rectilinear, having top surface 3210 and a bottom surface 3220 which includes four perpendicular sides. The top and bottom surfaces are perforated by a series of regularly spaces slots to form a grating. The top surface is affixed to one side of the container by a hinge. The side opposite the hinge is inclined towards the center line of the container so as to allow access to a tab disposed on the edge of the top surface opposite the hinge. The top surface 3210 can be removably attached to the bottom surface 3220, or permanently attached, e.g., via a living-hinge, as so desired. Alternatively, the top surface 3210 can be attached to the bottom surface 3220 via a tongue and groove coupling such that the top surface translates or slides in a linear fashion with respect to the bottom surface 3220 to open and close the container 3200. The grating in container 3200 allows the passage of air, water, or clearing solutions in order to clean filter membrane 2940.

As shown in FIGS. 33A-D, after the centrifuge process the cells are collected within the filter membrane 2940 and a post-filtration cap 2960 can be inserted within filter membrane 2940 (FIG. 33A). The filter membrane 2940 and cap 2960 are then inserted within container 3200 (FIG. 33B) and the top surface 3210 is pivoted to close the containers 3200 (FIG. 33C-D). The cavity within the container 3200 can be sized such that the top surface 3210 compresses the filtration insert 2940 and cap 2960 upon closure of the container 3200. This serves to further constrain and compact the cells collected within filter membrane 2940, as shown in FIG. 34.

In accordance with another aspect of the disclosed subject matter, a mold 3500 is provided for embedding the filter membrane 2940 for additional processing, as shown in FIG. 35A. In operation, the filter membrane 2940 is removed from the container 3200 (as shown in FIGS. 33A-D) and positioned within the mold 3500. Similar to the container 3200, the mold includes and top 3510 and bottom 3520 which can be sealingly engaged via hinge or tongue and groove assembly. The bottom 3520 includes a recess or compartment 3522 for receiving filtration insert 2940 (FIG. 35B). A liquid or wax (e.g. paraffin) is deposited within the mold and surrounds the filter membrane 2940 within recess 3250 (FIG. 35C). Thereafter, the paraffin encapsulated filter membrane 2940 is removed from the mold 3500. In the embodiment shown in FIG. 35D, the bottom 3520 is detached while the top 3510 is coupled to the encapsulated filtration insert 2940. This can be advantageous in that the top 3510 can serve as a handle for an operator to manipulate and reposition the encapsulated filter membrane 2940 for sectioning (as described below) without making direct contact the encapsulated filter membrane 2940, thereby preserving the integrity of the collected cells.

In accordance with another aspect of the disclosed subject matter, the encapsulated filter membrane 2940 (which encompasses the collected cells "C" and cap 2960) can be subjected to additional processing, such as the sectioning shown in FIGS. 36A-F. The filter membrane can be mounted to a device (not shown) for slicing or cutting into sections 2940' for further examination (e.g. electron microscope) (FIG. 36C). This process can be continued until the entire block of collected cells has been sectioned/sliced. Additionally, the filter membrane 2940 is designed to indicate to the operator when the entirety of the cell block has been sectioned/sliced in that the operator will recognize the distinct color (or other suitable indicia) of the cap 2960 (as compared to the filtration insert 2940) as signaling that the complete cell block "C" has been traversed via the sectioning/slicing steps (FIG. 36D). The slices 2940' (which include the cells "C" and paraffin wax "W") are mounted on a slide 3600 for further inspection (FIG. 36E). Furthermore, the slide can be heated to melt or dissolve the paraffin wax thereby leaving only the cells on the slide for inspection (FIG. 36F).

Similar to the previously described embodiments, a filter membrane 4440, can be formed with an enlarged border (or frame) extending around its circumference to increase the surface area and provide greater stability and reliability during both the centrifuge step as well as the subsequent sectioning (i.e. cutting). Accordingly, the present disclosure provides a filter membrane than can be sectioned or cut multiple times to provide multiple slices and thus slides for microscopic viewing) from a single biological sample.

Figure 45:
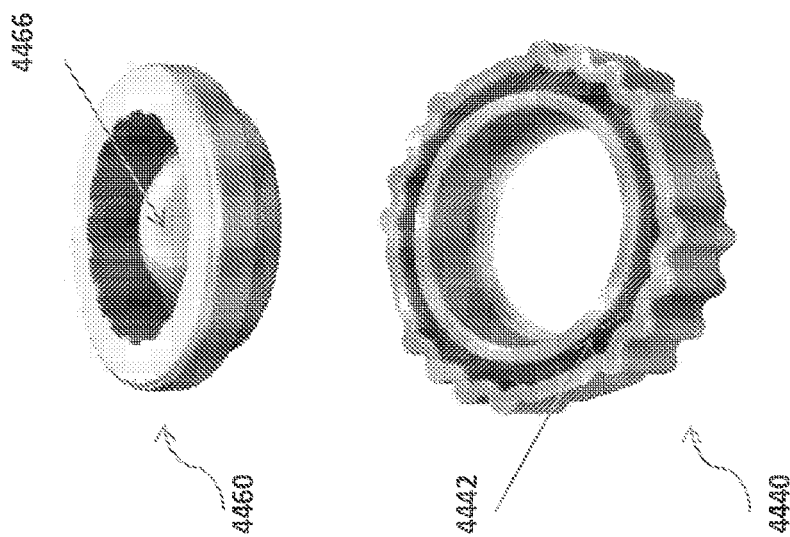
FIG. 44-45 are exploded-part schematic views of another embodiment of the filter membrane and cover in accordance with the disclosed subject matter.
Figure 44:
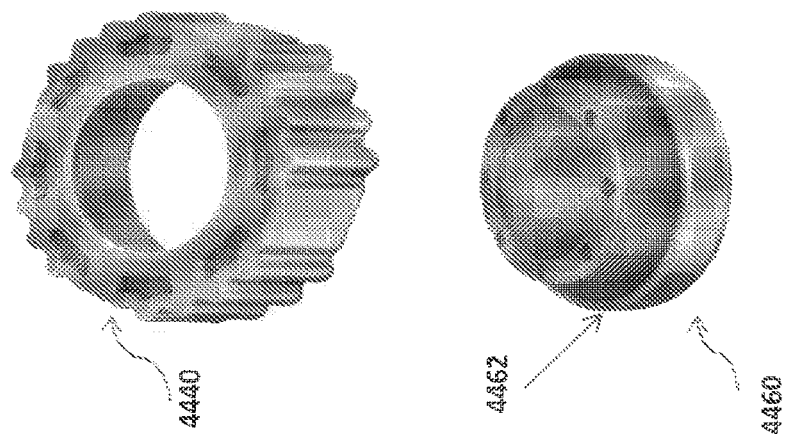
Figure 45A:
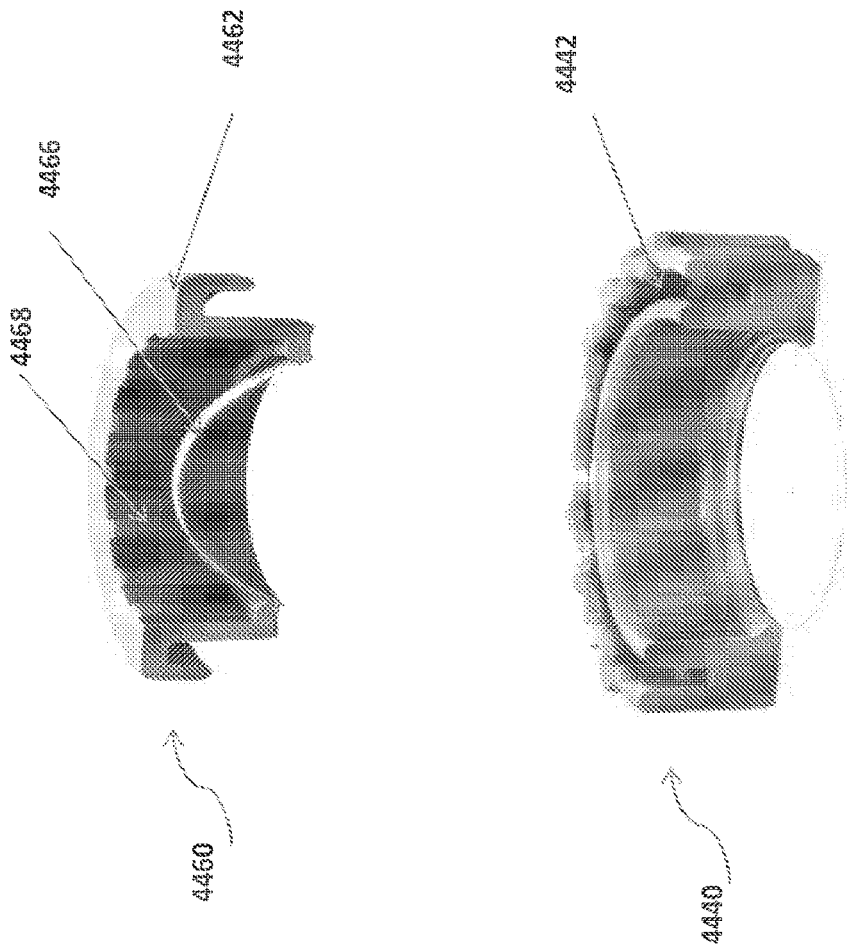
FIG. 45A is an exploded cross sectional view of the filter membrane and cover of FIG. 45.

As shown in FIGS. 44-46 the border (or frame) of the filter membrane can be formed with a greater thickness than the porous filter portion (which is omitted in these figures for clarity sake of clarity). Further, this border portion can be formed of opaque material which further serves as a visual aid to easily identify particular areas of interest in the sample collected on the inner porous material. A wide variety of materials can be employed for constructing the porous filter and border of the filter membrane. For purpose of illustration and not limitation, the porous filter can be formed of a Polyethylene terephthalate or polycarbonate film, and the border portion of the filter membrane can be formed of a machinable wax, as disclosed in U.S. Pat. No. 4,518,288 (the entire contents of which are hereby incorporated by reference). In some embodiments, the machinable wax has a composition which includes 5 to 15 percent by volume paraffin wax with a melting point of 150° F. to 152° F.; 5 to 15 percent by volume microcrystalline wax having a melting point of substantially 190° F. to 192 F; 5 to 10 percent by volume ethylene/vinyl acetate copolymer having a melting point of substantially 210° F.; 25-35 percent by volume nonemulsifiable polyethylene wax having a melting point of substantially 240° F.; 40 to 50 percent by volume nonemulsifiable polyethylene wax having a melting point of substantially 220° F.; and sufficient blue oil dye to impart a dark blue color to the wax block. The wax allows the cutting blade to easily slice through the filter border without excessive force, thereby eliminating any undesired buckling of the filter membrane, damage to the blade, or splintering or flaking of the filter membrane (thus avoiding contaminating the sample collected). Additionally, the border can be formed separately from the porous filter membrane which serves to separate the tissue(s), or cell block, from the collected sample of fluid/tissue. In such embodiments the porous filter membrane can be attached to the surrounding structure via adhesive, hot plate, infrared, laser or ultrasonic welding. Alternatively, the border and porous filter membrane can be integrally formed as a unitary component. Further, the border can be formed with a radially inward projecting lip at the bottom (as best shown in FIGS. 46A and 51A). The porous membrane can be coupled to the border along this lip.

As shown in FIGS. 45-48, the border of the filter membrane is formed with an upwardly extending sidewall that has a groove or slot 4442 formed therein. The cover 4460 is configured with a complementary flange 4462 which is configured to matingly engage the border slot 4442 (after collection of the biological sample) of the filter membrane to form a seal therebetween and securely retain the biological sample. As previously described, the increase in surface area provided by the undulating peaks and valleys formed in the periphery of the filter membrane facilitates integration with the embedding medium (e.g., wax) and improved anchoring of the filter membrane. The number of peaks and valleys can be varied as so desired, and in some embodiments the side portions are substantially flat (or planar) to increase ergonomic appeal and facilitate handling of the filter membrane by technicians.

The cover 4460 can be formed with a raised surface (e.g. hemispherical dome) 4466 to permit and control the venting of any air retained within the filter membrane (and collected sample) upon compression of the cover into the filter membrane border 4440. Additionally, the cover has a downwardly extending sidewall which can be formed with vertical ribs 4468 on a radially inner surface to increase rigidity and facilitate uniform radial contraction. In the embodiment shown in FIG. 45 the cover sidewall extends downwardly a distance greater than the elevation (relative to the sidewall) of the apex of the raised surface 4466 such that the apex is offset (below) the plane of the cover flange 4462.

Figures 47, 48:
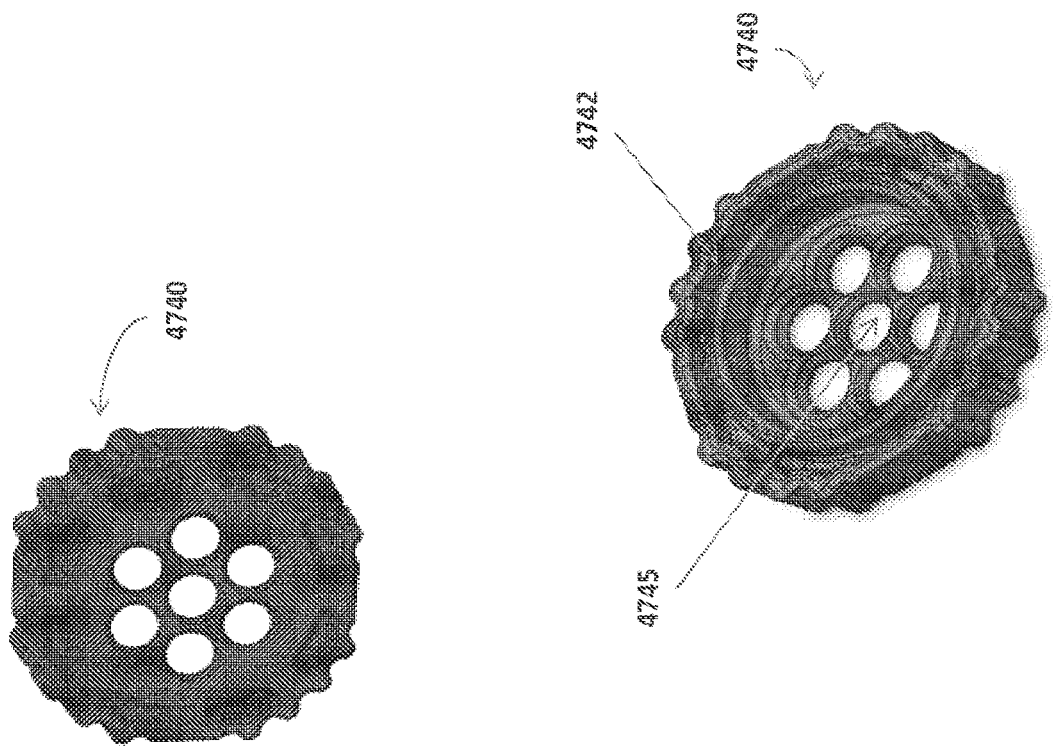
FIGS. 47-48 are alternative embodiments of the filter membrane in accordance with the disclosed subject matter.

In some embodiments, as shown in FIGS. 47-48, the filter membrane 4740 can be formed with a bottom surface that includes a plurality of apertures 4745 which serve as distinct wells or chambers. In use, a single biological sample would be dispensed within the filter membrane (e.g. via centrifuging), with the cell block collected being divided into numerous wells/chambers. This allows for multiple testing and analysis to be performed (e.g. at different facilities, or at different times) based on the same biological sample. While the exemplary embodiment illustrated depicts seven apertures, the number, size and positioning of the apertures can vary as so desired.

As shown in FIG. 48 the filter membrane includes a border with a groove 4742 for receiving a cover (not shown). Here, the cover can be formed with a flat or planar surface to facilitate compression of the collected sample thereby urging the sample into the respective filter membranes (not shown) positioned within each aperture 4745. Additionally or alternatively, the collected sample can be retained on the filter membrane 4740 by encapsulating the filter membrane 4440 with an encapsulation material (e.g. histogel).

In accordance with another aspect of the disclosed subject matter, a filter membrane is provided for collecting and forming a cell block from a biological sample without the use of a centrifuge process. As shown in FIGS. 49-51A, the filter membrane 4940 is provided with two porous filter meshes 4966, one which is substantially flush or coplanar with the top surface of the filter membrane border, and one which is substantially flush or coplanar with the bottom surface of the filter membrane border (as best shown in FIG. 51A). Alternatively, the porous filters can be disposed adjacent to the border. In this regard the filter membrane 4940 serves as a single piece retentate chamber for the biological sample collected. The filter membrane border can be formed with upper and lower lips which extend radially inward from the sidewall. Additionally, a one-way valve (e.g. leaf spring valve) 4970 is positioned on the interior surface of the border sidewall, between the upper and lower lips. The one-way valve is biased in a closed position, and is deflected into the open position when the pressure from outside the chamber (i.e. external of the filter membrane 4940) exceeds the pressure within the chamber. In operation, a technician can inject the biological sample via a delivery device (e.g. pump or syringe as shown in FIG. 50) through an inlet port 4950 positioned in the sidewall of the filter membrane border. The pressure within the chamber increases as the amount of biological sample injected therein increases. This internal pressure, along with gravitational forces, draw the biological sample through the porous filter membranes 4966 leaving a cell block retentate within the chamber.

In accordance with another aspect of the disclosed subject matter, as depicted in FIGS. 52-54, a sample loading chamber 5220 is designed to be inserted within elongate tubular body 5210 (see FIG. 53). The sample loading chamber 5220 includes a proximal or top end having a structural retention feature 5212, (e.g., flange or ledge) configured to engage the top of the elongate tubular body 5210 upon insertion therein. The structural retention feature 5212 can extend so as to curl or overlay a lip formed in the elongate tubular body 5210 to provide a more secure union. The distal or bottom end 5224 of the sample loading chamber 5220 can be configured with a decreasing internal diameter and substantially constant external diameter such that the loading chamber has an internal taper while retaining a generally cylindrical exterior. The distal portion 5224 of the sample loading chamber can include a plurality of fastening features (e.g. threads, protrusions, recesses, etc.) on the exterior for matingly engaging complementary fastening features on the clamp 5250 (described in more detail below). Further, the external diameter of distal portion 5224 can be less than the diameter of the remainder of sample loading tube 5220, such that distal portion is recessed to allow the clamp 5250 to form a flush (co-planar) fitting with the sample loading tube 5220, when assembled.

The filter membrane 5240 is disposed within the clamp 5250 which is in turn attached to the distal end of the sample loading chamber 5220 (see FIG. 53). This subassembly is then disposed within the elongate tubular body 5210 and ready to receive a biological sample at the proximal end. The clamp 5250 can be configured with a planar bottom surface having at least one aperture 5253 therein for allowing liquid to easily pass through during the centrifuge process. As best shown in FIG. 29, the clamp 5250 also includes sidewalls extending upwardly from the planar bottom surface which include fastening features (e.g. threads, protrusions, recesses, etc.) on the interior surface which are configured to releasably engage the fastening features on the exterior surface of the distal portion 5224 of the sample loading chamber. The sidewalls are configured with an arcuate shape having a radius of curvature that coincides with the contour of the sample loading chamber 5220.

In the exemplary embodiment of FIGS. 52-54, the filter membrane 5240 is positioned within the clamp 5250. Thereafter, the clamp is securely coupled to the sample loading chamber 5220 via a threaded engagement by twisting or screwing the clamp 5250 in a clockwise or counterclockwise direction. In the exemplary embodiment, the clamp is securely coupled to the loading chamber 5220 via a ratchet engagement (i.e. a combination of rotation and translational movement). In other words, the operator pushes the clamp upwards or towards the sample loading chamber 5220 while simultaneously twisting the clamp 5250 in a clockwise or counterclockwise direction.

The filter membrane 5240 is formed with a slot or groove 5242 (as described in further detail with respect to FIGS. 44-48) at the top of an upwardly extending sidewall. This groove is configured to matingly receive the distal end of the sample loading chamber 5220 (as best shown in FIG. 53B).

Also included within the sample loading chamber 5220 is a valve stem 5260. The valve stem 5260 is biased in the closed position (shown in FIG. 52) which prevents fluid communication between the sample loading chamber 5220 and the filter membrane 5240. As shown in FIG. 53B, the distal end of the valve stem 5260 includes a bulbous portion having a slot or groove 5262 for retaining an O-ring (not shown for sake of clarity). When in the closed position, the bulbous end of the stem valve 5262 sealingly engages the tapered sidewalls of the sample loading chamber 5220. This seal allows a biological sample to be deposited within the sample loading chamber, and for a centrifuging process(es) to be conducted, without any of the sample escaping the sample loading chamber and passing through the filter membrane 5240. Accordingly, the biological sample is separated or stratified (i.e. fluid content disposed above solid content) during the centrifuging process, and only released to communicate or pass through to the filter membrane upon opening of the stem valve 5260.

The stem valve 5260 is opened upon placement of a support cap 5230 onto the sample loading chamber 5220 (and external tube 5210). The downward force exerted by the cap 5230 overcomes the bias of spring 5270 (see FIG. 53A) and allows the bulbous distal end 5262 of the stem valve to move out of engagement with the tapered sidewalls of the sample loading chamber 5220. As shown in FIG. 53A, the spring 5270 has ends which engage the sidewalls of the sample loading chamber 5220, e.g. within the flange located at the mouth of the sample loading chamber. Further, the spring 5270 (which can be a discrete component or integrally formed with the stem valve) extends through an aperture within the stem valve 5260 to effect displacement thereof. Similarly, upon removal of the support cap 5230, the spring 5270 reverts back to its biased position which moves the stem valve 5260 upward so that the bulbous distal end 5262 of the stem valve returns into engagement with the tapered sidewalls of the sample loading chamber 5220.

In other embodiments, instead of the stem valve described above, a stop cock valve or ball valve can be employed to retain the biological sample within the sample loading chamber 5220. Alternatively, a rotating disc valve 5560 can be employed wherein the valve can have an open semicircle (i.e. aperture) 5560' and a solid semicircle, as shown in FIG. 55. The sample loading chamber 5520 can be formed with an internal taper which reduces the size of the opening 5520' at the distal end of the sample loading chamber. When in the closed position the solid semicircle is aligned with the sample loading chamber interior lumen or aperture 5520', thereby preventing fluid communication with the underlying filter membrane 5540. Upon rotation, the disc valve aperture 5560' is brought into alignment with the sample loading chamber opening 5520' such that the contents within the interior lumen or cavity are allowed to fluidly communicate with the underlying filter membrane 5540. While the exemplary embodiment depicts a circular valve having a single hemispherical aperture to permit fluid flow, it is to be understood that alternative shapes, sizes and number of apertures can be provided as desired. The greater the surface area in the sliding disc valve, the greater the impediment to flow through the sample loading chamber and into the filter membrane.

Likewise, a sliding valve can be employed wherein the valve can have a central aperture 5660b' and a solid member 5660a, as shown in FIG. 56. The sample loading chamber 5620 can be formed with an internal taper which reduces the size of the opening 5620' at the distal end of the sample loading chamber. When in the closed position the solid member 5660a overlies or occludes the aperture 5660b', thereby preventing fluid communication with the underlying filter membrane 5640. Upon translation of the solid member 5660a, the sliding valve aperture 5660b' (which is in alignment with the sample loading chamber opening 5620') is no longer occluded thereby allowing the contents within the sample loading chamber 5620 to fluidly communicate with the underlying filter membrane 5640. While the exemplary embodiment depicts a circular valve having a single centrally located aperture to permit fluid flow, it is to be understood that alternative shapes, sizes and number of apertures can be provided as desired. For example, FIG. 56A is an exemplary depiction of an alternative embodiment wherein the aperture is formed as a crescent shape.

Referring again to the cover which can be attached to the filter membrane and compress the biological sample into a uniform cell block, in some embodiments (as shown in FIGS. 57-58) the cover can be constructed as a two-piece component 5760a, 5760b. Upper piece 5760a can be telescopingly coupled to the filter membrane to allow displacement of the top piece into the bottom piece 5760 b, and thus onto the biological sample retained on the underlying filter membrane to compress and facilitate formation of a cell block. The two-piece cover embodiment can be assembled via a tongue and groove coupling in which a top piece 5760a includes protrusions that engage channels within the bottom piece 5760b to permit relative movement of the top and bottom pieces.

In accordance with another aspect of the disclosed subject matter, the sample loading chamber can be provided with an array of sub-chambers 5920', as shown in FIG. 59. Each sub-chamber 5920' can be used to receive a biological sample from a different specimen/donor. Similarly, the filter membrane 5940 can be formed with coinciding apertures 5940' which are axially aligned with sub-chamber 5920' so that a plurality of distinct cell blocks can be formed from differing specimens, in one centrifuging cycle.

Figure 61:
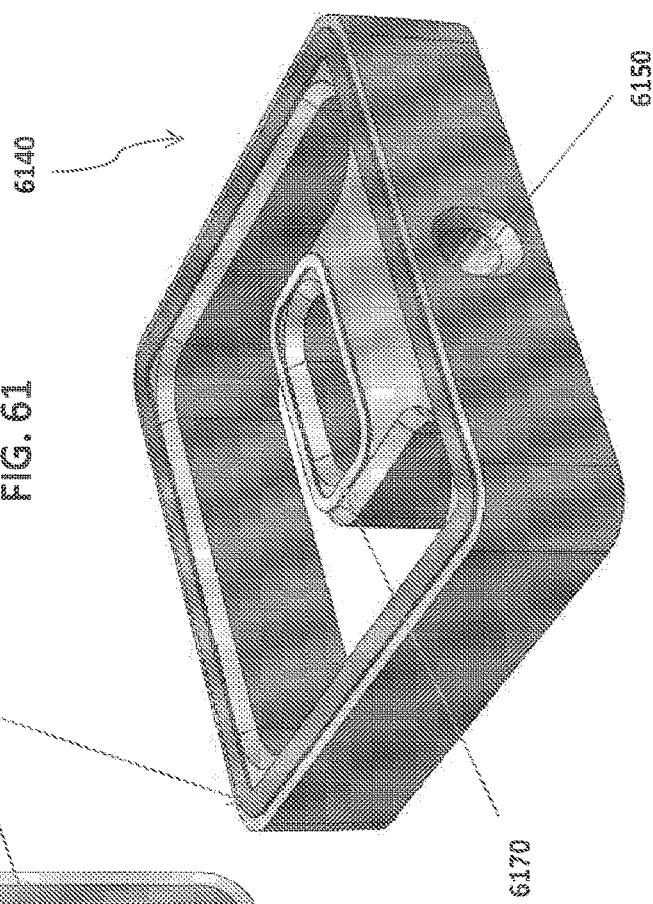
FIGS. 60-61 are additional embodiments of the filter membrane in accordance with the disclosed subject matter.
Figure 60:
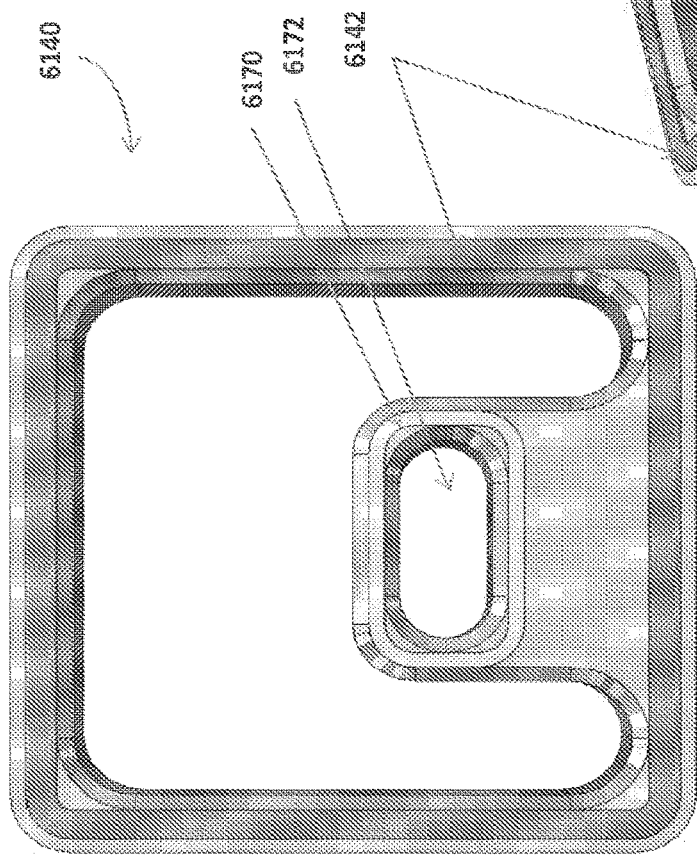
Figure 61A:
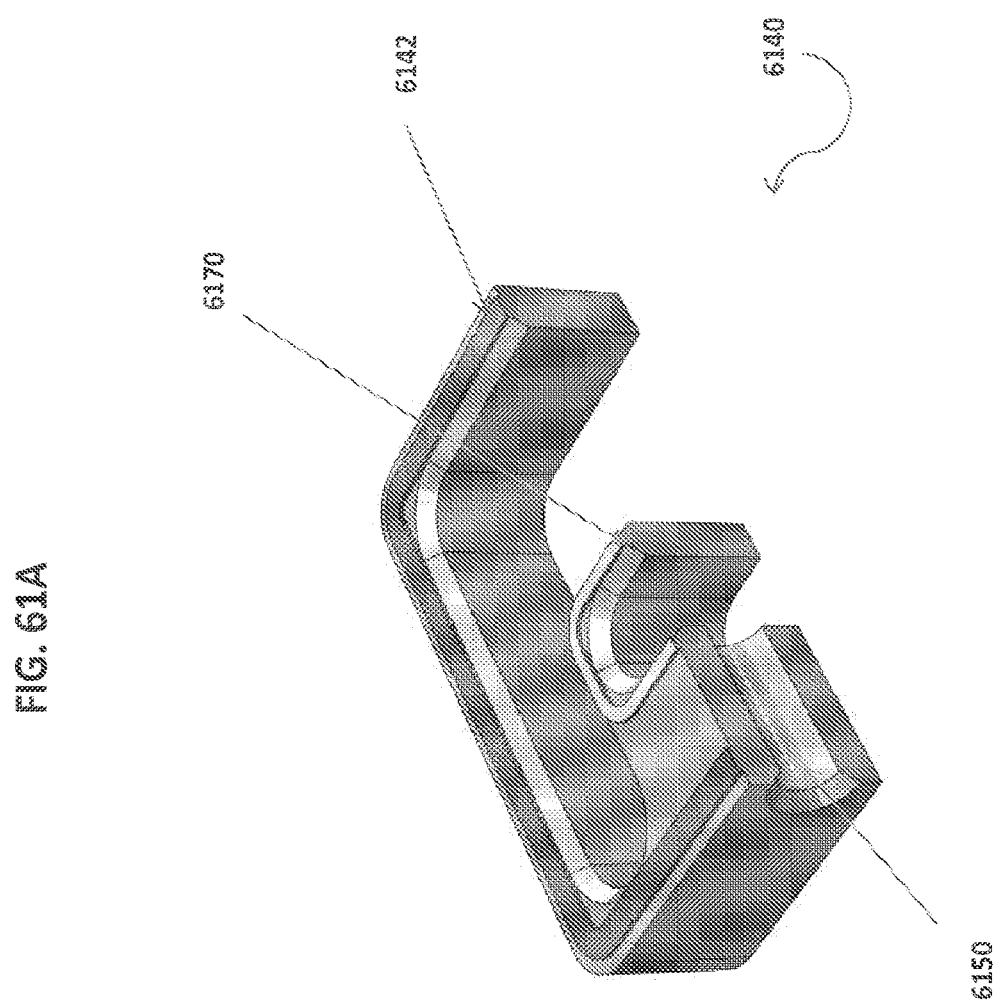
FIG. 61A is a cross sectional views of the embodiment of FIG. 60.

Referring again to the single piece retentate chamber (i.e. non-centrifuge applications) of the present disclosure, as described above with reference to FIGS. 49-51A, in another embodiment a membrane can be provided instead of the valve 4970 construction of FIG. 51a. As shown in FIGS. 60-61A, the single piece retentate chamber 6140 can be formed as a square member with upstanding sidewalls defining the border. The filter membrane border can be formed with upper and lower lips which extend inward from the sidewall. Additionally, the filter membrane 6140 is provided with two porous filter meshes (not shown), one which is substantially flush or coplanar with the top surface of the filter membrane border (attached along the inwardly extending border lips), and one which is substantially flush or coplanar with the bottom surface of the filter membrane border. In some embodiments a sealing ring 6142 can be provided along the inwardly extending border lip to facilitate coupling of the porous filter meshes to the border. In this regard the filter membrane 6140 serves as a single piece retentate chamber for the biological sample collected. At least one of the sidewalls includes an inlet port 6150 in which a biological sample with a fixative is driven into the chamber (e.g. by syringe). The membrane 6170 is positioned on the interior surface of the border sidewall, between the upper and lower lips, and protrudes inwardly to the center of the retentate chamber 6140. Additionally, a cavity or reservoir 6172 is provided adjacent to the membrane 6170. As the sample and fixative are injected into the port 6150, the solution pools in cavity 6172 until the pressure increases to displace the thin walled membrane 6172 to allow the solution to flow from the reservoir 6172, through the membrane wall(s) 6172 and into the interior chamber. The pressure within the chamber increases as the amount of biological sample injected therein increases. This internal pressure, along with gravitational forces, draw the biological sample through the porous filter membranes (not shown) leaving a cell block retentate within the chamber. As the pressure within the reservoir decreases, the membrane wall(s) 6172 revert back to the resting state forming a seal which prevents flow between the reservoir 6172 and the interior chamber. As previously described, this single piece retentate chamber is constructed of materials which permit sectioning or cutting of the retentate chamber.

Figure 62A:
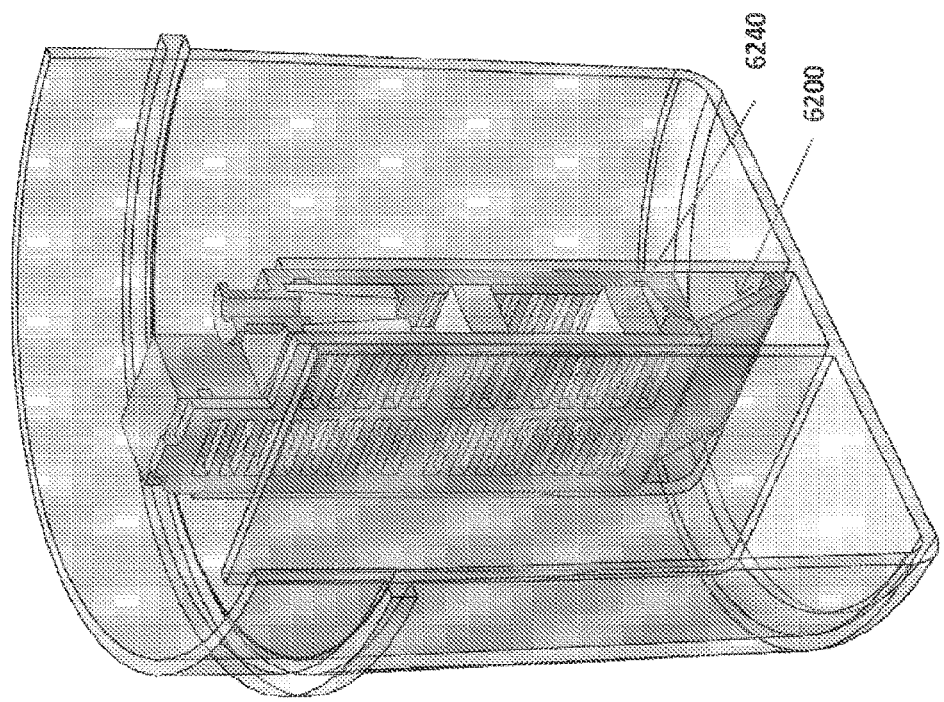
FIG. 62A is a cross sectional views of the embodiment of FIG. 62.

In accordance with an aspect of the disclosed subject matter, and similar to the containers 3200 of FIGS. 32-36F, the retentate chamber filter membrane 6240 can be housed or stored in a cassette or container 6200. In the embodiment depicted in FIGS. 62-62A, the container 6200 itself (with the filter membrane 6240 and cells collected therein) can be retained in a vessel which includes a bottom 6202 and a lid 6201. Additionally, the container 6200 (with the filter membrane 6240 and cells collected therein) can be stored within this vessel in an upright manner via the sleeves 6203, 6204.

The container 6200 is substantially rectangular, having top and a bottom surface, three perpendicular sides, and one sloped side. The top and bottom surfaces are perforated by a series of regularly spaces slots to form a grating. The top surface is affixed to one side of the container by a hinge. The top surface can be removably attached to the bottom surface, or permanently attached, e.g., via a living-hinge, as so desired. Alternatively, the top surface can be attached to the bottom surface via a tongue and groove coupling such that the top surface translates or slides in a linear fashion with respect to the bottom surface to open and close the container 6200. The grating in container 6200 allows the passage of air, water, or clearing solutions in order to clean filter membrane 6240.

Figure 62:
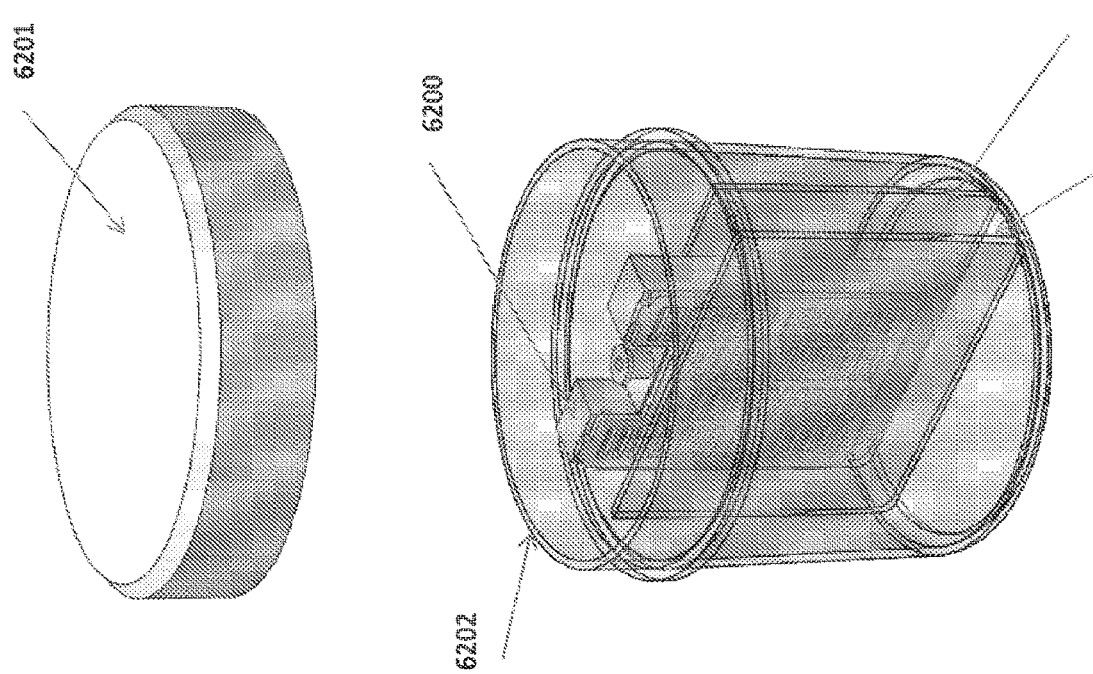
FIG. 62 is schematic view of a container for storage of the filter membrane according to an exemplary embodiment of the disclosed subject matter.
Figure 63:
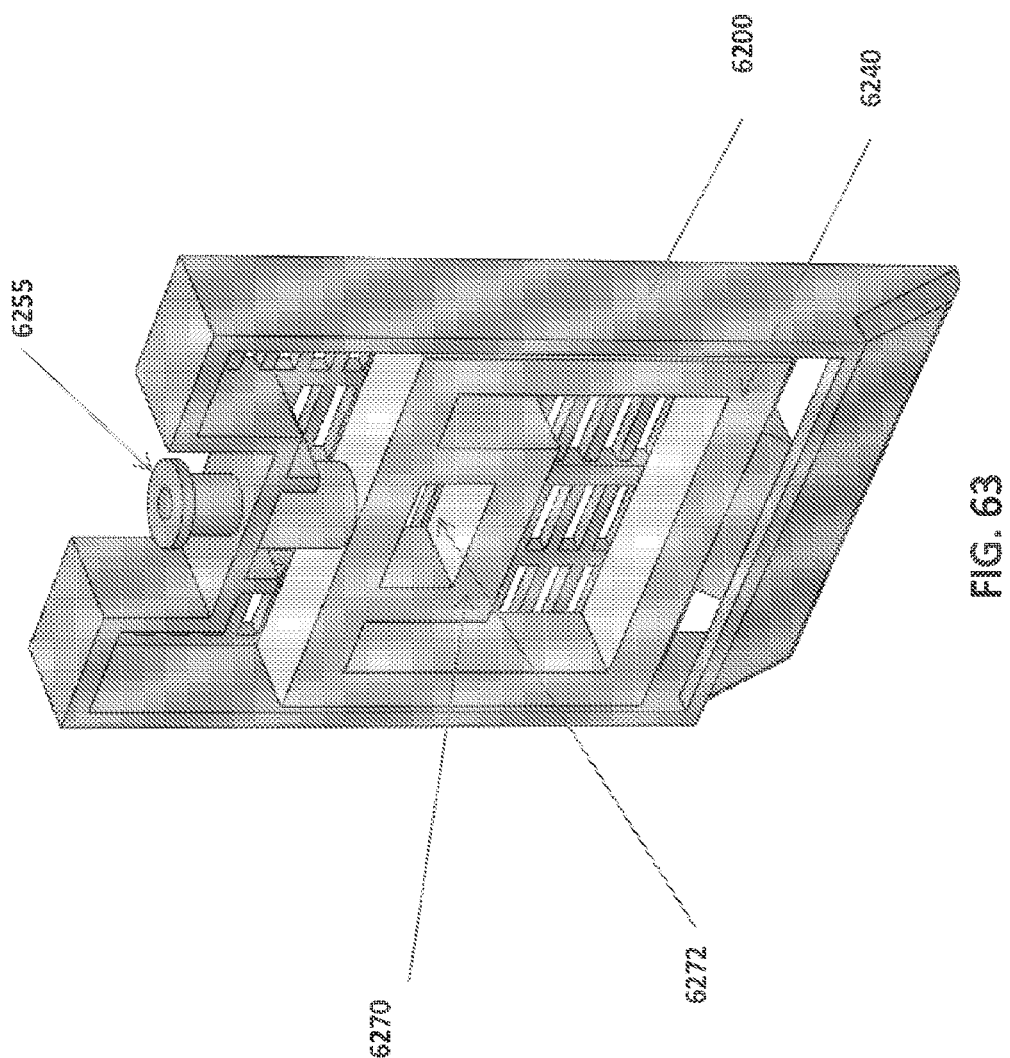
FIG. 63 is schematic view of the filter membrane according to the embodiment of FIG. 62.

As shown in FIGS. 62-63, the container is configured to receive a filter membrane retentate chamber as embodied and described in FIGS. 60-61A. Accordingly, the filter membrane 6240 includes a reservoir 6272 and membrane 6270 (see FIG. 63). The container 6200 includes a port 6255 (e.g. a luer port) which is aligned with the inlet port 6250 in the sidewall of the filter membrane 6240. The technician can connect a syringe or pump to container port 6255 to inject a biological sample through the inlet port of the filter membrane, into the reservoir 6272, and ultimately through the membrane 6270 where the filtration process can occur. The container 6200 can also be subjected to additional processing, e.g., injection of paraffin wax and molding as described above with respect to FIGS. 32-36F.

The various components identified in these embodiments can be discrete members which are assembled in such a manner that each component is readily removable (i.e. detachable without breaking). Such a construction is advantageous in that it allows for rapid assembly in preparation for the centrifuge process, and subsequent disassembly in order to rapidly access the filter membrane and the collected cell sample disposed thereon. This readily removable feature avoids risk of contamination presented by permanent or welded connections which require fracturing or breaking of components and seals, and the debris associated with such efforts, to access the filter and collected cell sample.

In some embodiments, the cell block apparatus and components are color coded. For example, the filter assembly can be color coded so that the laboratory personnel or the clinicians can easily identify the type of sample in the filter assembly. For the purpose of illustration and not limitation, the material of the filter assembly can be purple to denote a liver sample, and blue to denote a lung sample. The color codes of the filter assembly or the elongate tubular body can be coordinated with the compressive cover to function as indicia.

It is understood that the subject matter described herein is not limited to particular embodiments described, as such may, of course, vary. For example, the exemplary embodiments describe above are not limited to fine needle aspiration applications. Instead the disclosed subject matter is applicable to additional clinical settings such as processing small surgical biopsies (less than 2 cm), in research laboratories for isolating cells from bone marrow diluted by blood, analyzing small samples of engineered tissues, and purifying cells in a spin column. Accordingly, nothing contained in the Abstract or the Summary should be understood as limiting the scope of the disclosure. It is also understood that the terminology used herein is for the purpose of describing particular embodiments only, and is not intended to be limiting. Where a range of values is provided, it is understood that each intervening value between the upper and lower limit of that range and any other stated or intervening value in that stated range, is encompassed within the disclosed subject matter.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

As used herein and in the appended claims, the singular forms "a," "an," and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A medical apparatus comprising:
    an elongate tubular body having a proximal end, an opening at the proximal end, a distal end defining a first interior space therebetween, and a distalmost end of the elongate tubular body configured to matingly engage a filter assembly; and
    a filter assembly configured to matingly engage a distal portion of the elongate tubular body, the filter assembly comprising a filter membrane and a border that is sectionable for mounting on a slide for analysis on a microscope.

2. The medical apparatus of claim 1, wherein the filter membrane comprises polyethylene terephthalate.

3. The medical apparatus of claim 1, wherein the filter membrane is composed of a porous filter mesh.

4. The medical apparatus of claim 1, wherein the border of the filter assembly has an upwardly extending sidewall circumscribing the filter membrane.

5. The medical apparatus of claim 1, wherein the border of the filter assembly comprises machinable wax.

6. The medical apparatus of claim 1, further comprising a base member.

7. The medical apparatus of claim 6, wherein the base member is configured to releasably engage the distalmost end of the elongate tubular body by a threaded engagement or a ratchet engagement.

8. The medical apparatus of claim 6, wherein the base member is sized to allow the filter assembly to slide into a second interior space defined by the base member.

9. The medical apparatus of claim 6, wherein the base member comprises a cap.

10. The medical apparatus of claim 1, wherein the distal end of the elongate tubular body has a narrower opening than the proximal end.

11. The medical apparatus of claim 10, wherein the elongate tubular body comprises a section disposed between the proximal end and the distal end having a decreasing diameter along a length thereof to define a generally conical distal section of the elongate tubular body.

12. The medical apparatus of claim 1, further comprising a lid disposed at the proximal end of the elongate tubular body, the lid configured to engage the proximal end of the elongate tubular body.

13. The medical apparatus of claim 12, wherein the lid and elongate tubular body are configured to releasably engage by a threaded engagement or interference fit.

14. The medical apparatus of claim 12, wherein the lid comprises a stopper formed from a self-sealing or resealable material.

15. The medical apparatus of claim 12, wherein the lid is puncturable by a needle.

16. A medical apparatus, comprising:
an elongate tubular body having a proximal end, an opening at the proximal end, and a distal end defining an interior space therebetween, and a distalmost end of the elongate tubular body configured to matingly engage a filter assembly;
a filter assembly configured to matingly engage a distal portion of the elongate tubular body and to provide a seal with the interior space thereof, the filter assembly comprising a filter membrane and a border that is sectionable for mounting on a slide for analysis on a microscope; and
a base member configured to releasably engage the distalmost end of the elongate tubular body and to receive the filter assembly therein.

17. The medical apparatus of claim 16, wherein the filter membrane comprises polyethylene terephthalate.

18. The medical apparatus of claim 16, wherein the filter membrane is composed of a porous filter mesh.

19. The medical apparatus of claim 16, wherein the border of the filter assembly has an upwardly extending sidewall circumscribing the filter membrane.

20. The medical apparatus of claim 16, wherein the border of the filter assembly comprises machinable wax.

21. The medical apparatus of claim 16, wherein the base member is configured to releasably engage the distalmost end of the elongate tubular body by a threaded engagement or a ratchet engagement.

22. The medical apparatus of claim 16, wherein the distal end of the elongate tubular body has an opening narrower than the opening at the proximal end.

23. The medical apparatus of claim 22, wherein the elongate tubular body comprises a section disposed between the proximal end and the distal end having a decreasing diameter along a length thereof to define a generally conical distal section of the elongate tubular body.

24. The medical apparatus of claim 16, further comprising a lid disposed at the proximal end of the elongate tubular body, the lid configured to engage the proximal end of the elongate tubular body.

25. The medical apparatus of claim 24, wherein the lid and elongate tubular body are configured to releasably engage by a threaded engagement or interference fit.

26. The medical apparatus of claim 24, wherein the lid comprises a stopper formed from a self-sealing or resealable material.

* * * * *